(12) United States Patent
Koop et al.

(10) Patent No.: US 11,833,349 B2
(45) Date of Patent: Dec. 5, 2023

(54) SYSTEMS AND METHODS FOR TREATING CARDIAC ARRHYTHMIAS

(71) Applicant: CARDIAC PACEMAKERS, INC., St. Paul, MN (US)

(72) Inventors: Brendan Early Koop, Ham Lake, MN (US); Arthur J. Foster, Blaine, MN (US); Benjamin J. Haasl, Forest Lake, MN (US); Dana Sachs, Pine City, MN (US); Lili Liu, Maple Grove, MN (US); Justin Robert Alt, Minneapolis, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 99 days.

(21) Appl. No.: 16/830,568

(22) Filed: Mar. 26, 2020

(65) Prior Publication Data
US 2020/0306530 A1    Oct. 1, 2020

Related U.S. Application Data

(60) Provisional application No. 62/826,507, filed on Mar. 29, 2019.

(51) Int. Cl.
*A61N 1/05* (2006.01)
*A61N 1/375* (2006.01)

(52) U.S. Cl.
CPC ......... *A61N 1/0573* (2013.01); *A61N 1/0565* (2013.01); *A61N 1/3756* (2013.01); *A61N 1/37512* (2017.08)

(58) Field of Classification Search
CPC .............. A61N 1/0573; A61N 1/37512; A61N 1/0565; A61N 1/3756; A61N 1/0575;
(Continued)

(56) References Cited

U.S. PATENT DOCUMENTS

| 4,301,815 A | 11/1981 | Doring |
| 5,147,379 A | 9/1992 | Sabbaghian et al. |

(Continued)

FOREIGN PATENT DOCUMENTS

| EP | 1453414 A2 | 9/2004 |
| EP | 2769750 A1 | 8/2014 |

(Continued)

OTHER PUBLICATIONS

International Search Report and Written Opinion dated Mar. 8, 2019 for International Application No. PCT/US2018/066422.
(Continued)

*Primary Examiner* — Gary Jackson
*Assistant Examiner* — Alexander M Eisenberg
(74) *Attorney, Agent, or Firm* — Seager, Tufte & Wickhem LLP

(57) ABSTRACT

A leadless pacing device may include a housing having a proximal end and a distal end, and one or more electrodes supported by the housing. The housing may include a body portion and a header. A distal extension may extend distally from the header of the housing, the distal extension including one or more electrodes. The header may include a guide wire port and a guide wire lumen may extend from the guide wire port through the header of the housing and through the distal extension. A fixation member may extend from the header of the housing. The header may be formed from an over mold process.

20 Claims, 32 Drawing Sheets

(58) Field of Classification Search
CPC ............ A61N 1/37518; A61N 1/37205; A61N 2001/0578; A61N 2001/0585
See application file for complete search history.

(56) References Cited

U.S. PATENT DOCUMENTS

| | | |
|---|---|---|
| 5,170,802 A | 12/1992 | Mehra |
| 5,238,004 A | 8/1993 | Sahatjian et al. |
| 5,540,236 A | 7/1996 | Ginn |
| 5,803,928 A | 9/1998 | Tockman et al. |
| 5,807,399 A | 9/1998 | Aske et al. |
| 5,908,381 A | 6/1999 | Aznoian et al. |
| 5,925,073 A | 7/1999 | Chastain et al. |
| 5,957,842 A | 9/1999 | Littmann et al. |
| 6,070,104 A | 5/2000 | Hine et al. |
| 6,164,284 A | 12/2000 | Schulman et al. |
| 6,181,973 B1 | 1/2001 | Ceron et al. |
| 6,185,452 B1 | 2/2001 | Schulman et al. |
| 6,224,725 B1 | 5/2001 | Glocker |
| 6,231,516 B1 | 5/2001 | Keilman et al. |
| 6,395,017 B1 | 5/2002 | Dwyer et al. |
| 6,409,101 B1 | 6/2002 | D'Arrigo |
| 6,409,674 B1 | 6/2002 | Brockway et al. |
| 6,416,474 B1 | 7/2002 | Penner et al. |
| 6,442,413 B1 | 8/2002 | Silver |
| 6,445,953 B1 | 9/2002 | Bulkes et al. |
| 6,497,803 B2 | 12/2002 | Glocker et al. |
| 6,508,803 B1 | 1/2003 | Horikawa et al. |
| 6,551,477 B2 | 4/2003 | Glocker et al. |
| 6,582,441 B1 | 6/2003 | He et al. |
| 6,584,362 B1 | 6/2003 | Scheiner et al. |
| 6,592,518 B2 | 7/2003 | Denker et al. |
| 6,638,268 B2 | 10/2003 | Niazi |
| 6,783,499 B2 | 8/2004 | Schwartz |
| 6,786,918 B1 | 9/2004 | Krivoruchko et al. |
| 6,907,285 B2 | 6/2005 | Denker et al. |
| 7,003,350 B2 | 2/2006 | Denker et al. |
| 7,082,336 B2 | 7/2006 | Ransbury et al. |
| 7,114,502 B2 | 10/2006 | Schulman et al. |
| 7,164,852 B2 | 1/2007 | Cazzini et al. |
| 7,212,870 B1 | 5/2007 | Helland |
| 7,236,821 B2 | 6/2007 | Cates et al. |
| 7,248,913 B2 | 7/2007 | Hassett |
| 7,295,879 B2 | 11/2007 | Denker et al. |
| 7,309,354 B2 | 12/2007 | Mathis et al. |
| 7,310,556 B2 | 12/2007 | Bulkes |
| 7,313,444 B2 | 12/2007 | Pianca et al. |
| 7,321,798 B2 | 1/2008 | Muhlenberg et al. |
| 7,381,216 B2 | 6/2008 | Buzzard et al. |
| 7,425,200 B2 | 9/2008 | Brockway et al. |
| 7,499,758 B2 | 3/2009 | Cates et al. |
| 7,509,169 B2 | 3/2009 | Eigler et al. |
| 7,519,421 B2 | 4/2009 | Denker et al. |
| 7,529,589 B2 | 5/2009 | Williams et al. |
| 7,535,296 B2 | 5/2009 | Bulkes et al. |
| 7,572,228 B2 | 8/2009 | Wolinsky et al. |
| 7,608,099 B2 | 10/2009 | Johnson et al. |
| 7,617,007 B2 | 11/2009 | Williams et al. |
| 7,666,203 B2 | 2/2010 | Chanduszko et al. |
| 7,678,081 B2 | 3/2010 | Whiting et al. |
| 7,711,434 B2 | 5/2010 | Denker et al. |
| 7,734,343 B2 | 6/2010 | Ransbury et al. |
| 7,747,335 B2 | 6/2010 | Williams |
| 7,749,265 B2 | 7/2010 | Denker et al. |
| 7,769,466 B2 | 8/2010 | Denker et al. |
| 7,799,037 B1 | 9/2010 | He et al. |
| 7,801,626 B2 | 9/2010 | Moser |
| 7,826,903 B2 | 11/2010 | Denker et al. |
| 7,840,281 B2 | 11/2010 | Kveen et al. |
| 7,840,282 B2 | 11/2010 | Williams et al. |
| 7,865,249 B2 | 1/2011 | Reddy |
| 7,894,915 B1 | 2/2011 | Chitre et al. |
| 7,899,554 B2 | 3/2011 | Williams et al. |
| 7,937,148 B2 | 5/2011 | Jacobson |
| 7,937,161 B2 | 5/2011 | Hastings et al. |
| 7,993,351 B2 | 8/2011 | Worley et al. |
| 8,002,822 B2 | 8/2011 | Glocker et al. |
| 8,010,209 B2 | 8/2011 | Jacobson |
| 8,032,219 B2 | 10/2011 | Neumann et al. |
| 8,050,775 B2 | 11/2011 | Westlund et al. |
| 8,103,359 B2 | 1/2012 | Reddy |
| 8,103,361 B2 | 1/2012 | Moser |
| 8,116,883 B2 | 2/2012 | Williams et al. |
| 8,160,722 B2 | 4/2012 | Rutten et al. |
| 8,185,213 B2 | 5/2012 | Kveen et al. |
| 8,204,596 B2 | 6/2012 | Ransbury et al. |
| 8,224,463 B2 | 7/2012 | Worley |
| 8,239,045 B2 | 8/2012 | Ransbury et al. |
| 8,244,376 B2 | 8/2012 | Worley |
| 8,267,987 B2 | 9/2012 | Johnson et al. |
| 8,308,794 B2 | 11/2012 | Martinson et al. |
| 8,311,633 B2 | 11/2012 | Ransbury et al. |
| 8,352,028 B2 | 1/2013 | Wenger |
| 8,364,280 B2 | 1/2013 | Marnfeldt et al. |
| 8,382,813 B2 | 2/2013 | Shumer |
| 8,428,750 B2 | 4/2013 | Kolberg |
| 8,478,431 B2 | 7/2013 | Griswold et al. |
| 8,489,189 B2 | 7/2013 | Tronnes |
| 8,489,205 B2 | 7/2013 | Stotts et al. |
| 8,504,156 B2 | 8/2013 | Bonner et al. |
| 8,527,068 B2 | 9/2013 | Ostroff |
| 8,532,790 B2 | 9/2013 | Griswold |
| 8,548,605 B2 | 10/2013 | Ollivier |
| 8,571,678 B2 | 10/2013 | Wang |
| 8,615,310 B2 | 12/2013 | Khairkhahan et al. |
| 8,626,299 B2 | 1/2014 | Gross et al. |
| 8,630,710 B2 | 1/2014 | Kumar et al. |
| 8,634,280 B1 | 1/2014 | Wang et al. |
| 8,634,912 B2 | 1/2014 | Bornzin et al. |
| 8,634,919 B1 * | 1/2014 | Hou ................. A61N 1/368 607/36 |
| 8,644,934 B2 | 2/2014 | Hastings et al. |
| 8,670,824 B2 | 3/2014 | Andersen et al. |
| 8,670,842 B1 | 3/2014 | Bornzin et al. |
| 8,676,349 B2 | 3/2014 | Stalker et al. |
| 8,700,181 B2 | 4/2014 | Bornzin et al. |
| 8,712,553 B2 | 4/2014 | Reddy |
| 8,721,587 B2 | 5/2014 | Berthiaume et al. |
| 8,727,996 B2 | 5/2014 | Allan et al. |
| 8,758,365 B2 | 6/2014 | Bonner et al. |
| 8,781,605 B2 | 7/2014 | Bornzin et al. |
| 8,798,740 B2 | 8/2014 | Samade et al. |
| 8,798,770 B2 | 8/2014 | Reddy |
| 8,855,789 B2 | 10/2014 | Jacobson |
| 8,886,340 B2 | 11/2014 | Williams et al. |
| 8,894,824 B2 | 11/2014 | Glocker et al. |
| 8,903,513 B2 | 12/2014 | Ollivier |
| 8,903,573 B2 | 12/2014 | Chandra et al. |
| 8,914,131 B2 | 12/2014 | Bornzin et al. |
| 8,926,588 B2 | 1/2015 | Berthiaume et al. |
| 8,938,294 B2 | 1/2015 | Anderson et al. |
| 8,945,145 B2 | 2/2015 | Tran et al. |
| 8,945,146 B2 | 2/2015 | Steingisser et al. |
| 8,948,883 B2 | 2/2015 | Eggen et al. |
| 8,958,892 B2 | 2/2015 | Khairkhahan et al. |
| 8,989,873 B2 | 3/2015 | Locsin |
| 8,992,545 B2 | 3/2015 | Cahill |
| 8,996,109 B2 | 3/2015 | Karst et al. |
| 9,008,777 B2 | 4/2015 | Dianaty et al. |
| 9,017,341 B2 | 4/2015 | Bornzin et al. |
| 9,020,611 B2 | 4/2015 | Khairkhahan et al. |
| 9,026,229 B2 | 5/2015 | Stalker et al. |
| 9,072,872 B2 | 7/2015 | Asleson et al. |
| 9,101,281 B2 | 8/2015 | Reinert et al. |
| 9,119,959 B2 | 9/2015 | Rys et al. |
| 9,126,032 B2 | 9/2015 | Khairkhahan et al. |
| 9,155,882 B2 | 10/2015 | Grubac et al. |
| 9,168,372 B2 | 10/2015 | Fain |
| 9,204,842 B2 | 12/2015 | Mothilal et al. |
| 9,205,225 B2 | 12/2015 | Khairkhahan et al. |
| 9,216,293 B2 | 12/2015 | Berthiaume et al. |
| 9,220,906 B2 | 12/2015 | Griswold et al. |
| 9,238,145 B2 | 1/2016 | Wenzel et al. |
| 9,242,102 B2 | 1/2016 | Khairkhahan et al. |

(56) References Cited

U.S. PATENT DOCUMENTS

| | | | |
|---|---|---|---|
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,283,381 B2 | 3/2016 | Grubac et al. |
| 9,283,382 B2 | 3/2016 | Berthiaume et al. |
| 9,283,392 B2 | 3/2016 | Moore et al. |
| 9,289,612 B1 | 3/2016 | Sambelashvili et al. |
| 9,308,365 B2 | 4/2016 | Nordstrom et al. |
| 9,308,374 B2 | 4/2016 | Kveen et al. |
| 9,339,197 B2 | 5/2016 | Griswold et al. |
| 9,339,646 B2 | 5/2016 | Ollivier |
| 9,351,648 B2 | 5/2016 | Mothilal et al. |
| 9,358,387 B2 | 6/2016 | Suwito et al. |
| 9,393,427 B2 | 7/2016 | Schmidt et al. |
| 9,399,140 B2 | 7/2016 | Cho et al. |
| 9,414,857 B2 | 8/2016 | Wood et al. |
| 9,421,384 B2 | 8/2016 | Taff et al. |
| 9,433,780 B2 | 9/2016 | Regnier et al. |
| 9,446,248 B2 | 9/2016 | Sheldon et al. |
| 9,463,315 B2 | 10/2016 | Bornzin et al. |
| 9,468,755 B2 | 10/2016 | Westlund et al. |
| 9,468,773 B1 | 10/2016 | Anderson et al. |
| 9,480,850 B2 | 11/2016 | Schmidt et al. |
| 9,504,820 B2 | 11/2016 | Bonner et al. |
| 9,511,236 B2 | 12/2016 | Varady et al. |
| 9,517,336 B2 | 12/2016 | Eggen et al. |
| 9,517,337 B2 | 12/2016 | Ollivier |
| 9,526,522 B2 | 12/2016 | Wood et al. |
| 9,526,891 B2 | 12/2016 | Eggen et al. |
| 9,533,163 B2 | 1/2017 | Klimovitch et al. |
| 9,539,423 B2 | 1/2017 | Bonner et al. |
| 9,555,236 B2 | 1/2017 | Regnier et al. |
| 9,579,500 B2 | 2/2017 | Rys et al. |
| 9,610,454 B2 | 4/2017 | Doan et al. |
| 9,623,234 B2 | 4/2017 | Anderson |
| 9,662,487 B2 | 5/2017 | Kveen et al. |
| 9,669,223 B2 | 6/2017 | Auricchio et al. |
| 9,675,798 B2 | 6/2017 | Grubac et al. |
| 9,713,427 B2 | 7/2017 | Stalker et al. |
| 9,717,421 B2 | 8/2017 | Griswold et al. |
| 9,724,507 B2 | 8/2017 | Wood et al. |
| 9,750,931 B2 | 9/2017 | Wood et al. |
| 9,764,139 B2 | 9/2017 | Christensen |
| 9,775,982 B2 | 10/2017 | Grubac et al. |
| 9,808,617 B2 | 11/2017 | Ostroff et al. |
| 9,808,629 B2 | 11/2017 | Steingisser et al. |
| 9,814,896 B2 | 11/2017 | Solem |
| 9,827,426 B2 | 11/2017 | Reddy |
| 9,833,625 B2 | 12/2017 | Waldhauser et al. |
| 9,833,626 B2 | 12/2017 | Klimovitch et al. |
| 9,844,659 B2 | 12/2017 | Grubac et al. |
| 9,844,664 B2 | 12/2017 | McEvoy et al. |
| 9,861,815 B2 | 1/2018 | Tran et al. |
| 9,867,982 B2 | 1/2018 | Berthiaume et al. |
| 9,878,151 B2 | 1/2018 | Bornzin et al. |
| 9,889,295 B2 | 2/2018 | Ollivier |
| 9,956,400 B2 | 5/2018 | Haasl et al. |
| 9,974,948 B2 | 5/2018 | Ollivier |
| 9,993,648 B2 | 6/2018 | Kelly et al. |
| 10,080,888 B2 | 9/2018 | Kelly et al. |
| 10,124,163 B2 | 11/2018 | Ollivier |
| 10,130,821 B2 | 11/2018 | Grubac et al. |
| 10,159,834 B2 | 12/2018 | Drake et al. |
| 10,188,425 B2 | 1/2019 | Khairkhahan et al. |
| 10,194,927 B2 | 2/2019 | Chu et al. |
| 10,279,168 B2 | 5/2019 | Anderson |
| 10,350,408 B2 | 7/2019 | Wood et al. |
| 10,350,416 B2 | 7/2019 | Bonner et al. |
| 10,390,720 B2 | 8/2019 | Anderson et al. |
| 10,398,901 B2 | 10/2019 | Koop |
| 10,449,354 B2 | 11/2019 | Demmer et al. |
| 2003/0078618 A1 | 4/2003 | Fey et al. |
| 2004/0064172 A1* | 4/2004 | McVenes ............... A61N 1/056 607/122 |
| 2005/0101984 A1 | 5/2005 | Chanduszko et al. |
| 2005/0165472 A1 | 7/2005 | Glocker |
| 2005/0209653 A1 | 9/2005 | Herbert et al. |
| 2005/0267555 A1 | 12/2005 | Marnfeldt et al. |
| 2006/0009737 A1 | 1/2006 | Whiting et al. |
| 2006/0122522 A1 | 6/2006 | Chavan et al. |
| 2006/0241732 A1 | 10/2006 | Denker et al. |
| 2007/0106357 A1 | 5/2007 | Denker et al. |
| 2009/0082828 A1 | 3/2009 | Ostroff |
| 2010/0274227 A1 | 10/2010 | Khairkhahan et al. |
| 2011/0112548 A1 | 5/2011 | Fifer et al. |
| 2011/0270339 A1 | 11/2011 | Murray, III et al. |
| 2011/0270340 A1 | 11/2011 | Pellegrini et al. |
| 2012/0029598 A1 | 2/2012 | Zhao |
| 2012/0095539 A1 | 4/2012 | Khairkhahan et al. |
| 2012/0108922 A1 | 5/2012 | Schell et al. |
| 2012/0108986 A1 | 5/2012 | Beasley et al. |
| 2012/0109148 A1 | 5/2012 | Bonner et al. |
| 2012/0172690 A1 | 7/2012 | Anderson et al. |
| 2012/0172891 A1 | 7/2012 | Lee |
| 2012/0172892 A1* | 7/2012 | Grubac ............... A61N 1/0573 606/129 |
| 2012/0197349 A1 | 8/2012 | Griswold et al. |
| 2012/0271134 A1 | 10/2012 | Allan et al. |
| 2012/0323099 A1 | 12/2012 | Mothilal et al. |
| 2013/0012925 A1 | 1/2013 | Berthiaume et al. |
| 2013/0023975 A1* | 1/2013 | Locsin ............... A61N 1/37205 607/122 |
| 2013/0035636 A1 | 2/2013 | Beasley et al. |
| 2013/0035748 A1 | 2/2013 | Bonner et al. |
| 2013/0103047 A1 | 4/2013 | Steingisser et al. |
| 2013/0110127 A1 | 5/2013 | Bornzin et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1* | 5/2013 | Bornzin ............... A61N 1/3756 607/9 |
| 2013/0116741 A1 | 5/2013 | Bornzin et al. |
| 2013/0123872 A1 | 5/2013 | Bornzin et al. |
| 2013/0138006 A1 | 5/2013 | Bornzin et al. |
| 2013/0192611 A1 | 8/2013 | Taepke, II et al. |
| 2013/0253309 A1 | 9/2013 | Allan et al. |
| 2013/0253342 A1 | 9/2013 | Griswold et al. |
| 2013/0253346 A1 | 9/2013 | Griswold et al. |
| 2013/0253347 A1 | 9/2013 | Griswold et al. |
| 2013/0324825 A1* | 12/2013 | Ostroff ............... A61B 5/6839 600/374 |
| 2013/0325081 A1 | 12/2013 | Karst et al. |
| 2013/0345770 A1* | 12/2013 | Dianaty ............... A61B 5/283 607/36 |
| 2014/0018818 A1 | 1/2014 | Somogyi et al. |
| 2014/0058240 A1 | 2/2014 | Mothilal et al. |
| 2014/0100627 A1 | 4/2014 | Min |
| 2014/0107723 A1 | 4/2014 | Hou et al. |
| 2014/0172034 A1 | 6/2014 | Bornzin et al. |
| 2014/0172060 A1 | 6/2014 | Bornzin et al. |
| 2014/0243848 A1 | 8/2014 | Auricchio et al. |
| 2014/0257324 A1 | 9/2014 | Fain |
| 2014/0288576 A1 | 9/2014 | Bornzin et al. |
| 2014/0324145 A1 | 10/2014 | Eggen et al. |
| 2014/0378991 A1 | 12/2014 | Ollivier |
| 2015/0039070 A1 | 2/2015 | Kuhn et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0094668 A1 | 4/2015 | Wood et al. |
| 2015/0094735 A1 | 4/2015 | Ward et al. |
| 2015/0165189 A1* | 6/2015 | Ollivier ............... A61N 1/3756 607/127 |
| 2015/0283376 A1 | 10/2015 | Ollivier et al. |
| 2015/0297883 A1* | 10/2015 | Jang ............... A61N 1/0565 607/119 |
| 2015/0306378 A1 | 10/2015 | Schmidt et al. |

(56) References Cited

U.S. PATENT DOCUMENTS

| | | |
|---|---|---|
| 2015/0306381 A1 | 10/2015 | Schmidt et al. |
| 2015/0335884 A1 | 11/2015 | Khairkhahan et al. |
| 2015/0352351 A1 | 12/2015 | Muessig et al. |
| 2016/0000563 A1 | 1/2016 | Asleson et al. |
| 2016/0007924 A1 | 1/2016 | Eigler et al. |
| 2016/0015287 A1 | 1/2016 | Anderson et al. |
| 2016/0015322 A1 | 1/2016 | Anderson et al. |
| 2016/0059003 A1 | 3/2016 | Eggen et al. |
| 2016/0067446 A1 | 3/2016 | Klenk et al. |
| 2016/0067447 A1 | 3/2016 | Paspa et al. |
| 2016/0067503 A1 | 3/2016 | Berthiaume et al. |
| 2016/0082270 A1 | 3/2016 | Mothilal et al. |
| 2016/0096001 A1 | 4/2016 | Eidenschink et al. |
| 2016/0114157 A1 | 4/2016 | Haasl et al. |
| 2016/0129239 A1 | 5/2016 | Anderson |
| 2016/0158560 A1 | 6/2016 | Moore et al. |
| 2016/0158561 A1 | 6/2016 | Reddy |
| 2016/0206872 A1 | 7/2016 | Wood et al. |
| 2016/0213919 A1 | 7/2016 | Suwito et al. |
| 2016/0220829 A1 | 8/2016 | Wood |
| 2016/0228712 A1* | 8/2016 | Koop .................. A61N 1/3756 |
| 2016/0228715 A9 | 8/2016 | Bonner et al. |
| 2016/0228716 A1* | 8/2016 | Schmidt ................. A61B 90/94 |
| 2016/0235971 A1 | 8/2016 | Wood et al. |
| 2016/0243350 A9 | 8/2016 | Grubac et al. |
| 2016/0243355 A1 | 8/2016 | Wood |
| 2016/0263372 A1 | 9/2016 | Wood et al. |
| 2016/0271388 A1 | 9/2016 | Ollivier et al. |
| 2016/0279423 A1 | 9/2016 | Kelly et al. |
| 2016/0296761 A1 | 10/2016 | Doan et al. |
| 2016/0310703 A1 | 10/2016 | Drake et al. |
| 2016/0310723 A1 | 10/2016 | Eggen et al. |
| 2016/0310726 A1 | 10/2016 | Demmer et al. |
| 2016/0310747 A1 | 10/2016 | Grubac et al. |
| 2016/0325104 A1 | 11/2016 | Anderson et al. |
| 2016/0361536 A1 | 12/2016 | Grubac et al. |
| 2017/0028190 A1 | 2/2017 | O'Carroll et al. |
| 2017/0028194 A1 | 2/2017 | Bonner et al. |
| 2017/0043158 A1 | 2/2017 | Kelly et al. |
| 2017/0065369 A1 | 3/2017 | Bornzin et al. |
| 2017/0072191 A1 | 3/2017 | Ma et al. |
| 2017/0095662 A1 | 4/2017 | McDonnell et al. |
| 2017/0100582 A1 | 4/2017 | McEvoy et al. |
| 2017/0106185 A1 | 4/2017 | Orts et al. |
| 2017/0113035 A1 | 4/2017 | Bonner et al. |
| 2017/0119999 A1 | 5/2017 | Kelly |
| 2017/0136231 A1 | 5/2017 | Kelly et al. |
| 2017/0143955 A1 | 5/2017 | Soltis et al. |
| 2017/0143980 A1 | 5/2017 | Soltis et al. |
| 2017/0151429 A1 | 6/2017 | Regnier |
| 2017/0165479 A1 | 6/2017 | Rys et al. |
| 2017/0189681 A1 | 7/2017 | Anderson |
| 2017/0209688 A1 | 7/2017 | Drake et al. |
| 2017/0209689 A1 | 7/2017 | Chen et al. |
| 2017/0209690 A1 | 7/2017 | Drake et al. |
| 2017/0216575 A1 | 8/2017 | Asleson et al. |
| 2017/0224997 A1 | 8/2017 | Shuros et al. |
| 2017/0252567 A1 | 9/2017 | Koop |
| 2017/0274202 A1 | 9/2017 | Grubac et al. |
| 2017/0304624 A1 | 10/2017 | Friedman et al. |
| 2017/0312479 A1 | 11/2017 | Keaveney et al. |
| 2017/0312496 A1 | 11/2017 | Wood et al. |
| 2017/0319847 A1 | 11/2017 | Ho et al. |
| 2017/0326355 A1 | 11/2017 | Koop et al. |
| 2017/0326369 A1 | 11/2017 | Koop et al. |
| 2017/0326372 A1 | 11/2017 | Koop et al. |
| 2017/0326373 A1 | 11/2017 | Delanely, Jr. et al. |
| 2017/0340316 A1 | 11/2017 | Wood et al. |
| 2017/0340877 A1 | 11/2017 | Ollivier |
| 2017/0368338 A1 | 12/2017 | Madden et al. |
| 2018/0028805 A1 | 2/2018 | Anderson et al. |
| 2018/0030513 A1 | 2/2018 | Hasson |
| 2018/0050191 A1 | 2/2018 | Eby et al. |
| 2018/0050192 A1 | 2/2018 | Nee et al. |
| 2018/0050193 A1 | 2/2018 | Eby et al. |
| 2018/0050194 A1 | 2/2018 | Knippel et al. |
| 2018/0050195 A1 | 2/2018 | Knippel et al. |
| 2018/0071518 A1 | 3/2018 | Drake et al. |
| 2018/0104449 A1 | 4/2018 | Amar et al. |
| 2018/0104450 A1 | 4/2018 | Rickheim et al. |
| 2018/0104451 A1 | 4/2018 | Kerns et al. |
| 2018/0104452 A1 | 4/2018 | Goodman et al. |
| 2018/0161571 A1 | 6/2018 | Ollivier |
| 2018/0207434 A1 | 7/2018 | Webb et al. |
| 2018/0264256 A1 | 9/2018 | Ollivier |
| 2018/0264262 A1* | 9/2018 | Haasl .................. A61N 1/3756 |
| 2018/0264272 A1* | 9/2018 | Haasl .................. A61N 1/3756 |
| 2018/0264273 A1* | 9/2018 | Haasl ................. A61N 1/36585 |
| 2018/0264274 A1* | 9/2018 | Haasl .................... A61M 29/02 |
| 2018/0280057 A1 | 10/2018 | Seifert et al. |
| 2018/0280058 A1 | 10/2018 | Meade et al. |
| 2018/0280703 A1 | 10/2018 | Hillukka et al. |
| 2018/0303514 A1 | 10/2018 | Coyle et al. |
| 2018/0318590 A1 | 11/2018 | Kabe et al. |
| 2018/0318591 A1 | 11/2018 | Kabe et al. |
| 2018/0339160 A1 | 11/2018 | Carroll |
| 2019/0030346 A1* | 1/2019 | Li ........................ A61N 1/3702 |
| 2019/0083800 A1* | 3/2019 | Yang .................. A61N 1/3756 |
| 2019/0083801 A1* | 3/2019 | Yang ................. A61N 1/37518 |
| 2019/0126034 A1 | 5/2019 | Drake et al. |
| 2019/0134413 A1* | 5/2019 | Mar ..................... A61N 1/3756 |
| 2019/0175219 A1 | 6/2019 | Goodman et al. |
| 2019/0192863 A1* | 6/2019 | Koop ..................... A61N 1/056 |
| 2019/0192864 A1* | 6/2019 | Koop .................. A61N 1/3756 |
| 2019/0351236 A1 | 11/2019 | Koop |
| 2020/0038664 A1 | 3/2020 | Demmer et al. |
| 2020/0306547 A1* | 10/2020 | Liu .................... A61N 1/37282 |

FOREIGN PATENT DOCUMENTS

| | | |
|---|---|---|
| EP | 2818201 B1 | 7/2016 |
| EP | 2658599 B1 | 10/2016 |
| EP | 2651502 B1 | 11/2016 |
| EP | 2771064 B1 | 1/2017 |
| EP | 2780077 B1 | 1/2017 |
| EP | 3056157 B1 | 3/2018 |
| WO | 2008070120 A2 | 6/2008 |
| WO | 2016010958 A1 | 1/2016 |
| WO | 2016011042 A1 | 1/2016 |
| WO | 2016032716 A1 | 3/2016 |
| WO | 2016126465 A1 | 8/2016 |
| WO | 2016172106 A1 | 10/2016 |
| WO | 2019126281 A1 | 6/2019 |

OTHER PUBLICATIONS

International Search Report and Written Opinion dated Mar. 28, 2019 for International Application No. PCT/US2018/066447.

Invite to Pay Additional Fees dated Jun. 15, 2020 for International Application No. PCT/US2020/024842.

International Search Report and Written Opinion for International Application No. PCT/US2020/0248849 dated Jun. 29, 2020.

* cited by examiner

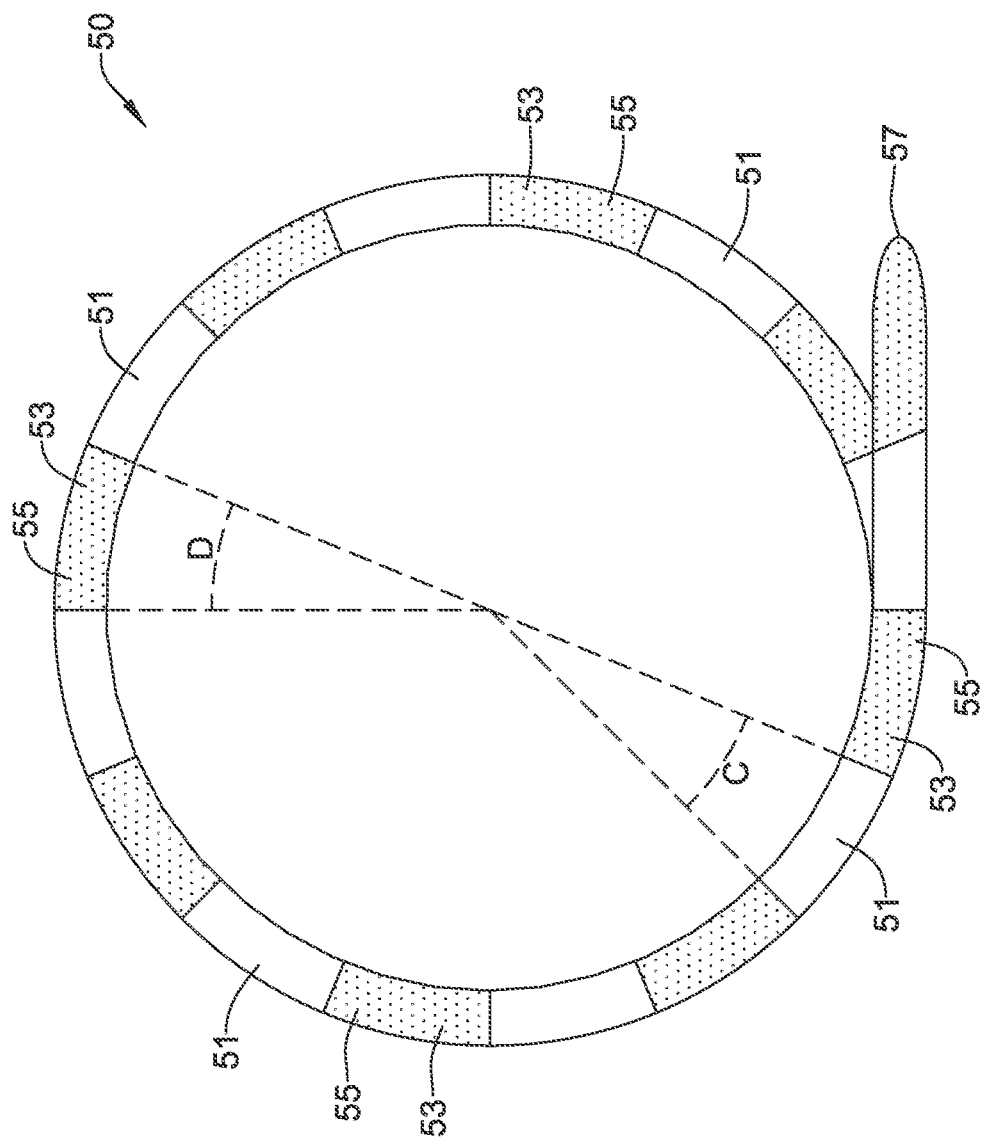

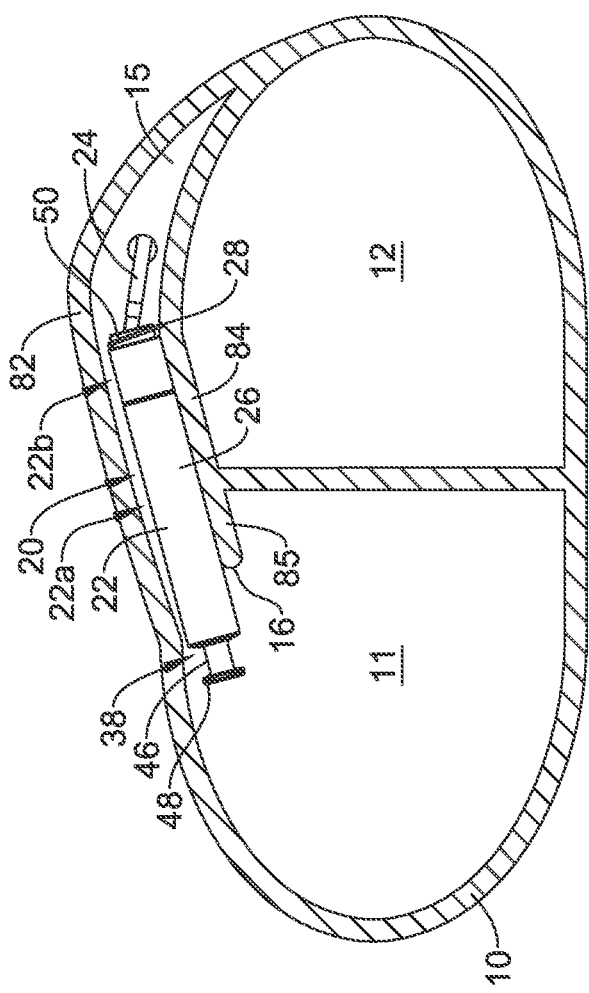

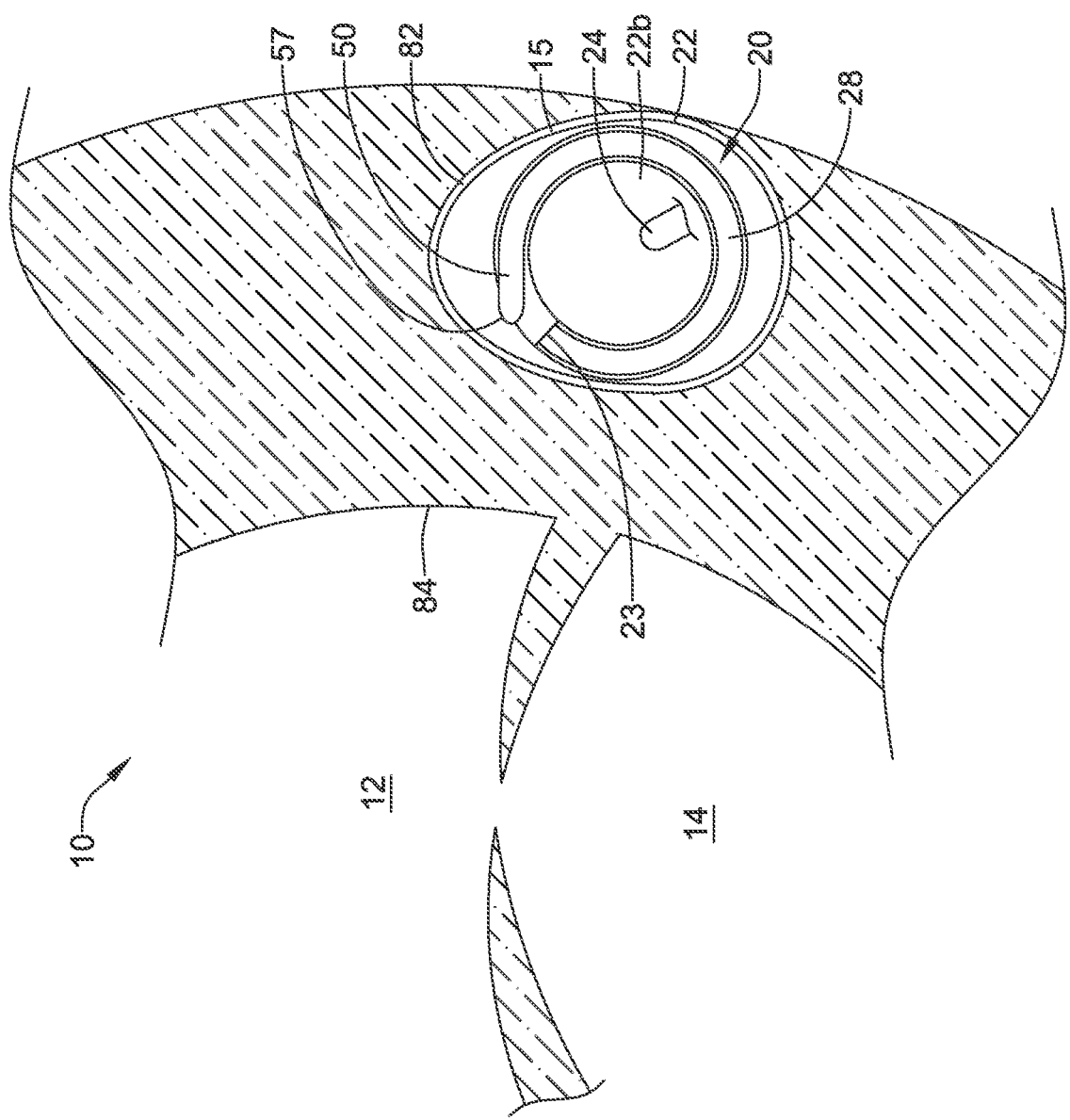

SYSTEMS AND METHODS FOR TREATING CARDIAC ARRHYTHMIAS

CROSS-REFERENCE TO RELATED APPLICATIONS

This application claims the benefit of priority under 35 U.S.C. § 119 to U.S. Provisional Application No. 62/826,507 filed Mar. 29, 2019, the entire disclosure of which is hereby incorporated by reference.

TECHNICAL FIELD

The present disclosure pertains to medical devices, and methods for manufacturing and/or using medical devices. More particularly, the present disclosure pertains to leadless cardiac devices and methods, such as leadless pacing devices and methods, and delivery devices and methods for such leadless devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

SUMMARY

This disclosure provides design, material, manufacturing method, and use alternatives for medical devices, including cardiac sensing and pacing devices and delivery devices.

A first example is a leadless pacing device for delivering electrical stimulation to a heart of a patient. The leadless pacing device includes a housing having a central longitudinal axis. The housing includes a body portion and a header extending distally from the body portion. A fixation member extends from the header. A distal extension is connected to the header and extends distally of a distal end of the header. The fixation member has a helical configuration in a relaxed state and is configured to elongate to a straightened configuration in response to an axial force applied thereto.

Alternatively or additionally to any of the examples above, the fixation member is configured to elongate to the straightened configuration in response to an axial force applied thereto that is in a range of 0.1 pound-force (lbf) to 1.0 lbf.

Alternatively or additionally to any of the examples above, the fixation member is plastically deformed to the straightened configuration in response to the axial force. Alternatively or additionally to any of the examples above, the fixation member is formed from a platinum iridium material.

Alternatively or additionally to any of the examples above, the fixation member extends at least partially around an exterior surface of the header.

Alternatively or additionally to any of the examples above, the leadless pacing device includes a drug collar positioned at least partially around the header.

Alternatively or additionally to any of the examples above, the drug collar is at least partially positioned between the fixation member and the exterior surface of the header.

Alternatively or additionally to any of the examples above, the drug collar is secured to the header with one or both of a medical grade adhesive and an interface comprising polyetheretherketone (PEEK).

Alternatively or additionally to any of the examples above, the header extends distal of a distal tip of the fixation member.

Alternatively or additionally to any of the examples above, the fixation member includes a helical anchor extending to the distal tip.

Alternatively or additionally to any of the examples above, the fixation member includes a proximal portion embedded within a proximal portion of the header, a helical coil portion surrounding and radially spaced outward from an outer surface of a distal portion of the header, and a distal tip forming a terminal end of the fixation member. The distal tip is located proximal of a distal end of the header.

Another example is a method of retrieving a leadless pacing device from a coronary sinus of a patient's heart. The method includes advancing a positioning device through a vasculature of a patient to a leadless pacing device at least partially positioned in a coronary sinus of the patient. Thereafter, the positioning device is engaged with the leadless pacing device and a force is applied to the leadless pacing device via the positioning device to extract a helical fixation anchor of the leadless pacing device from tissue surrounding the coronary sinus. Thereafter, the leadless pacing device and the positioning device are withdrawn from the coronary sinus and the vasculature of the patient.

Alternatively or additionally to any of the examples above, the force applied is a rotational force.

Alternatively or additionally to any of the examples above, the force applied is a longitudinal force.

Alternatively or additionally to any of the examples above, the helical fixation anchor is plastically deformed into a straightened configuration.

Another example is a method of positioning a leadless pacing device in a coronary sinus of a patient's heart. The method includes advancing a guidewire into a coronary sinus of a patient, and thereafter advancing a leadless pacing device over the advanced guidewire. The leadless pacing device includes a housing. The housing has a body portion and a header extending distally from the body portion. The leadless pacing device also includes a fixation member extending from the header that is configured to engage tissue adjacent the coronary sinus of the patient. The leadless pacing device is rotated in the coronary sinus to engage the fixation member with tissue adjacent the coronary sinus of the patient and secure the leadless pacing device against a wall of the coronary sinus that forms a wall of a chamber of the patient's heart.

Alternatively or additionally to any of the examples above, the leadless pacing device is advanced over the advanced guidewire while positioned within a lumen of a delivery sheath. The method further includes rotating the housing while the leadless pacing device is positioned in the coronary sinus and positioned within the lumen of the delivery sheath until a terminal tip of the fixation member is facing the wall of the coronary sinus that forms a wall of a chamber of the patient's heart.

Alternatively or additionally to any of the examples above, when the terminal tip of the fixation member is facing the wall of the coronary sinus that forms a wall of a chamber of the patient's heart, advancing the fixation member is advanced distally out of the lumen of the delivery sheath.

Alternatively or additionally to any of the examples above, the rotating step results in tissue being positioned between the fixation member and the header.

Alternatively or additionally to any of the examples above, the fixation member penetrates into a left atrial muscle of the patient's heart.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which:

FIGS. 7-13 are views of example helical coils for a fixing member, the helical coils having exposed electrically conductive surfaces;

FIG. 14 is a schematic diagram of an example implantable leadless pacing device in a heart;

FIGS. 15A-15B are schematic diagrams of an example implantable leadless pacing device in a heart;

Figure 1:
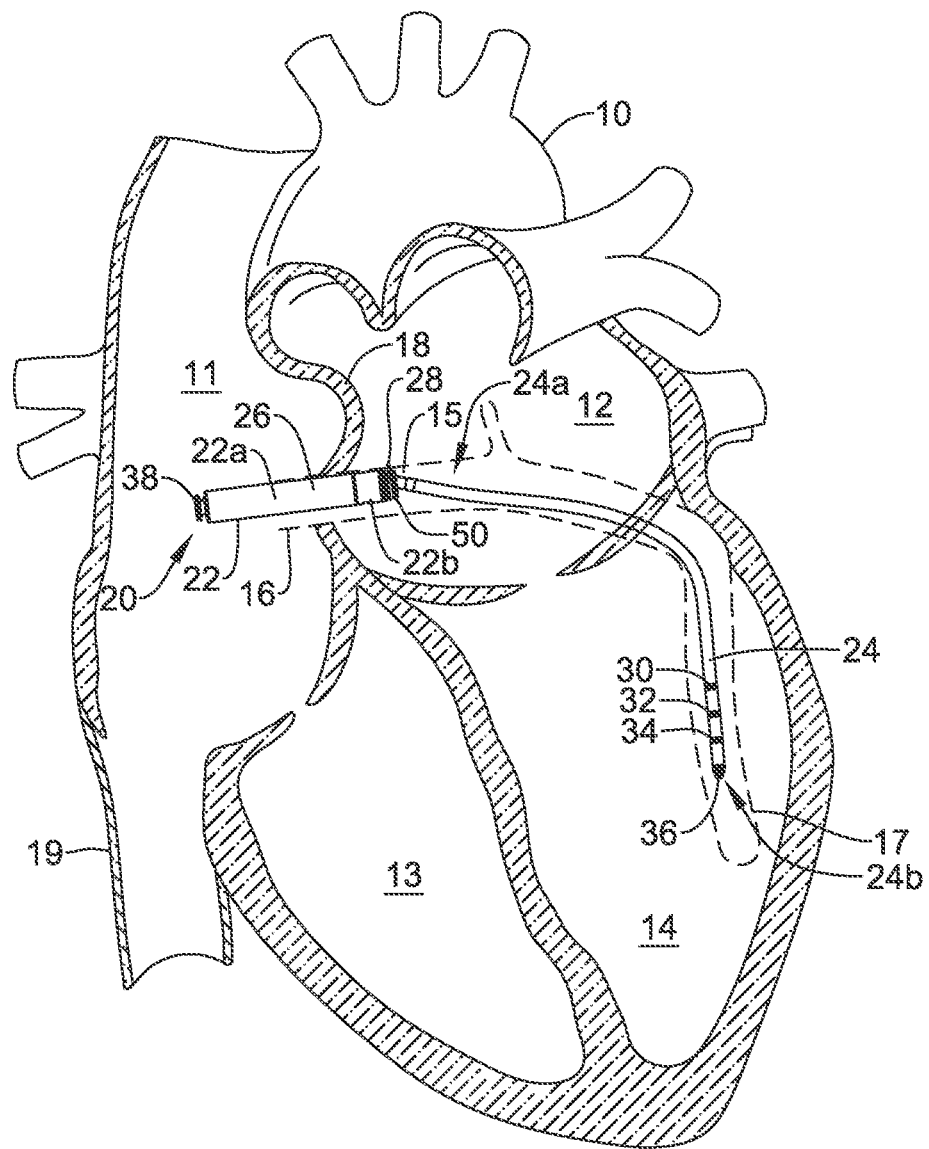
FIG. 1 is a schematic diagram of an example leadless pacing device implanted within a heart.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

The following description should be read with reference to the drawings in which similar elements in different drawings are numbered the same. The description and the drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in or around a cardiac chamber. The small capsule typically includes bipolar pacing/sensing electrodes, a power source (e.g., a battery), and associated electrical circuitry for controlling the pacing/sensing electrodes, and thus provide electrical stimulation to heart tissue and/or sense a physiological condition. In some cases, the leadless cardiac pacemakers may include a proximal and/or a distal extension extending from the small capsule, where the extension(s) may include one or more pacing/sensing electrodes. The capsule may be delivered to the heart using a delivery device which may be advanced through a femoral vein, into the inferior vena cava, into the right atrium, and into the coronary sinus and vessels extending through and/or to the coronary sinus. Accordingly, it may be desirable to provide cardiac pacing devices and delivery devices which facilitate advancement through the vasculature.

The leadless pacing device described herein may detect and treat cardiac arrhythmias, and more particularly, deliver electrical stimulation therapy to a right atrium, left atrium, right ventricle, and/or a left ventricle of a heart of a patient. For instance, one or more devices may be implanted on or within a patient's heart, and the one or more devices may be configured to deliver electrical stimulation therapy to one or more chambers of the patient's heart in accordance with one or more therapy programs and/or to treat one or more types of detected cardiac arrhythmias. Some example electrical stimulation therapies include bradycardia therapy, cardiac resynchronization therapy (CRT), anti-tachycardia pacing (ATP) therapy, defibrillation and/or cardioversion therapy, and the like. Some example cardiac arrhythmias include atrial fibrillation or atrial flutter, ventricular fibrillation, and tachycardia.

Although various features of a leadless pacing device are described herein in detail, alternative and/or additional features of an example leadless pacing device are discussed in U.S. patent application Ser. No. 15/924,985 entitled SYSTEMS AND METHODS FOR TREATING CARDIA ARRHYTHMIAS filed on Mar. 19, 2018, which is hereby incorporated by reference for all purposes; U.S. patent application Ser. No. 15/925,189 entitled SYSTEMS AND METHODS FOR TREATING CARDIA ARRHYTHMIAS filed on Mar. 19, 2018, which is hereby incorporated by reference for all purposes; U.S. patent application Ser. No. 15/925,146 entitled SYSTEMS AND METHODS FOR TREATING CARDIA ARRHYTHMIAS filed on Mar. 19, 2018, which is hereby incorporated by reference for all purposes; and U.S. patent application Ser. No. 15/925,247 entitled SYSTEMS AND METHODS FOR TREATING CARDIA ARRHYTHMIAS filed on Mar. 19, 2018, which is hereby incorporated by reference for all purposes. Hereinafter, these references incorporated by reference are referred to as the "references incorporated herein".

FIG. 1 is a conceptual diagram of an illustrative system for delivering electrical stimulation therapy to a patient's heart, including delivering electrical stimulation therapy to a right atrium, left atrium, right ventricle, and/or a left ventricle of the patient's heart. FIG. 1 shows an illustrative leadless pacing device 20 implanted in and around heart 10. Heart 10 of FIG. 1 is depicted showing a right atrium 11, a left atrium 12, a right ventricle 13, a left ventricle 14, a coronary sinus 15, a coronary sinus ostium 16, a great cardiac vein 17, and a septum 18. In FIG. 1, the coronary sinus 15 and the great cardiac vein 17 are depicted in broken lines as these features are on the posterior side of the heart 10 and would not typically be viewable from the view of FIG. 1. Although the leadless pacing device 20 is shown implanted and extending into the coronary sinus 15 and at least part of the leadless pacing device 20 typically would not be viewable from the view of FIG. 1, an entirety of the leadless pacing device 20 is depicted in solid lines for clarity purposes. In some instances, about 50% of the length of the housing 22 of the leadless pacing device 20 is inserted into the coronary sinus 15, with the proximal end region of the housing 22 positioned in the right atrium 11. In some instance about 25%-75% of the distalmost portion of the length of the housing 22 of the leadless pacing device 20 may be inserted into the coronary sinus 15, with the remaining proximal end region of the housing 22 positioned in the right atrium 11.

In the example of FIG. 1, the leadless pacing device 20 includes a housing 22 having a proximal end and a distal end and a distal extension 24 extending distally of the distal end of the housing 22. However, in some instances, the distal extension 24 may not be included and/or one or more other distal and/or proximal extensions may be included. The housing 22 may be a single portion or may have a first portion 22a (e.g., a can or body), a second portion 22b (e.g., a header or molded portion), and/or one or more other portions. It is contemplated that the housing 22 need not have the same cross sectional shape along its entire length. When implanted, the housing 22 may be fully or partially disposed within the coronary sinus 15 of the patient's heart 10, while the distal extension 24 may be fully or partially disposed within a vessel extending from the coronary sinus 15 (e.g., the great cardiac vein 17, an anterior interventricular vein, and/or other laterally descending vessel).

The housing 22 may have any dimension suitable for implantation at a target location within the heart 10 of a patient. In one example, the housing 22 may have a cross-sectional diameter or area sufficient to fit within the coronary sinus 15. Sizes of the coronary sinus 15 may vary in humans between about 0.24 inches (6 mm) to about 0.6 inches (15 mm). A diameter of the housing 22 may range, in different embodiments, between about 0.1 inches (2.54 mm) to about 0.4 inches (10 mm). These sizes may allow the housing 22 to be implanted within different sized coronary sinuses while still allowing for sufficient blood flow through the coronary sinus 15.

The housing 22 may have one or more textures on an exterior surface thereof. In some cases, the texture(s) of the housing 22 may include a first texture that facilitates stabilization of the housing 22 at a location within the patient and a second texture that facilitates blood passing by the housing 22. In one example of when the housing 22 may be configured for placement within the coronary sinus 15 of a patient, a first side of the housing 22 intended to be adjacent to and/or touching excitable myocardial tissue may have a texturized surface (e.g., with a rough texture) to facilitate stabilizing the housing 22 at an intended location and a second side of the housing 22 intended to be adjacent to and/or touching fat or pericardial tissue may have a smooth surface relative to the texturized first side of the housing 22 to facilitate blood and/or other fluids passing the housing 22 within the coronary sinus 15. The texturized surface may be texturized through sandblasting, beadblasting, sodium bicarbonate-blasting, electropolishing, depositing, and/or one or more other texturizing techniques. The smooth surface may be smooth from polishing, applying a protective layer or coating, and/or one or more other smoothing techniques.

In some embodiments, the leadless pacing device 20 may additionally include one or more electrodes. In one example, the housing 22 of the leadless pacing device 20 may support a first electrode 26 and a second electrode 28, while the distal extension 24 may support a distal electrode, or a plurality of electrodes. In some cases, the distal extension 24 may include a plurality of electrodes (e.g., a first proximal ring electrode 30, a second proximal ring electrode 32, a third proximal ring electrode 34, a distal ring electrode 36, and/or one or more other electrodes). Although the electrodes described may be indicated as being ring electrodes, other electrode types may be utilized depending on the application.

In some cases, the first electrode 26 may be formed on, along. and/or from the first portion 22a of the housing 22 and the second electrode 28 may be formed on, along, and/or from a fixation member 50 (discussed in greater detail below) extending from the housing 22. In one example, the first portion 22a of the housing 22 may be at least partially formed from an electrically conductive material and an exposed surface of such electrically conductive material may form, at least in part, the first electrode 26. Additionally, or alternatively, the second electrode 28 may be formed from one or more exposed electrically conductive surface portions of the fixation member 50 that may be exposed to cardiac tissue of the patient.

Although electrodes 26, 28 are depicted as being located at the first portion 22a of the housing 22 and the fixation member 50 extending from the second portion 22b of the housing, respectively, in some cases, the number and location of electrodes supported by the housing 22 may vary, depending on the application. For example, the leadless pacing device 20 may have electrodes disposed only on or only supported by one of the first housing portion 22a or the second housing portion 22b or one electrode on or supported by the first housing portion 22a and the other electrode on or supported by the second housing portion 22b, where the leadless pacing device 20 includes two housing portions. It may be desirable to arrange electrodes on the housing 22 at various longitudinal locations of the housing 22 to facilitate creating good contact between an electrode and a wall of the coronary sinus 15. In some instances, the leadless pacing device 20 may not have any electrodes disposed on the housing 22. Alternative and/or additional electrode configurations for a leadless pacing device 20 are discussed in the references incorporated herein.

In one example arrangement of the electrodes 26, 28 supported by the housing 22, the first electrode 26 that is located on the first portion 22a of the housing 22 may be an anode electrode and the second electrode 28 that is located at the fixation member 50 may be a cathode electrode. However, as the electrodes may be bipolar electrodes, the first electrode 26 in the example arrangement may be changed to a cathode electrode and the second electrode 28 in the example arrangement may be changed to an anode electrode. The polarity of paired bipolar electrodes may be switched regardless of locations of the electrodes.

When provided, the electrodes of the leadless pacing device 20 may be used to deliver electrical stimulation to heart 10, and/or sense one or more physiologic signals. In some cases, the leadless pacing device 20 may use one or more of the electrodes (e.g., electrodes 26-36 or other electrodes) to communicate with one or more other devices, such as, but not limited to, one or more other leadless cardiac pacemakers and/or an implantable cardioverter defibrillator. In some instances, the leadless pacing device 20 may communicate using conducted communication techniques and may deliver and/or receive communication signals through one or more of the electrodes (e.g., the electrodes 26-36 or other electrodes). Additionally or alternatively, the leadless pacing device 20 may include one or more communication wires (e.g., see FIGS. 15 and 16) configured to operate as antenna for wireless communication with and/or to receive electrical energy from one or more other devices, as discussed in greater detail below.

In some instances, the housing 22 may include a proximal member 38 (e.g., a docking hub or other member) which extends generally from the proximal end of the housing 22. In the example shown in FIG. 1, the proximal member 38 may extend proximally from the first portion 22a of the housing 22. During implantation, the proximal member 38 may be releasably coupled to a positioning device (not shown in FIG. 1). When coupled, movement of the positioning device may translate to the housing 22, thereby allowing a user, such as a physician, to maneuver the housing 22 into a proper position within the heart 10, for example into or proximate the coronary sinus 15. The positioning device may be capable of longitudinally and/or rotationally manipulating the housing 22.

In some instances, the leadless pacing device 20 may be delivered from a delivery catheter (not shown in FIG. 1), and the portion of the delivery catheter surrounding the housing 22 may conform to the housing 22 to create a secure connection between the delivery catheter and the housing 22. When the leadless pacing device 20 is in position, the delivery catheter may be retracted, or the positioning device may be used to push the housing 22 out of the delivery catheter and/or otherwise adjust a position of the leadless pacing device 20. Additionally or alternatively, the positioning device may apply rotational torque to the housing 22 to anchor the leadless pacing device 20 to cardiac tissue. In some cases, an elongate member used to adjust a position of the leadless pacing device 20 may have an interlocking mechanism (e.g., an interlocking mechanism 100, as discussed below, or other suitable interlocking mechanism). For example, the elongate member used to adjust a position of the leadless pacing device 20 may include, but is not limited to, an elongated member having a magnetic distal end configured to create a magnetic connection with the housing 22 or the proximal member 38, an elongated member having a grasping mechanism at a distal end configured to grasp the housing 22 or the proximal member 38, an elongated member having a snare mechanism at a distal end configured to engage the housing 22, and/or other suitable elongated member configured to interact with the leadless pacing device 20 to adjust a position of the leadless pacing device 20. Although not depicted in the Figures, the proximal member 38 may further include a tether anchor, which during delivery may facilitate a tether being coupled to the tether anchor to allow a user to pull the housing 22 back within the delivery catheter for further positioning. In some instances, the tether may be a suture, and the suture may be coupled to the tether anchor by looping around the tether anchor. To release the tether from the housing 22, a user may simply cut the tether or pull one end of the tether until the tether unloops itself from the tether anchor.

Although the distal extension 24 is depicted in FIG. 1, in some instances, the leadless pacing device 20 may not include the distal extension 24. Where the leadless pacing device 20 includes the distal extension 24, the distal extension 24 may extend distally from the distal end of the housing 22 (e.g., the second portion 22b of the housing 22, as shown in FIG. 1). Further, when included, the distal extension 24 may extend into the coronary sinus 15 and be secured within the coronary sinus 15. In some cases, the distal extension 24 may extend through the coronary sinus 15 and into the great cardiac vein 17, as depicted in FIG. 1, or one or more other vessels extending from the coronary sinus 15 or great cardiac vein 17.

The distal extension 24 may include a proximal end 24a and a distal end 24b. The distal end 24b of the distal extension 24 may include one or more engaging members, but this is not required and engaging members may be omitted from the distal extension 24. The engaging members, when included, may help secure the distal end 24b of the distal extension 24 within the coronary sinus 15 or the great cardiac vein 17. The engaging members may include one or more distal extension anchors (e.g., tines, helical coils, talons, or other anchors) made of silicon, a biocompatible polymer, a biocompatible metal, another biocompatible material, a shape memory material (e.g., nitinol or other shape memory material), and/or a bioabsorbable. A bioabsorbable material may be utilized to facilitate removal of the leadless pacing device 20 from a patient as endothelial growth may otherwise occur over the distal extension anchors.

In some cases, the engaging member, when included, may include one or more electrodes or wire loops and may act as an antenna to communicate with and/or receive electrical energy from one or more other devices. For example, the leadless pacing device 20 may receive an energy transfer and/or communicate using inductive and/or conductive communication techniques through electrodes and/or wire loops of the engaging member (not shown).

As mentioned above, the distal extension 24 may include one or more electrodes (e.g., electrodes 30-36). In some of these instances, the electrodes 30-36 may be disposed proximate the distal end 24b of the distal extension 24 and away from the housing 22, however in other instances, one or more of the electrodes on the distal extension 24 may span a length (e.g., an entire length or a partial length) of the distal extension 24.

In some cases, the electrodes on the distal extension 24 may be used to deliver electrical stimulation to the heart 10. For example, the leadless pacing device 20 may deliver electrical stimulation to the left ventricle 14 of heart 10 through a set of one or more of electrodes (e.g., a set from the electrodes 30-36 or other electrodes). In some cases, the leadless pacing device 20 may deliver electrical stimulation to the left ventricle 14 of the heart 10 using two or more of the electrodes 30-36 either simultaneously or with a delay (e.g. via multi-electrode pacing). In some additional or alternative cases, the leadless pacing device 20 may use one or more of the electrodes 30-36 to communicate with one or more other devices (e.g., the electrodes 30-36 may act as an antenna). For example, the leadless pacing device 20 may receive an energy transfer and/or communicate using inductive or conductive communication techniques through one or more of the electrodes 30-36.

The electrodes 26-36 and/or other electrodes on the leadless pacing device 20 may be able to sense electrical signals, provide electrical stimulation signals, or sense electrical signals and provide electrical stimulation signals. Signal processing, communication, and/or therapy pulse generation may take place at any portion of the leadless pacing device where the appropriate processing modules may be located. In one example, signal processing, communication, and therapy pulse generation for the electrodes (e.g., electrodes 26-36 and/or other electrodes) of the leadless pacing device 20 may take place in modules within or supported by the housing 22, but this is not required.

The electrodes 26-36 and/or other electrodes of the leadless pacing device 20 may be configured to perform near-field and/or far-field sensing of cardiac activation events. "Near-field" sensing of cardiac activation events refers to sensing cardiac activation events that originate in a local chamber where the corresponding electrode is located (e.g., the same chamber at which an electrode is sensing). "Far-field" sensing of cardiac activation events refers to sensing cardiac activation events that originate in a chamber other than the local chamber where the corresponding electrode is located. For example, if an electrode of the leadless pacing device 20 is located in the coronary sinus 15 with an electrode adjacent a wall of the coronary sinus 15 that forms a wall of the right atrium 11, the electrode is near-field sensing right atrium activation events and is far-field sensing left atrium activation events, left, ventricle activation events, and right ventricle activation events.

In the example of FIG. 1 where the leadless pacing device 20 is implanted in the coronary sinus 15 and a vessel (e.g., the great cardiac vein 17) extending from the coronary sinus 15, the first electrode 26 (e.g., a proximally located electrode supported by the housing 22) may be located in the coronary sinus 15 adjacent the right atrium 11, the second electrode 28 (e.g., a distally located electrode supported by the housing 22) may be located in the coronary sinus 15 adjacent the left atrium 12, and the electrodes 30-36 supported by the distal extension 24 may be located in the great cardiac vein 17 and/or a branch of the great cardiac vein 17, such that the electrodes 30-36 are positioned adjacent the left atrium 12 and/or the left ventricle 14. In such an implanted configuration, the first electrode 26 may sense near-field signals of atrial activation events (P-waves) in and provide pacing pulses to cardiac tissue of the right atrium 11, the second electrode 28 may sense near-field signals of atrial activation events (P-waves) in and provide pacing pulses to cardiac tissue of the left atrium 12, and the electrodes 30-36 supported by the distal extension 24 may sense near-field signals of ventricular activation events (R-waves) originating from atria and conducted through the atrioventricular node and His-Purkinje path in and provide pacing pulses to cardiac tissue of the left ventricle 14.

Additionally or alternatively, the electrodes 26-36 or other electrodes of the leadless pacing device 20 may sense signals through far-field sensing. For example, the electrodes 26, 28 that may be supported by the housing 22 may sense far-field ventricular activation activity (R-waves) and the electrodes 30-36 supported by the distal extension 24 may sense far-field atrial activation activity (P-waves). However, such sensed signals may be attenuated and delayed and/or the amplitude and duration may be insufficient for reliable sensing of atrial and ventricular activation activity and it may be necessary to consider signals sensed through near-field sensing when considering signals sensed through far-field sensing.

In some cases, the leadless pacing device 20 may be implanted as a single device (e.g. without one or more other leadless pacing devices or one or more implantable cardioverter defibrillators), which may provide electrical stimulation to the right atrium 11, the left atrium 12, right ventricle 13 and/or the left ventricle 14, as desired. For example, the leadless pacing device 20 may be configured to deliver electrical stimulation in accordance with a therapy program to treat atrial fibrillation or atrial flutter. However, in other cases, the leadless pacing device 20 may be implanted with one or more other leadless pacing devices and/or one or more other implantable cardioverter defibrillators implanted at one or more various locations in and/or around the heart 10.

In one example of using the leadless pacing device 20, the leadless pacing device 20 may be part of a single or multiple device system for delivering cardiac resynchronization therapy (CRT) to the heart 10. In these examples, the leadless pacing device 20 may sense cardiac electrical signals in one or both of the right atrium 11 and the left atrium 12. Once the leadless pacing device 20 senses cardiac electrical signals propagating through the right atrium 11 and/or the left atrium 12, the leadless pacing device 20 may deliver a pacing pulse to the left ventricle 14 after a delay period (e.g. an AV delay). The length of the delay period may be determined or chosen such that the leadless pacing device 20 may deliver a pacing pulse to the left ventricle 14 as the propagating cardiac electrical signals reach the right ventricle 13 and cause the right ventricle 13 to contract. In this manner, the leadless pacing device 20 may operate to provide synchronous contractions of the right ventricle 13 and the left ventricle 14. In some additional instances, the leadless pacing device 20 may adjust the delay period based on a sensed heart rate. For example, when the leadless pacing device 20 senses an increased heart rate, the leadless pacing device 20 may shorten the length of the delay period. Conversely, when the leadless pacing device 20 senses a lowered heart rate, the leadless pacing device 20 may lengthen the delay period.

As discussed, the leadless pacing device 20 may deliver pacing pulses to the right atrium 11 and/or the left atrium 12 via the coronary sinus 15. In these embodiments, the leadless pacing device 20 may begin counting the delay period at the time of or just after the leadless pacing device 20 delivers a pacing pulse to the right atrium 11 and/or the left atrium 12. As with the previously described embodiments, this may cause synchronous contractions of the right ventricle 13 and the left ventricle 14. Where the leadless pacing device 20 is part of a system with an additional leadless pacing device within the right ventricle 13, the leadless pacing device 20 may communicate a trigger to the additional leadless pacing device after the leadless pacing device 20 delivers a pacing pulse to the right atrium 11 and/or the left atrium 12. After receiving the trigger, the additional leadless pacing device may deliver a pacing pulse to the right ventricle 13 after its own delay period. In at least some of the examples, the delay period of the additional leadless pacing device and the delay period of the leadless pacing device 20 may be in alignment such that both of the additional leadless pacing device and the leadless pacing device 20 deliver pacing pulses to the right ventricle 13 and the left ventricle 14 synchronously. However, in other embodiments, the delay period of the additional leadless pacing device and the delay period of the leadless pacing device 20 may be different, for instance if conduction through the right ventricle 13 and left ventricle 14 differ, in order to cause right ventricle 13 and left ventricle 14 to contract synchronously.

Figure 2:
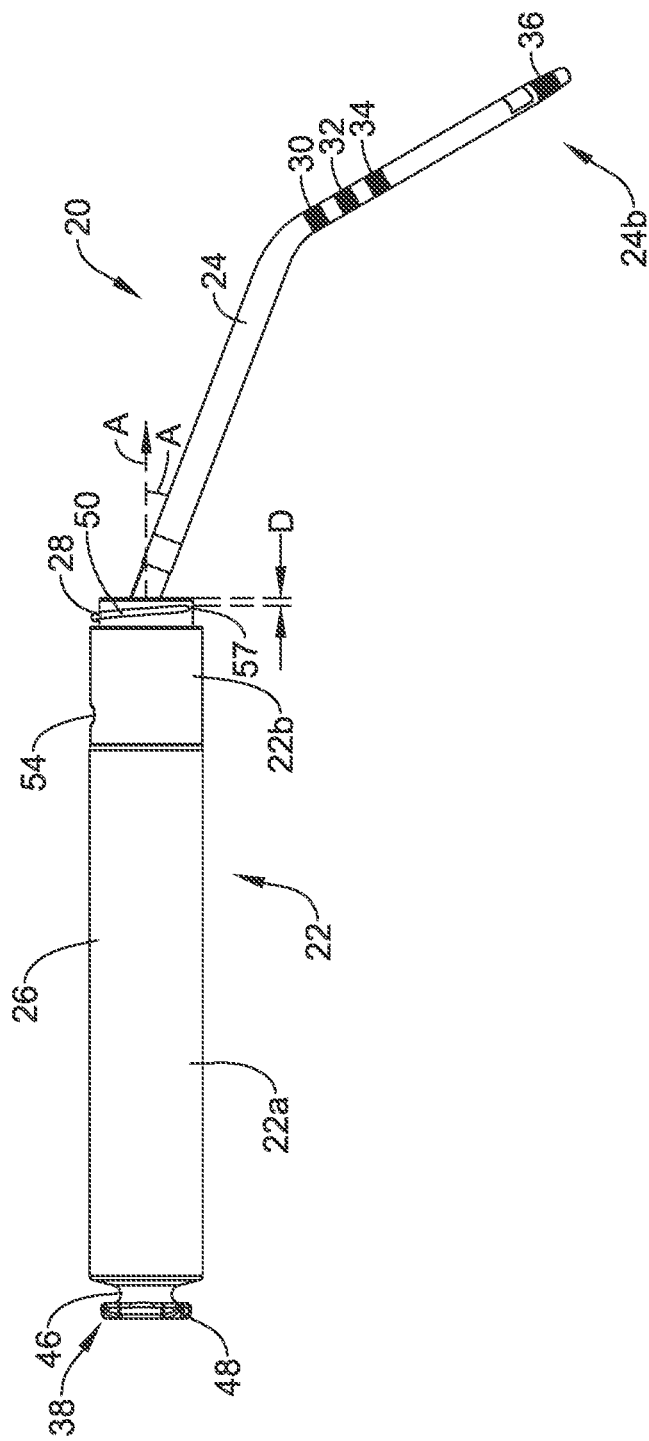
FIG. 2 is a side view of an example implantable leadless pacing device.

FIG. 2 is a schematic diagram of the illustrative leadless pacing device 20. The illustrative leadless pacing device 20 may include the housing 22 having the first housing portion 22a and the second housing portion 22b, sometimes with the distal extension 24 extending distally of the housing 22. The housing 22 may be a unitary housing or may include two or more housing portions (e.g., the first portion 22a, the second portion 22b, and/or one or more other housing portions) in which one or more components of the leadless pacing device 20 are housed. The housing 22 may generally include a biocompatible material, such as a biocompatible metal and/or polymer, and, when implanted within a patient's body, may hermetically seal the components of the leadless pacing device 20 from fluids and tissues of the patient's body.

The housing 22 depicted in FIG. 2 may have a generally straight elongated shape extending along a central longitudinal axis parallel to line A. In some instances, the housing 22, including the first body portion 22a and/or the header or second portion 22b, may be substantially cylindrical with a circumferential surface extending around the central longitudinal axis of the housing 22. In FIG. 2, both the first portion 22a and the second portion 22b extend along the central longitudinal axis and parallel to line A. The housing 22, however, may take on one or more other suitable shapes including, but not limited to, having a bent or angled portion to facilitate engaging tissue of a heart of a patient with electrodes of the leadless pacing device 20. Additional or alternative shape configurations for the housing 22 are discussed in the references incorporated herein. In some such configurations, the second portion 22b (i.e., header) may extend along the central longitudinal axis parallel to line A while the proximal portion 22a may extend along a longitudinal axis oblique to the central longitudinal axis and line A. In other instances, the first portion 22a may extend along the central longitudinal axis parallel to line A while the distal portion 22b may extend along a longitudinal axis oblique to the central longitudinal axis and line A.

As discussed above, the leadless pacing device 20 may have one or more electrodes, such as electrodes 26, 28 and/or other electrodes, which in the example shown, are supported by the housing 22 (e.g., the first electrode may be formed from an electrically conductive material of the first portion 22a of the housing and the second electrode 28 may be formed from an electrically conductive portion of the fixation member 50 supported by the second portion 22b of the housing 22). It is contemplated in some cases that the housing 22 may have a different number of electrodes, or no electrodes at all.

In instances when the housing 22 includes two or more portions, the first portion 22a may be a body and the second portion 22b may be a header. The first portion 22a may be made from a biocompatible metal material or other material suitable for enclosing electronic components of the leadless pacing device 20 and/or acting as the first electrode 26. The second portion 22b (i.e., header) may be made from a biocompatible polymer or other material. In some instances, the second portion 22b may be made from a polymer and molded over a distal end of the first portion 22a of the housing 22 and/or components extending from the first portion 22a or in communication with components housed in the first portion 22a of the housing 22 (e.g., a fixation member 50 in electrical communication with a power supply housed by the first housing portion 22a) with an over molding process. When the second portion 22b is formed from a molding technique, the distal extension 24 may be connected to the housing 22 by molding the second portion 22b over the proximal end of the distal extension 24, for example.

In some instances and as discussed above, the housing 22 may include the proximal member 38 (e.g., the docking hub) extending from a proximal end of the first portion 22a of the housing 22. In some cases, the proximal member 38 may have an extension 46 having a first outer diameter and projecting from the housing 22, where a proximal end of the extension 46 may be connected to or form an appendage 48 having a second diameter. In the example shown in FIG. 2, the second outer diameter of the appendage 48 may be greater than the first outer diameter of the extension 46, but other suitable configurations are contemplated.

During implantation, as discussed in greater detail below with respect to FIGS. 23-31, a positioning device may releasably couple to the proximal member 38. When coupled, movement of the positioning device may translate to the housing 22, thereby allowing a user to longitudinally position and/or rotate the leadless pacing device 20 during implantation. In some cases, instead of or in addition to the extension 46 and the appendage 48, the proximal member 38 may include one-half of an interlocking mechanism, and the positioning device may have the second half of the interlocking mechanism, which may releasably couple to the interlocking mechanism of the proximal member 38. Interlocking mechanisms, may be configured to create a magnetic connection, a keyed connection, and/or other suitable connections. Additional and/or alternative positioning devices and interlocking mechanisms are described in the references incorporated herein In some instances, the housing 22 may include the fixation member 50 and/or the fixation member 50 may extend from the housing 22. The fixation member 50 may include a distal penetrating tip 57 and may be configured to maintain the leadless pacing device 20 within the coronary sinus 15 when the leadless pacing device 20 is implanted within the coronary sinus 15 of the heart 10. The fixation member 50 may be or may include one or more anchors (e.g., tines, helical coils, talons, or other anchors) made of silicon, a biocompatible polymer, a biocompatible metal, another biocompatible material, a shape memory material (e.g., nitinol or other shape memory material), and/or a bioabsorbable material. A bioabsorbable material may be utilized to facilitate removal of the leadless pacing device 20 from a patient as tissue growth may otherwise occur over the anchors.

In one example of the fixation member 50, the fixation member 50 may be a helical coil or anchor, as depicted in FIG. 2, having a distal end terminating at the distal tip 57. In some instances, the fixation member 50 in a helical coil may have an outer diameter in the range of about 0.25 to about 0.275 inches and a pitch of about 0.075 inches. In one example, the fixation member 50 in a helical coil may have an outer diameter of approximately 0.247 inches, or about 0.25 inches, and the helical coil may have a pitch of approximately 0.050 inches for at least one revolution around the helical coil, but the helical coil shaped fixation member 50 may take on one or more different diameters and/or a different suitable pitch, but this is not required.

The helical coil of the fixation member 50 may be secured to the housing 22 in any suitable manner. In one example, a proximal portion of the fixation member 50 (e.g., a proximal portion of the helical coil) may be embedded (e.g., molded) within the second portion 22b of the housing 22 and a distal portion (e.g., a distal portion of the helical coil) of the fixation member 50 may extend from the second portion 22b and may be configured to engage cardiac tissue of the patient when the leadless pacing device is positioned in the patient. The distal portion of the fixation member 50 may be configured to extend about 0.5 revolutions, about 0.75 revolutions, about 1.0 revolutions, about 1.25 revolutions, about 1.5 revolutions, 0.5 to 2.0 revolutions, 0.75 to 1.5 revolutions, 1.0 to 1.25 revolutions, and/or other suitable number of revolutions about the second portion 22b of the housing 22. When the second portion 22b of the housing 22 is formed from an over mold process, a proximal portion of the fixation member 50 may be embedded within the second portion 22b during the over mold process. Other techniques for embedding and/or securing the fixation member 50 within the second portion 22b may be utilized, as desired.

In some cases, the helical coil of the fixation member 50 may terminate at the distal tip 57 positioned at or proximal of a distal end of the second portion 22b of the housing 22. For example, a distance D of the second portion 22b of the housing 22 may extend distally of the distal tip 57, as depicted in FIG. 2. Example distances of the distance D of the second portion 22b include, but are not limited to, distances in a range of about 0.005 inches to about 0.030 inches, in a range of about 0.005 inches to about 0.015 inches, and/or in a range of other suitable distances. In one example, the distance D may be about 0.005 inches. In other instances, the distal tip 57 may be flush with the distal end of the distal portion 22b.

In some cases, the helical coil of the fixation member 50 may terminate at the distal tip 57 positioned at or distal of the distal end of the second portion 22b of the housing 22. For example, the distal tip 57 may be located distal of the distal end of the second portion 22b of the housing 22 by a distance in a range of about 0.005 inches to about 0.030 inches, in a range of about 0.005 inches to about 0.015 inches, and/or in a range of other suitable distances. In one example, the distal tip 57 may be located distal of the distal end of the second portion 22b of the housing 22 by a distance of about 0.005 inches.

In a relaxed, equilibrium state, the distal tip 57 of the fixation member 50 may extend tangentially from the outer circumference of the helical portion of the fixation member 50 such that the distal tip 57 extends radially outward beyond the circumferential surface of the housing 22, such as radially outward beyond the circumferential surface of the first portion 22a and/or the second portion 22b of the housing 22.

When the fixation member 50 takes the form of a helical coil and/or other configurations, the fixation member 50 may be configured, at least in part, from a material that is configured to penetrate and engage tissue of a heart, that is electrically conductive, that is radiopaque, and/or that is flexible and/or has shape memory properties. Examples of such materials may include, but are not limited to, stainless steel, nickel-cobalt alloy (e.g. MP35N or other suitable nickel-cobalt alloy), platinum-iridium alloy (e.g., an alloy of 70% platinum and 30% iridium, an alloy of 80% platinum and 20% iridium, and/or other suitable platinum-iridium alloy), titanium (e.g., grade 1, hardened titanium; grade 1, annealed titanium, and/or other suitable titanium), nickel-titanium alloys (e.g., Nitinol and/or other suitable nickel-titanium alloys), suitable noble metals, a combination of such materials (e.g., material combination having a nickel-titanium alloy core layer with a platinum-iridium alloy outer layer), and/or other suitable materials. In some cases, the material forming the fixation member 50 may be a radiopaque material to facilitate aligning the fixation member 50 with a target location. The fixation member 50 taking the form of a helical coil may be formed from a material (e.g., a wire or other suitable material) having a diameter (e.g., a greatest cross-sectional distance) suitable for penetrating and engaging tissue of a heart, conducting electricity, and/or for being flexible or bendable. Examples of suitable diameters include, but are not limited to, 0.001-0.100 inches, 0.010-0.020 inches, 0.014-0.016 inches, and/or other suitable diameters. In one example of a fixation member 50, the fixation member 50 may be at least partially formed from an alloy of 80% platinum and 20% iridium having a 0.015 inch diameter, but this is not required.

In some cases, the fixation member 50 having a helical coil configuration may be able to straighten or elongate from the helical configuration when the fixation member 50 is engaging tissue and an axial force is applied to the leadless pacing device 20. In some instances, the fixation member 50 may be plastically deformed and elongated into a straightened configuration from its helical configuration when subjected to an axial force. Such a configuration of the fixation member 50 may facilitate removal of the leadless pacing device 20 from an implanted position within the coronary sinus 15 and may reduce risk of the fixation member 50 causing damage to the patient due to perforation or bruising. In some cases, an amount of force needed to cause the fixation member to elongate from a relaxed helical configuration may be dependent on material type and/or thickness of material. An example amount of force needed to cause the fixation member 50 to elongate (e.g., be plastically deformed) from a relaxed helical configuration to an elongated straightened configuration may be set in the range of about 0.1-1.0 pound-force (lbf), in the range of about 0.1-0.5 lbf, at about 0.25 pound-force (lbf), at about 0.50 lbf, less than about 1.0 lbf, and/or other suitable force amount so as not to cause undue trauma to patient when applying the axial force, but to require enough force such that the fixation member 50 does not unintentionally elongate.

In at least some examples, the fixation member 50 may be configured to at least partially maintain the housing 22 in a desired position with respect to the lumen of coronary sinus 15. For instance, when the fixation member 50 is in a helical anchor configuration, the fixation member 50 may engage tissue of a patient's heart and press at least part of the housing 22 (e.g., the second portion 22*b*) against the wall of the coronary sinus 15 that forms a wall of a chamber of the heart 10 (e.g., by positioning a portion of the wall of the coronary sinus 15 between the fixation member 50 and the second portion 22*b* of the housing 22).

Although one fixation member 50 is depicted on the housing 22 in the Figures, the housing 22 may support one or more additional fixation members that are axially spaced from the fixation member 50 depicted in the Figures. In other instances, the housing 22 may not include a fixation member 50.

In some cases, as discussed above, the fixation member 50 may include or form one or more electrodes (e.g., the second electrode 28 or other suitable electrode) and/or may act as an antenna to communicate with and/or receive electrical energy from one or more other devices. For example, the leadless pacing device 20 may receive an energy transfer and/or communicate using inductive and/or conductive communication techniques through electrodes of the fixation member 50.

In at least some cases, the housing 22 may have a guide wire port 54 extending through a side of the housing 22 (e.g., opening out to a side of the housing 22), where the side extends from a first end to a second end of the housing 22. In some cases, the guide wire port 54 may be disposed in or proximate the second portion 22*b* of the housing 22 and may be configured to receive a guide wire. Where the leadless pacing device 20 includes the distal extension 24, the distal extension 24 may include a corresponding guide wire port extending out of a distal tip of the distal end 24*b* of the distal extension 24. In such instances, a guide wire may be placed down the great cardiac vein 17 (or other vessel in communication with the coronary sinus 15). The leadless pacing device 20 may be tracked over the guide wire by threading the distal extension 24 over a proximal end of the guide wire, and then advancing the leadless pacing device 20 over the guide wire until in position. In embodiments where the leadless pacing device 20 does not include the distal extension 24, the housing 22 may include a second guide wire port.

When included with the leadless pacing device 20, the distal extension 24 may extend from the housing 22 at any suitable angle. In some cases, the distal extension 24 may extend from the housing 22 at an angle A relative to line A, where line A may be a line along or parallel to the central longitudinal axis of the housing 22. Angle A may be an oblique angle, such that the distal extension 24, while in a natural or equilibrium state in which no external forces are applied to bend or flex the distal extension 24, extends from the second portion 22*b* of the housing 22 at a non-parallel angle to the central longitudinal axis of the housing 22 and/or the central longitudinal axis of the second portion 22*b* of the housing 22. In other words, the base portion of the distal extension 24, which may be rigidly or fixedly mounted to the second portion 22*b* of the housing 22 at a fixed orientation relative to the second portion 22*b* of the housing 22, may be affixed or secured to the second portion 22*b* at the oblique angle A in an equilibrium state. For instance the base portion of the distal extension 24, which may include a portion extending into and surrounded by the second portion 22*b* (e.g., molded or affixed within the second portion 22*b*), may exit or otherwise extend directly from the distal end of the second portion 22*b* at the oblique angle A in an equilibrium state, such that the central longitudinal axis of the base portion of the distal extension 24 is oriented at the oblique angle A relative to the central longitudinal axis of the housing 22. In some instances, the oblique angle A may be in the range of 10 degrees to 50 degrees, in the range of 10 degrees to 40 degrees, in the range of 10 degrees to 30 degrees, in the range of 15 degrees to 35 degrees, or in the range of about 20 degrees to 25 degrees, for example. When the distal extension 24 extends at an oblique angle relative to the line A, the configuration may facilitate threading a guide wire through the distal extension 24 by aligning a guide wire lumen portion of the distal extension 24 with a guide wire lumen portion of the housing 22 such that bend in a guide wire lumen at a proximal end of the distal extension 24 may be mitigated and/or eliminated. Thus, the distal extension 24 may extend distally from the second portion 22*b* of the housing 22 toward the circumferential side of the housing 22 opposite (e.g., 180 degrees opposite) from the guide wire port 54 positioned on a circumferential surface of the second portion 22*b* of the housing 22.

The distal extension 24 may be a thin, elongated, and flexible member, particularly in relation to the housing 22. For instance, the distal extension 24 may be between two and ten times the length of the housing 22. Additionally and as discussed above, the distal extension 24 may have one or more engaging members. In some cases, the engaging member, when included, may be disposed at or near the distal end 24*b* of the distal extension 24. In some cases, the distal extension 24 may include one or more electrodes (e.g., electrodes 30-36).

The electrodes 30-36, as discussed above, and/or other electrodes may be disposed proximate the distal end 24*b* of the distal extension 24, or may be spread out along the length of distal extension 24 (e.g., longitudinally spaced from one another), as shown in FIG. 2. Other arrangements and/or configurations of electrodes on the distal extension 24 are contemplated and may be utilized. In one example arrangement of electrodes (e.g., utilizing electrodes 30-36), each of the electrodes may be ring electrodes and the electrode 36 (e.g., a distal ring electrode) may be disposed on the distal extension 24 near a distal tip of the distal extension 24, the electrode 34 (e.g., a third proximal ring electrode) may be spaced forty (40) millimeters proximal of the electrode 36, the electrode 32 (e.g., a second proximal ring electrode) may be spaced ten (10) millimeters proximal of the electrode 34, and the electrode 30 (e.g., a first proximal ring electrode) may be spaced ten (10) millimeters proximal of the electrode 32. Such a configuration of electrodes 30-36 may align with the left atrium 12 when the distal extension 24 is inserted into the great cardiac vein 17 or other vessel to allow the leadless pacing device 20 to sense and/or pace the left atrium 12 of the patient's heart 10. In some cases, the distal extension 24 may be biased to form a shape such as a helical coil or one or more loops.

Figure 3:
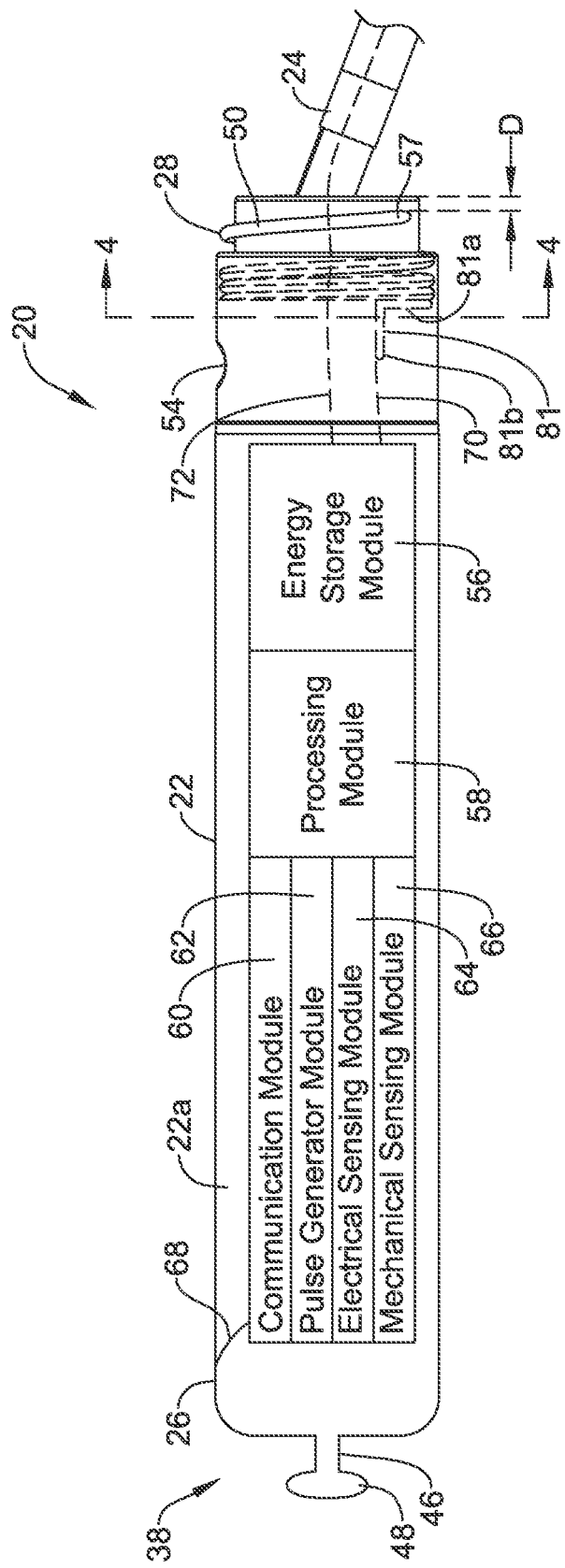
FIG. 3 is a schematic block diagram of an example implantable leadless pacing device.

FIG. 3 is a schematic block diagram of one or more electronics modules that may be contained within the housing 22 of the leadless pacing device 20. In some instances, the leadless pacing device 20 may include an energy storage module 56 (e.g., a power supply for supplying/providing a power supply voltage), a processing module 58, a communication module 60, a pulse generator module 62, an electrical sensing module 64, and/or a mechanical sensing module 66. FIG. 3 also depicts conductors 68-72 that may extend from one or more of modules 56, 58, 60, 62, 64, and/or to one or more electrodes (e.g., the electrodes 26-36 or other electrodes).

Although only three conductors are depicted in FIG. 3, a different conductor may extend from the modules in the housing 22 to each of the electrodes of the leadless pacing device 20. Additionally or alternatively, one or more conductors may be provided to facilitate communication and/or power transfers between the electronics module of the leadless pacing device 20 and one or more other electrical devices. Accordingly, in at least some instances, all of the electronic elements and energy storage modules of the leadless pacing device 20 may be contained within the housing 22, while only the one or more conductors extend to the electrodes. In one example, the conductor 68 may extend to the first electrode 26 supported by the housing 22, the conductor 70 may extend to the second electrode 28 supported by the housing 22 (e.g., to a tail 81 of the fixation member 50 and/or other suitable element in electrical communication with the second electrode 28), and the conductor 72 may be representative of the conductors extending to the electrodes 30-36 on the distal extension, where a single conductor may extend to each electrode 30-36 and the conductor extending to the distal ring electrode 36 may be coiled along and/or around a guide wire lumen 76 of the distal extension 24 until the conductor reaches the distal ring electrode 36. Additionally or alternatively, other conductors may be coiled around the guide wire lumen 76 of the distal extension 24, as desired. Each conductor extending to an electrode may be electrically isolated from the other conductors and in some cases, each conductor may extend to an associated electrode through its own lumen, but this is not required.

In the example shown FIG. 3, the communication module 60 may be electrically coupled to electrodes 26-36 and may be configured to deliver communication signals, such as electrical communication pulses, to tissues of the patient for communicating with other devices such as sensors, programmers, other medical devices, and/or the like. Electrical communication pulses, as used herein, may be any modulated signal that conveys information to another device, either by itself or in conjunction with one or more other modulated signals. In some embodiments, electrical communication pulses may be limited to sub-threshold signals that do not result in capture of the heart yet still convey information. The electrical communication pulses may be delivered to another device that is located either external or internal to the patient's body. The communication module 60 may additionally be configured to sense for electrical communication pulses delivered by other devices, which may be located external or internal to the patient's body. Descriptions of additional and/or alternative components or features of the communication module 60 are described in the references incorporated herein.

The pulse generator module 62 may be configured to generate electrical stimulation pulses and deliver the electrical stimulation pulses to tissues of a patient via one or more of the electrodes 26-36 in order to effectuate one or more electrical stimulation therapies. Electrical stimulation pulses as used herein are meant to encompass any electrical signals that may be delivered to tissue of a patient for purposes of treatment of any type of disease or abnormality. The pulse generator module 62 may include one or more capacitor elements and/or other charge storage devices to aid in generating and delivering appropriate electrical stimulation pulses. In the embodiment shown, the pulse generator module 62 may use energy stored in the energy storage module 56 to generate the electrical stimulation pulses. Descriptions of additional and/or alternative components or features of the pulse generator module 62 are described in the references incorporated herein.

The electrical sensing module 64 may be electrically connected to one or more electrodes 26-36 and the electrical sensing module 64 may be configured to receive cardiac electrical signals conducted through electrodes 26-36. In some embodiments, the cardiac electrical signals may represent local information (e.g., near-field information) from the chamber at or about which an electrode of the leadless pacing device 20 is located when the leadless pacing device 20 has been implanted in the coronary sinus 15 and/or a vessel extending therefrom. Descriptions of additional and/or alternative components or features of the electrical sensing module 64 are described in the references incorporated herein.

The mechanical sensing module 66 may include, or be electrically connected to, various sensors, such as accelerometers, blood pressure sensors, heart sound sensors, blood-oxygen sensors, and/or other sensors which measure one or more physiological parameters of the heart and/or patient. The mechanical sensing module 66, when present, may gather signals from the sensors indicative of the various physiological parameters. Both the electrical sensing module 64 and the mechanical sensing module 66 may be connected to the processing module 58 and may provide signals representative of the sensed cardiac electrical signals and/or physiological signals to the processing module 58. Although described with respect to FIG. 3 as separate sensing modules, in some embodiments, the electrical sensing module 64 and the mechanical sensing module 66 may be combined into a single module. Descriptions of additional and/or alternative components or features of the mechanical sensing module 66 are described in the references incorporated herein.

The processing module 58 may be configured to control the operation of the leadless pacing device 20. For example, the processing module 58 may be configured to receive near-field and/or far-field cardiac electrical signals from the electrical sensing module 64 and/or physiological signals from the mechanical sensing module 66. Based on the received near-field and/or far-field signals, the processing module 58 may determine, for example, occurrences and types of arrhythmias (e.g., when an atrial and/or a ventricular event occurs). The processing module 58 may further receive information from the communication module 60. In some embodiments, the processing module 58 may additionally use such received information to determine occurrences and types of arrhythmias. Based on a determined arrhythmia (e.g., a determined atrial and/or ventricular cardiac event), the processing module 58 may control the pulse generator module 62 to generate electrical stimulation pulses in accordance with one or more electrical stimulation therapies to treat the determined arrhythmia. Aside from controlling the pulse generator module 62 to generate different types of electrical stimulation pulses and in different sequences, in some embodiments, the processing module 58 may also control the pulse generator module 62 to generate the various electrical stimulation pulses with varying pulse parameters. In some embodiments, the processing module 58 may further control the communication module 60 to send information to other devices. In further instances, the processing module 58 may control switching circuitry by which the communication module 60 and the pulse generator module 62 deliver electrical communication pulses and/or electrical stimulation pulses to tissue of the patient. The processing module 58, in additional instances, may include a memory circuit and the processing module 58 may store information on and read information from the memory circuit. In other instances, the leadless pacing device 20 may include a separate memory circuit (not shown) that is in communication with the processing module 58, such that the processing module 58 may read and write information to and from the separate memory circuit. Descriptions of additional and/or alternative components or features of the processing module 58 are described in the references incorporated herein.

The energy storage module 56 may provide a power source to the leadless pacing device 20 for its operations. In some embodiments, the energy storage module 56 may be a non-rechargeable lithium-based battery. In other embodiments, the non-rechargeable battery may be made from other suitable materials. In some embodiments, the energy storage module 56 may include a rechargeable battery. In still other embodiments, the energy storage module 56 may include other types of energy storage devices such as super capacitors. Descriptions of additional and/or alternative components or features of the energy storage module 56 are described in the references incorporated herein.

The tail 81, which may be a monolithic portion of the fixation member 50, may take on any suitable configuration and may be configured for viewing as a radiopaque marker in images of the patient when the leadless pacing device 20 is being inserted into a patient, is being implanted in a patient, is implanted in a patient, and/or is being removed from a patient. The tail 81 of the fixation member 50 may include a radially extending portion 81a and a proximally extending portion 81b.

In some instances, the radially extending portion 81a may be located proximal of the helical portion of the fixation member 50, such that the radially extending portion 81a is arranged between the helical portion of the fixation member 50 and the proximally extending portion 81b. Alternatively, the proximally extending portion 81b may be located proximal of the helical portion of the fixation member 50, such that the proximally extending portion 81b is arranged between the helical portion of the fixation member 50 and the radially extending portion 81a. Thus, the radially extending portion 81a may be located at a distal end of the proximally extending portion 81b (e.g., as pictured in the Figures.) or the radially extending portion 81a may be located at a proximal end of the proximally extending portion 81b. Further, the radially extending portion 81a may extend radially inward from an inner diameter of a helical coil forming the fixation member 50 any suitable distance for viewing the radially extending portion 81a in an image of an end view of the leadless pacing device 20 within a patient. Example distances the radially extending portion 81a may extend include suitable distances less than or greater than a distance from the inner diameter of the helical coil forming the fixation member 50 to a central axis of the second portion 22b of the housing 22. Such distances may include, but are not limited to, distances in a range of about 0.010 inches to about 0.1235 inches, about 0.010 inches to about 0.10 inches, about 0.010 inches to about 0.050 inches, about 0.015 inches to about 0.045 inches, and/or other suitable ranges. In some examples, the radially extending portion 81a may extend inward about 0.015 inches, about 0.030 inches, or about 0.045 inches from the inner diameter of the helical coil forming the fixation member 50.

The proximally extending portion 81b may extend proximally from a helical coil portion and/or the radially extending portion 81a of the fixation member 50 any suitable distance for viewing the proximally extending portion 81b in an image of a side view of the leadless pacing device 20 within a patient. Example distances the proximally extending portion 81b may extend include, but are not limited to, less than about 0.045 inches, about 0.045 inches, or greater than about 0.045 inches. In some cases, the proximally extending portion 81b may extend up to an entire length of the second portion 22b of the housing 22. In some instances, proximal extending portion 81b may have a length of about 0.015 inches to about 0.2 inches, about 0.015 inches to about 0.1 inches, about 0.015 inches to about 0.05, about 0.03 inches to about 0.2 inches, about 0.03 inches to about 0.1 inches, or about 0.03 inches to about 0.05 inches.

Figure 4:
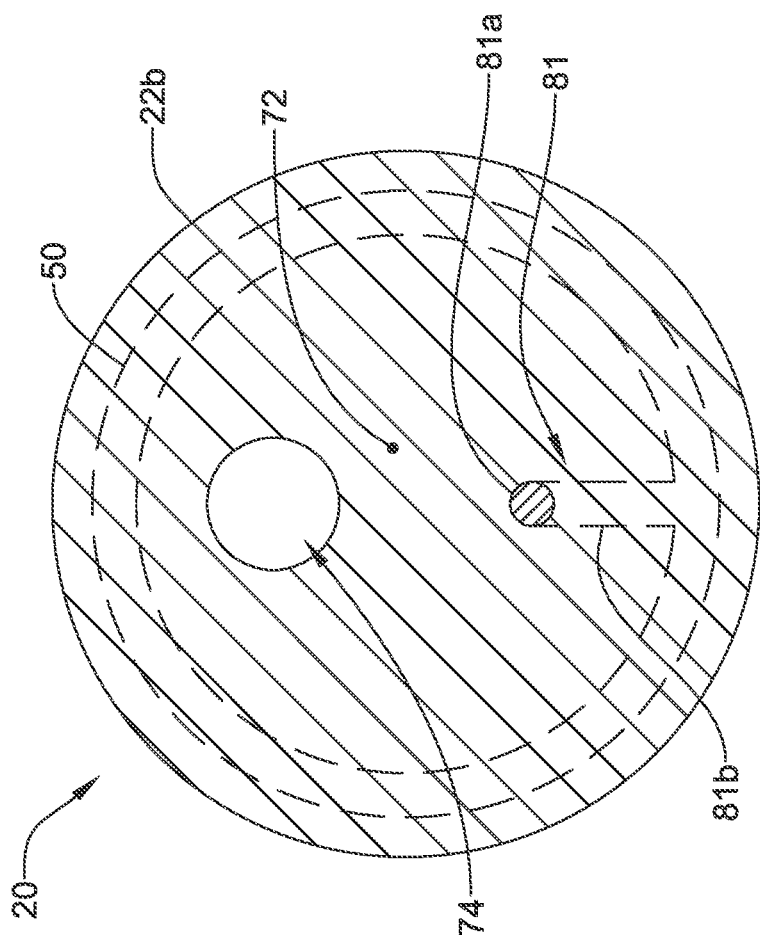
FIG. 4 is a schematic cross-sectional view taken along line 4-4 in FIG. 3.

FIG. 4 depicts a schematic cross-sectional view taken along line 4-4 in FIG. 3 and extending through the second portion 22b of the housing 22, a guide wire lumen 74 of the housing 22 (e.g., as discussed in greater detail below), the conductor 72 and the proximally extending portion 81b of the tail 81. The helical coil portion of the fixation member 50, the distal tip 57 of the fixation member 50, and the radial extending portion 81a of the tail 81 have been added to the schematic cross-sectional view of FIG. 4 in broken lines to indicate the respective locations of the components of the leadless pacing device 20 and to indicate these components would not typically be seen in the cross-section taken along line 4-4 of FIG. 3. Other components that may be seen in the cross-section taken along line 4-4 of FIG. 3 but not shown in FIG. 4, have been removed for clarity purposes.

In some cases, one or more of the radially extending portion 81a of the tail 81 and the proximally extending portion 81b of the tail 81 may be located at a circumferential position circumferentially aligned with the circumferential position of the distal tip 57 of the fixation member 50, or otherwise at another predetermined angular orientation from the circumferential position of the distal tip 57. Such alignment of one or both of the radially extending portion 81a and the proximally extending portion 81b with the distal tip 57 may facilitate positioning the distal tip 57 for penetration into myocardial tissue adjacent the coronary sinus 15 of a patient by providing radiopaque components of the leadless pacing device 20 with various dimensions that may be in a known position relative to the distal tip 57 and that may be viewable in images of the patient.

Figure 5:
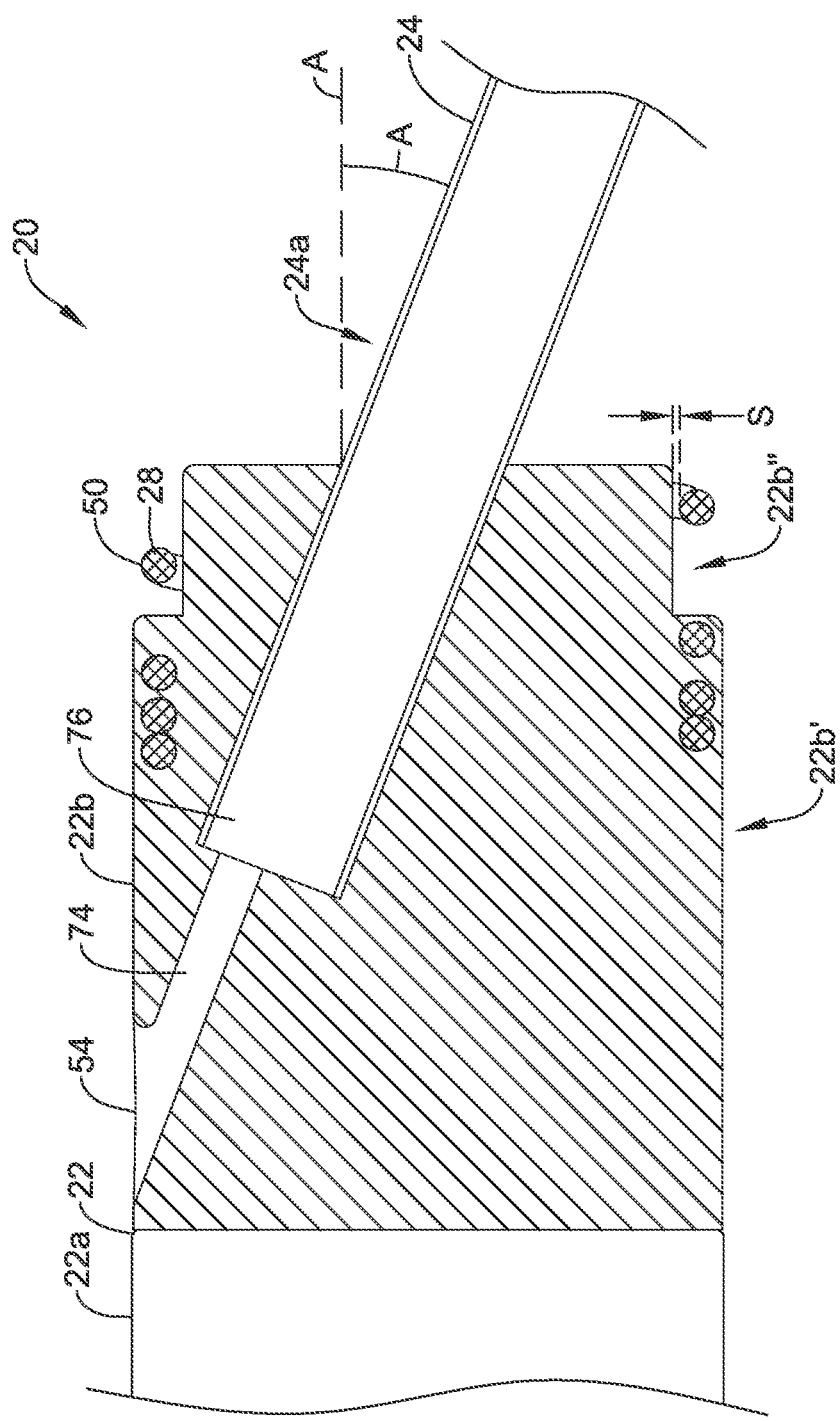
FIG. 5 is a cross-sectional side view of a distal portion of an example implantable leadless pacing device.

FIG. 5 depicts a partial schematic cross-sectional view of the second portion 22b of the housing 22 and a proximal end 24a of the distal extension 24, where the first portion 22a of the housing 22 is not depicted in cross-section. As seen in FIG. 5, the guide wire port 54 in a side of the second portion 22b of the housing 22 is at a proximal end of a guide wire lumen 74 formed through the second portion 22b of the housing 22. The guide wire lumen 74 may extend through the second portion 22b of the housing 22 to a proximal end of the guide wire lumen 76 of the distal extension 24, where the lumen 76 of the distal extension 24 is in communication with the guide wire lumen 74. The guide wire port 54, the guide wire lumen 74, and the guide wire lumen 76 extending through the distal extension 24 may form a passage for receiving a guide wire to facilitate the leadless pacing device 20 tracking along a guide wire to a target location. In some cases, the leadless pacing device 20 may track over a guide wire using a rapid exchange technique, where a wire is back-loaded through a distal guide wire port in the distal extension 24 (such as at the distal end of the distal extension 24) that is in communication with the guide wire lumen 76 of the distal extension 24 and threaded through the guide wire lumen 76 of the distal extension 24, the guide wire lumen 74, and the guide wire port 54. Other guide wire tracking techniques may be utilized.

The guide wire lumen 74 extending through the second portion 22b of the housing 22 may be formed in any manner. In one example and when the second portion 22b may be formed by an over molding process, a core material may be inserted into the over mold, the distal extension 24 may be positioned in the over mold so as to be aligned with the core material and extending from the over mold at an oblique angle A with respect to line A, the molding material (e.g., urethane resin, silicon, and/or other biocompatible molding material suitable for over molding processes) may be applied, and once the over mold material sets, the core material may be removed from the over mold material to form the guide wire port 54 and the guide wire lumen 74 in communication with the guide wire lumen 76 of the distal extension 24. Such positioning of the guide wire port 54 and the guide wire lumen 74 in the second portion 22b of the housing 22 may facilitate hermetically sealing the components of the first portion 22a of the housing 22 within the first portion 22a and creating an overall guide wire lumen with a smooth transition between the guide wire lumen 74 and the guide wire lumen 76.

The guide wire port 54 may be formed along any portion of the housing 22. As shown in FIG. 5, the guide wire port 54 may be located between a proximal end of the second portion 22b of the housing 22 and the second electrode 28 positioned within the second portion 22b of the housing 22. In some cases, the guide wire port 54 may be formed at a circumferentially opposite side of the housing 22 from a location of a distal tip of the fixation member 50, but this is not required in all cases. Such a configuration of the guide wire port 54 and the distal tip of the fixation member 50 relative to one another may facilitate contact between the first and second electrodes 26, 28 and a target location within a patient's body. For example, a guide wire will want to follow a largest radius of curvature as possible and as the coronary sinus 15 of a patient extends around the heart 10, a guide wire inserted into the coronary sinus may naturally track along an outside wall of the coronary sinus (e.g., a wall opposite a wall of the coronary sinus forming a wall of a chamber of the heart 10) due to the guide wire being able to follow a radius of curvature larger than it would otherwise be able to follow. Thus, in the example, when the guide wire port 54 is located on an opposite side of the second portion 22b of the housing 22 from the distal tip of the fixation member 50 and the fixation member 50 extends a full revolution around the second portion 22b of the housing 22, the guide wire port 54 may be adjacent a wall of the coronary sinus 15 spaced from the wall of the coronary sinus 15 that forms a chamber of the heart 10 and as a result, the first and second electrodes 26, 28 may be positioned adjacent the wall of the coronary sinus 15 that forms a wall of a chamber of the heart 10 and may be in improved contact with the wall of the coronary sinus 15 that forms the wall of the chamber of the heart 10 than if the guide wire port 54 were positioned elsewhere.

As depicted in FIG. 5, the second portion 22b of the housing 22 may have a first diameter proximal portion 22b' having a first diameter and a second diameter distal portion 22b'' having a second diameter. Although not required, in some cases, for example as depicted in FIG. 5, the second diameter of the second diameter portion 22b'' may be less than the first diameter of the first diameter portion 22b'. In some instances the first diameter of the proximal portion 22b' may be substantially equal to the diameter of the first portion 22a of the housing 22. Example diameters of the first diameter include, but are not limited to, diameters in a range of about 6.0 mm (0.236 inches) to about 7.0 mm (0.276 inches), diameters less than or less than about 0.393 inches (e.g., about 30 French (Fr)) and/or other suitable diameters. In one example, the first diameter may be about 6.5 mm (0.256 inches). Example diameters of the second diameter include, but are not limited to, diameters in a range of about 4 mm (0.157 inches) to about 6 mm (0.236 inches), about 4.5 mm (0.177 inches) to about 5.5 mm (0.217 inches), about 5.0 mm (0.197 inches) to about 5.2 mm (0.206), diameters less than or less than about 5.7 mm (0.226 inches) and/or other suitable diameters. In an example where the first diameter may be about 6.5 mm (0.256 inches) and the second diameter may be about 5.2 mm (0.206 inches).

The fixation member 50 may extend at least partially around and be spaced away from an outer circumference of the second portion 22b of the housing 22 (e.g., at last partially around and spaced away from the second diameter distal portion 22b'' or other suitable portion of the second portion 22b of the housing 22). In some cases, when the fixation member 50 extends at least partially around an outer circumference of the second portion 22b of the housing 22, a gap or space S may be located between a circumference at an inner diameter of the fixation member 50 and the outer circumference of the distal portion of the second portion 22b. Although not required, the fixation member 50 may be configured such that the space S spans a distance suitable for receiving a portion of myocardial tissue radially between the second portion 22b of the housing 22 and the fixation member 50 while the fixation member 50 is engaging the myocardial tissue. Example distances the space S may span include, but are not limited to, a distance between approximately 0.001 inches to approximately 0.006 inches, approximately 0.002 inches to approximately 0.004 inches, or other suitable distances. In one instance, the space S may span a distance of approximately 0.003 inches.

Figure 6:
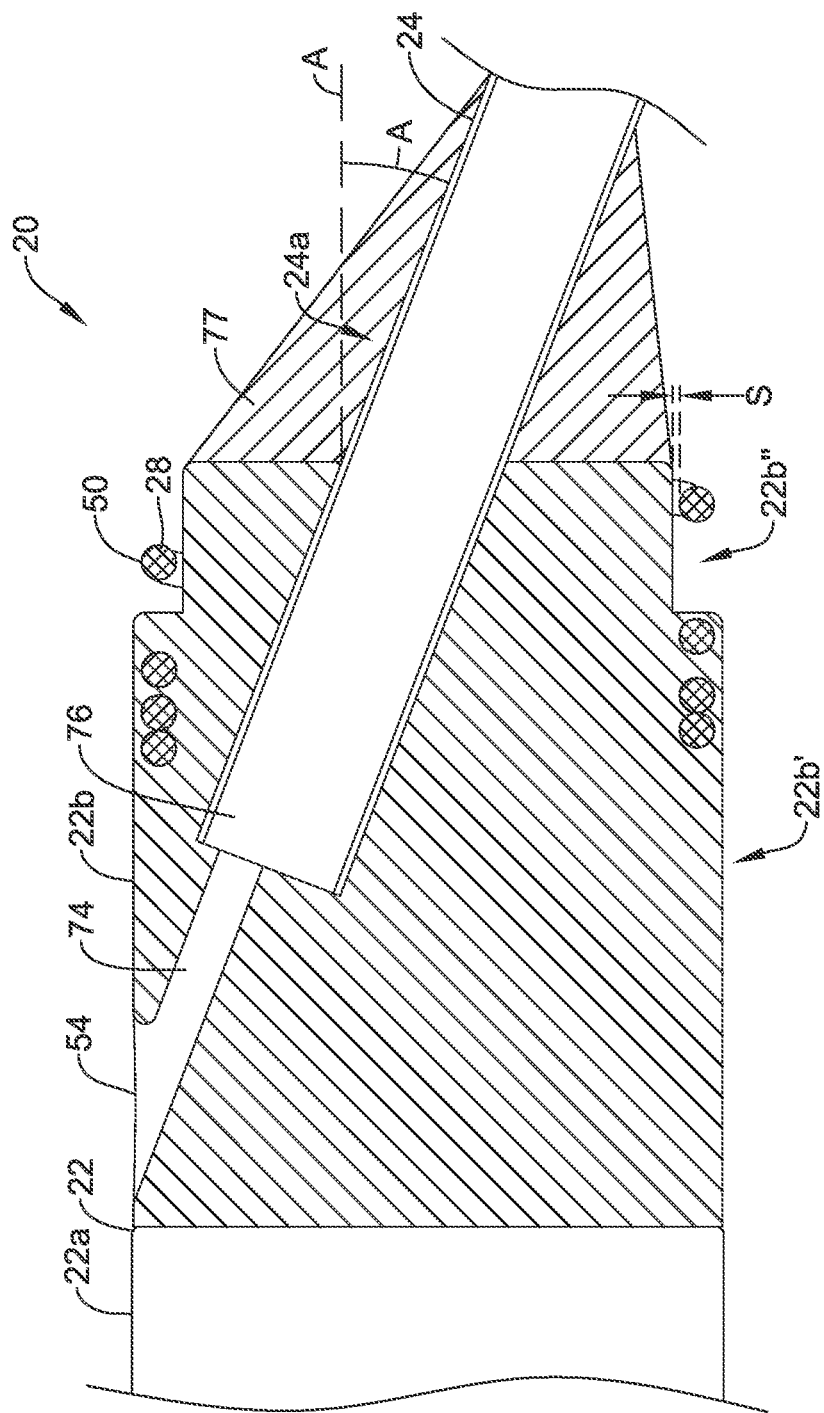
FIG. 6 is a cross-sectional side view of a distal portion of an example implantable leadless pacing device having a strain relief feature.

FIG. 6 depicts a partial schematic cross-sectional view of the second portion 22b of the housing 22 and a proximal end 24a of the distal extension 24 similar to the schematic cross-sectional view depicted in FIG. 5, but with a strain relief 77 distally extending from a distal end of the second portion 22b of the housing 22 along an outer surface of the distal extension 34. The strain relief 77, when included in the leadless pacing device 20, may have a flexibility that changes along its length and may facilitate transitioning from the more rigid second portion 22b of the housing 22 to the less rigid distal extension 24. Such stiffness transition may facilitate navigating a tortuous vasculature of a patient.

In some cases, the strain relief 77 may have a distally extending taper and may extend a suitable distance distally from the second portion 22b of the housing 22. In one example, the strain relief 77 may extend about 1.0 to about 4.0 centimeters (cm) from the second portion 22b of the housing 22, extend 1.0 to 3.5 cm from the second portion 22b of the housing 22, and/or extend other suitable distances. Further, in addition to or as an alternative to the strain relief 77 including a taper, the strain relief 77 may include a spring, a material or materials having desired durometers or durometer gradient, and/or other mechanism for creating different flexibilities along the length of the strain relief 77. In one example, the strain relief 77 may include one or more materials along its length, where the one or more materials may have different durometers to create a transition in stiffness, or durometer gradient, along the length of the strain relief 77.

As depicted in FIG. 6, the strain relief 77 may be positioned asymmetrically about the distal extension 34 to facilitate rotation of the leadless pacing device 20, including the distal extension 24. Although an example of an asymmetrically configured strain relief 77 is depicted in FIG. 6, another example of an asymmetrically configured strain relief 77 may include a strain relief 77 that covers only a single half or other suitable portion of a circumference of the distal extension 24 such that the strain relief 77 surrounds less than an entirety of the circumference of the distal extension 24 (e.g., cover a half or portion of the distal extension 24 that is angled toward the second portion 22b of the housing 22). Alternatively, the strain relief 77 may be positioned symmetrically about the distal extension 34. In other instances, the strain relief 77 may be omitted.

The strain relief 77 may be formed from one or more components and/or one or more suitable materials. In one example, the strain relief 77 may be formed from a silicone or other suitable material. In some cases, the material used to form the strain relief 77 may be receptive to indicia, such as a serial number, company logo, and/or other suitable indicia that may or may not be required to be provided on the leadless pacing device 20. Additionally or alternatively, the strain relief 77 may be formed while forming the second portion 22b of the housing 22 with an over mold process. In such cases, the strain relief 77 may be formed as part of the second portion 22b of the housing 22. Alternatively, the strain relief 77 may be formed from a component that is separate from the material forming the second portion 22b of the housing 22.

FIGS. 7-13 depict various schematic views of the illustrative fixation member 50 in a helical coil configuration having different portions of the helical coil exposed for making electrical contact with tissue of a patient's heart. In some cases, the exposed portions of the helical coil may be defined by coating portions of the helical coil that are to be unexposed (e.g., not electrically conductive). In some case, the helical coil may be formed from an electrically conductive material and portions of the helical coil that are to be unexposed may be covered with a dielectric material or other suitable insulating material. Examples of such materials include, but are not limited to, poly(p-xylene) polymers (e.g., Parylene, Parylene C, etc.), titanium nitride, iridium oxide (IrOx), aluminum oxide, and/or other suitable dielectric materials. In some cases, portions of the helical coil that are to receive a coating material may be surface modified (e.g., etched, sand blasted, and/or other suitable surface modification) to facilitate the coating material adhering to the metal of the helical coil forming the fixation member 50. Further, although the FIGS. depict the material forming the fixation member 50 as a rounded wire with the distal penetrating tip 57, the material forming the fixation member 50 may be a flat wire with a distal penetrating tip and/or may have one or more other suitable configurations.

In some cases, a mask may be formed over portions of the fixation member 50 that are to be exposed (e.g., the exposed portions 51 discussed below with respect to FIGS. 7-13) for making electrical contact with tissue of a patient's heart (e.g., portions of the fixation member 50 forming the second electrode 28), such that when the fixation member 50 receives the coating material, the masked portions of the fixation member 50 are left uncovered with the coating material or otherwise exposed to form the second electrode 28 on or otherwise along the fixation member 50. In some cases, the portions of the fixation member 50 exposed for making electrical contact with the tissue of a patient's heart may include any suitable total area of the fixation member 50. For example, the portions of the fixation member 50 exposed for making electrical contact with the tissue of a patient's heart may have a total area in a range of about 0.078 inches to about 0.315 inches, a range of about 0.137 inches to about 0.158 inches, and/or other suitable total areas of the fixation member 50.

Figure 7:
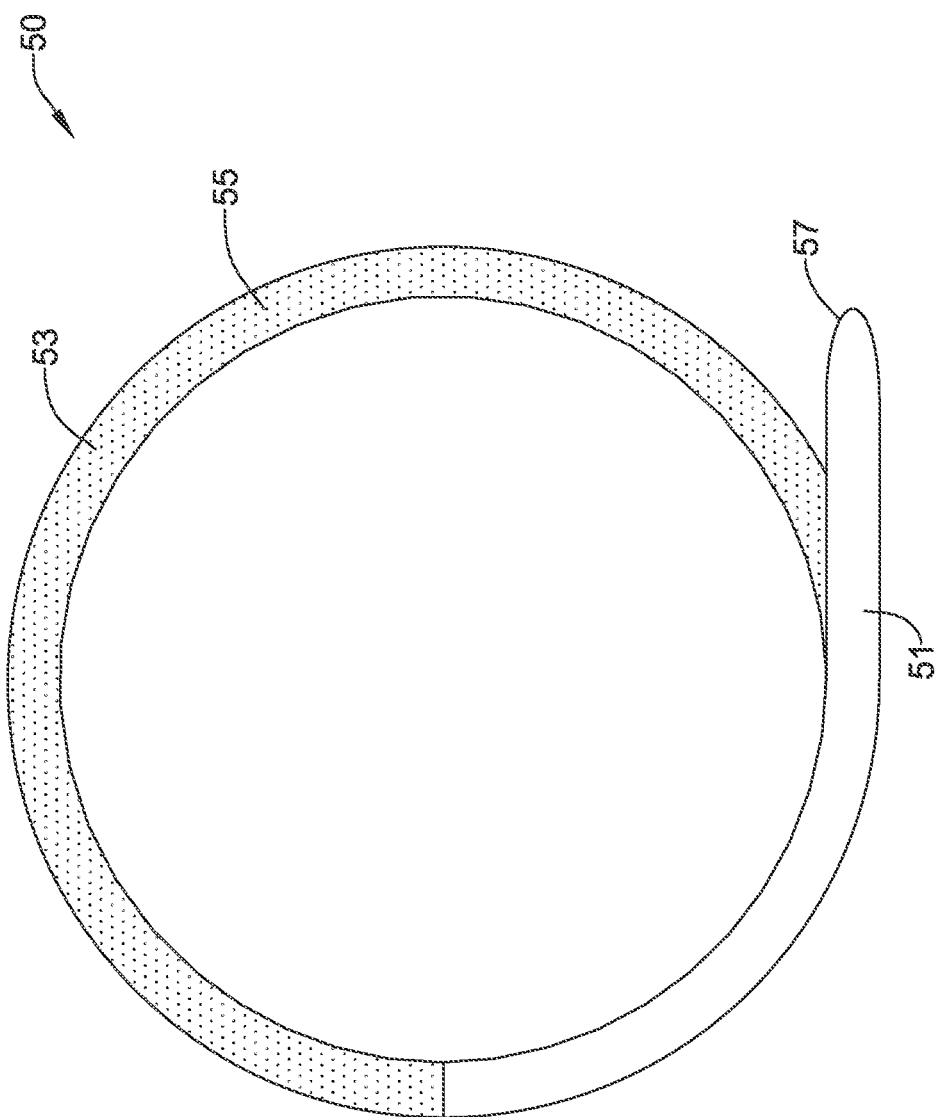
Figure 8:
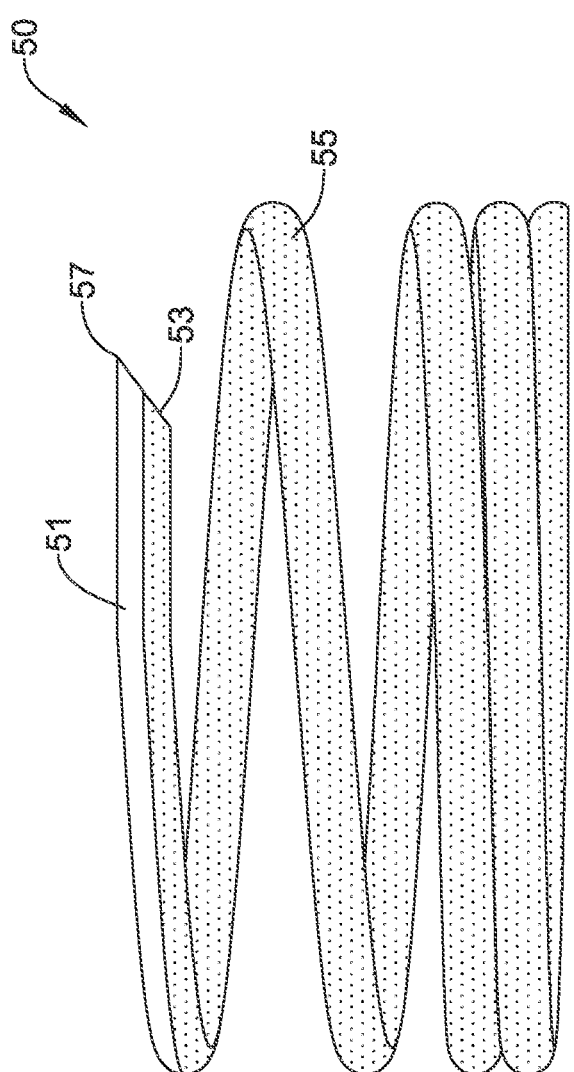

FIG. 7 is a schematic top view and FIG. 8 is a schematic side view depicting the fixation member 50 with the distal tip 57 and having an exposed portion 51 at a last quarter of a revolution of the helical coil forming the fixation member 50, where the remaining portions of the helical coil may be an unexposed portion 53 covered in a layer 55 of insulating and/or dielectric material. The distal tip 57 may be formed at a distal end of the helical coil that has been straightened to facilitate the distal tip 57 penetrating a wall of a patient's heart that extends along a lateral side of an implanted leadless pacing device 20. The distal tip 57 may have a sharp tip and/or edges configured to puncture and engage a wall of a patient's heart. The exposed portion 51 in FIGS. 7 and 8 extend over a top half of an outer surface of the material forming the helical coil. The exposed portion 51, however, at the last quarter revolution of the helical coil may extend over a different half of or other portion of an outer surface of the material forming the last quarter revolution of the helical coil such that the exposed portion 51 in FIGS. 7 and 8 may be rotated 90 degrees, 180 degrees, 270 degrees, and/or other suitable amounts.

Figure 9:
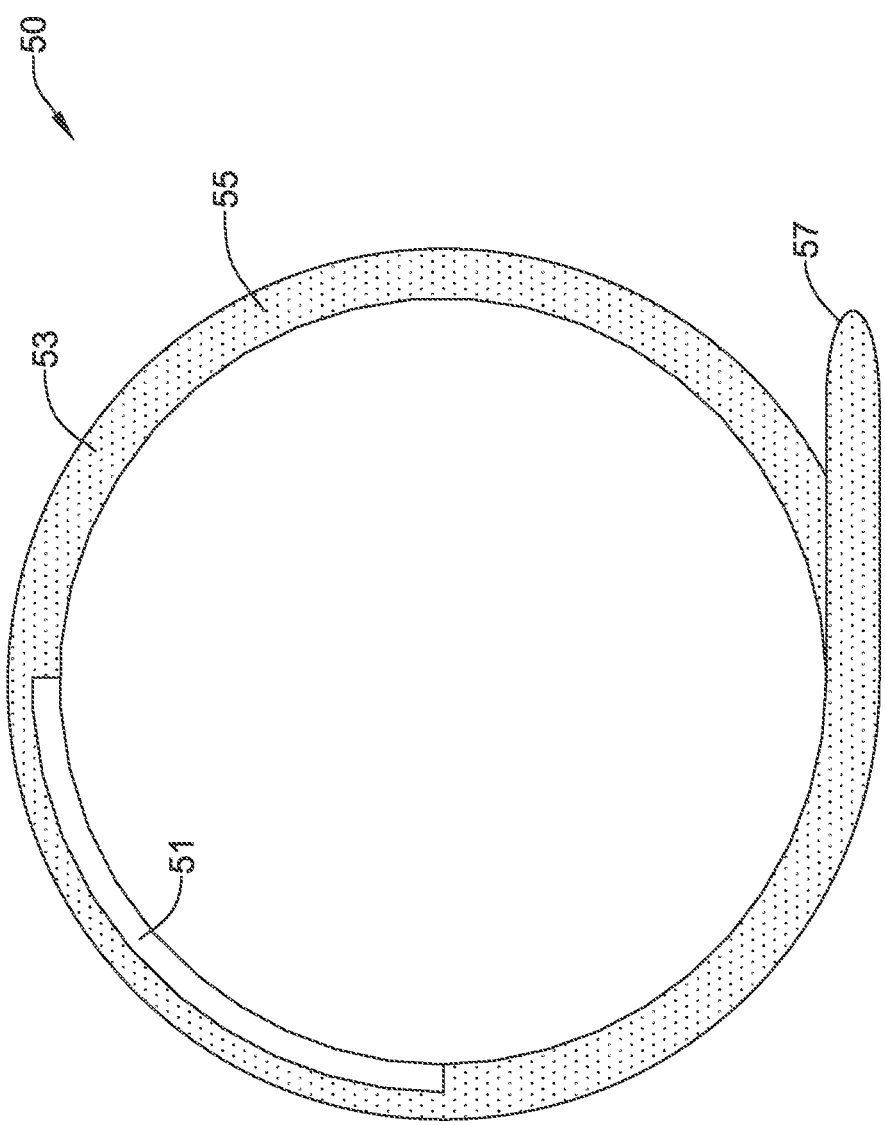
Figure 10:
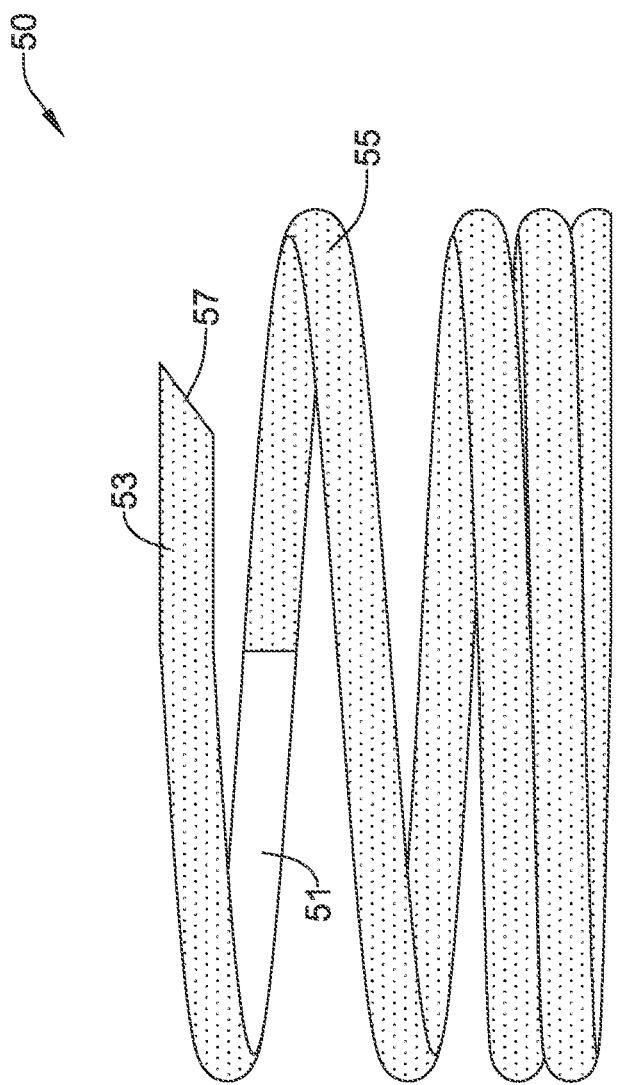

FIG. 9 is a schematic top view and FIG. 10 is a schematic side view depicting the fixation member 50 with the distal tip 57 and having an exposed portion 51 at a second to last quarter of a revolution of the helical coil forming the fixation member 50, where the remaining portions of the helical coil may be the unexposed portion 53 covered in the layer 55 of insulating and/or dielectric material. The exposed portion 51 in FIGS. 9 and 10 extend over an inner side half of an outer surface of the material forming the helical coil. The exposed portion 51, however, at the second to last quarter revolution of the helical coil may extend over a different half of or other portion of an outer surface of the material forming the second to last quarter revolution of the helical coil such that the exposed portion 51 in FIGS. 9 and 10 may be rotated 90 degrees, 180 degrees, 270 degrees, and/or other suitable amounts.

Figure 11:
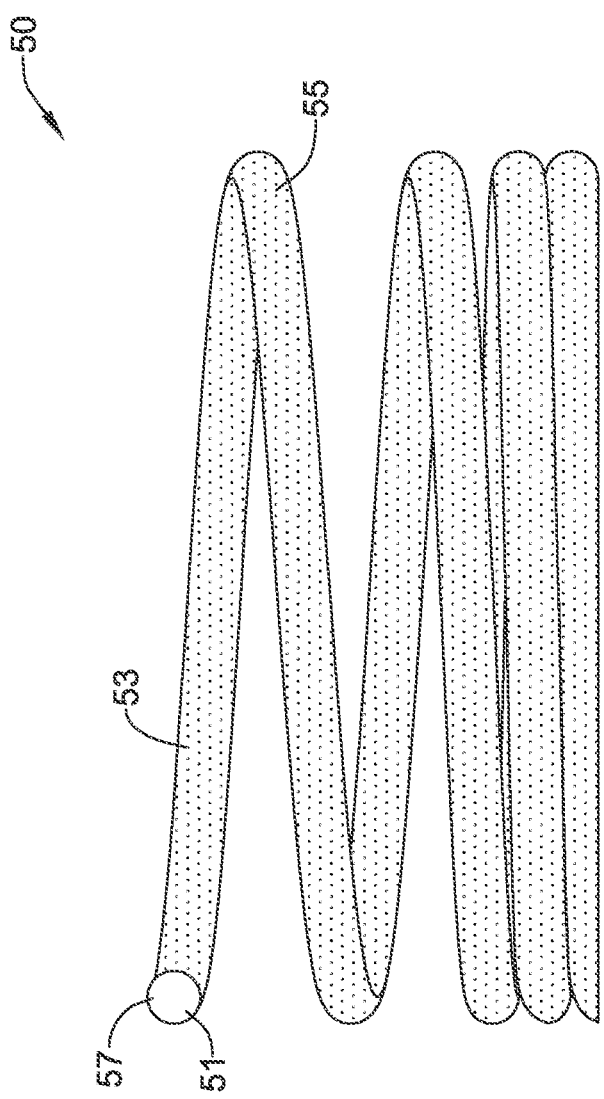

FIG. 11 is a schematic side view depicting the fixation member 50 with the distal tip 57 and having an exposed portion 51 at the distal tip 57 of the fixation member 50. In FIG. 11, all portions of the helical coil forming the fixation member 50 other than the distal tip 57 may be unexposed portions 53 of the fixation member 50 covered with a layer 55 of insulating and/or dielectric material.

Figure 12:
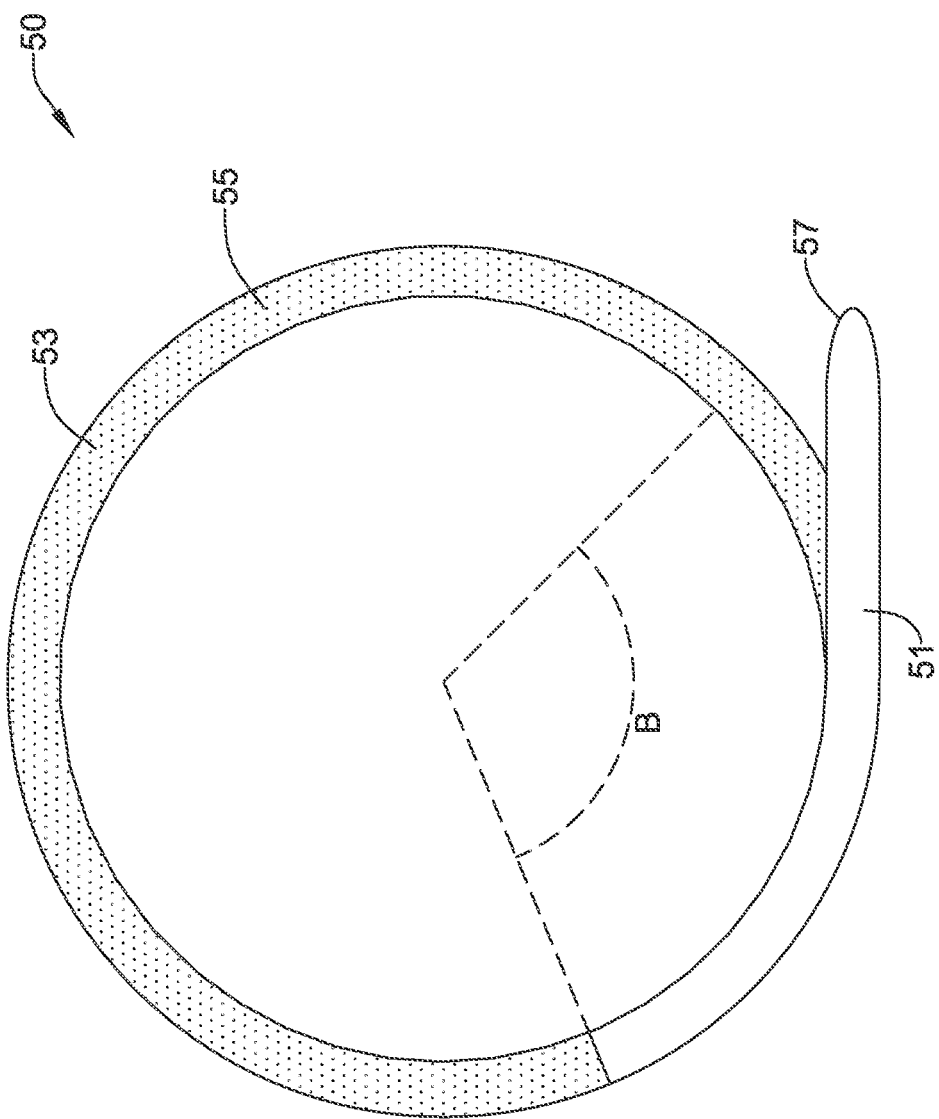

FIG. 12 is a schematic top view depicting the fixation member 50 with the distal tip 57 and having an exposed portion 51 defined by an angle B, where angle B may extend from the distal tip 57 of the fixation member 50 (e.g., as shown in FIG. 12, where angle B extends from a would-be radial location of the distal tip 57 if the material forming the helical coil of the fixation member 50 had not been straightened out) to a location proximal of the distal tip 57. Angle B may have any suitable value. In some instances, angle B may be in the range of about 5 to 45 degrees, about 5-60 degrees, about 5-90 degrees, about 5-180 degrees, or about 5-360 degrees, for example. In some cases, angle B may be determined based, at least in part, on a desired size of the exposed portion 51 and/or a desired size of an unexposed portion 53 covered with a layer 55 of insulating and/or dielectric material. Although angle B is depicted as having one end at the distal tip 57, this is not required and the angle B may extend between any two radial cross-sections along the helical coil forming the fixation member 50. Further, the exposed portion 51 in FIG. 12 may extend over a top half of an outer surface of the material forming the helical coil. However, the exposed portion 51 at angle B of the helical coil may extend over a different half of or other portion of an outer surface of the material forming the helical coil at angle B such that the exposed portion 51 in FIG. 12 may be rotated 90 degrees, 180 degrees, 270 degrees, and/or other suitable amounts.

FIG. 13 is a schematic top view depicting the fixation member 50 with the distal tip 57 and having exposed portions 51 at various intervals defined by angle C and angle D, where angle C may define a width of the exposed portions and angle D may define a width of the unexposed portions 53 covered with a layer 55 of insulating and/or dielectric material. Angle C and angle D may have any suitable values including, but not limited to, the same values or different values. In some instances, angle C and/or angle D may be in the range of about 2 to 10 degrees, about 2 to 30 degrees, about 2 to 45 degrees, about 5 to 10 degrees, about 10 to 30 degrees, or about 10 to 45 degrees. In some cases, angle C may be determined based, at least in part, on a desired size of the exposed portion 51 and angle D may be determined based, at least in part, on a desired size of the unexposed portion 53. In FIG. 13, the exposed portions 51 and the unexposed portions 53 alternate through a full revolution of the helical coil forming the fixation member 50, but may alternate any other suitable radial distance around the helical coil. Further, the exposed portions 51 in FIG. 13 may extend over a top half of an outer surface of the material forming the helical coil. However, the exposed portions 51 of the helical coil may extend over a different half of or other portions of an outer surface of the material forming the exposed portions 51 of the helical coil defined by angle C such that the exposed portion 51 in FIG. 13 may be rotated 90 degrees, 180 degrees, 270 degrees, and/or other suitable amounts.

FIG. 14 is a schematic partial cross-sectional view of the right atrium 11, the left atrium 12, and the coronary sinus 15, where the leadless pacing device 20 is inserted into the coronary sinus 15 defined, at least in part by a portion 82 of a wall defining the coronary sinus 15 that is spaced from walls defining atriums of the heart 10, a wall 84 of the left atrium 12, and a wall 85 of the right atrium 11. In one example, as depicted in FIG. 14, the fixation member 50 may engage tissue of the wall 84 forming the left atrium 12 such that the leadless pacing device 20 is in good electrical contact with a wall defining at least one chamber of the heart 10. In the example, when the fixation member 50 is engaging the wall 84 forming the left atrium 12, the second electrode 28 that may be supported by or formed from the fixation member 50 may be in good electrical contact with tissue forming the wall 84 of the left atrium 12 due to the fixation member 50 being inserted into such tissue and the first electrode 26 that may be supported by or formed from the first portion 22a of the housing 22 may be in good electrical contact with tissue forming the wall 85 of the right atrium 11 as a result of the engagement of the fixation member 50 with tissue of the heart 10. Further, the distal extension 24 may be inserted into a vessel extending from the coronary sinus 15 while the fixation member 50 is engaging tissue of the heart 10.

Figure 15B:
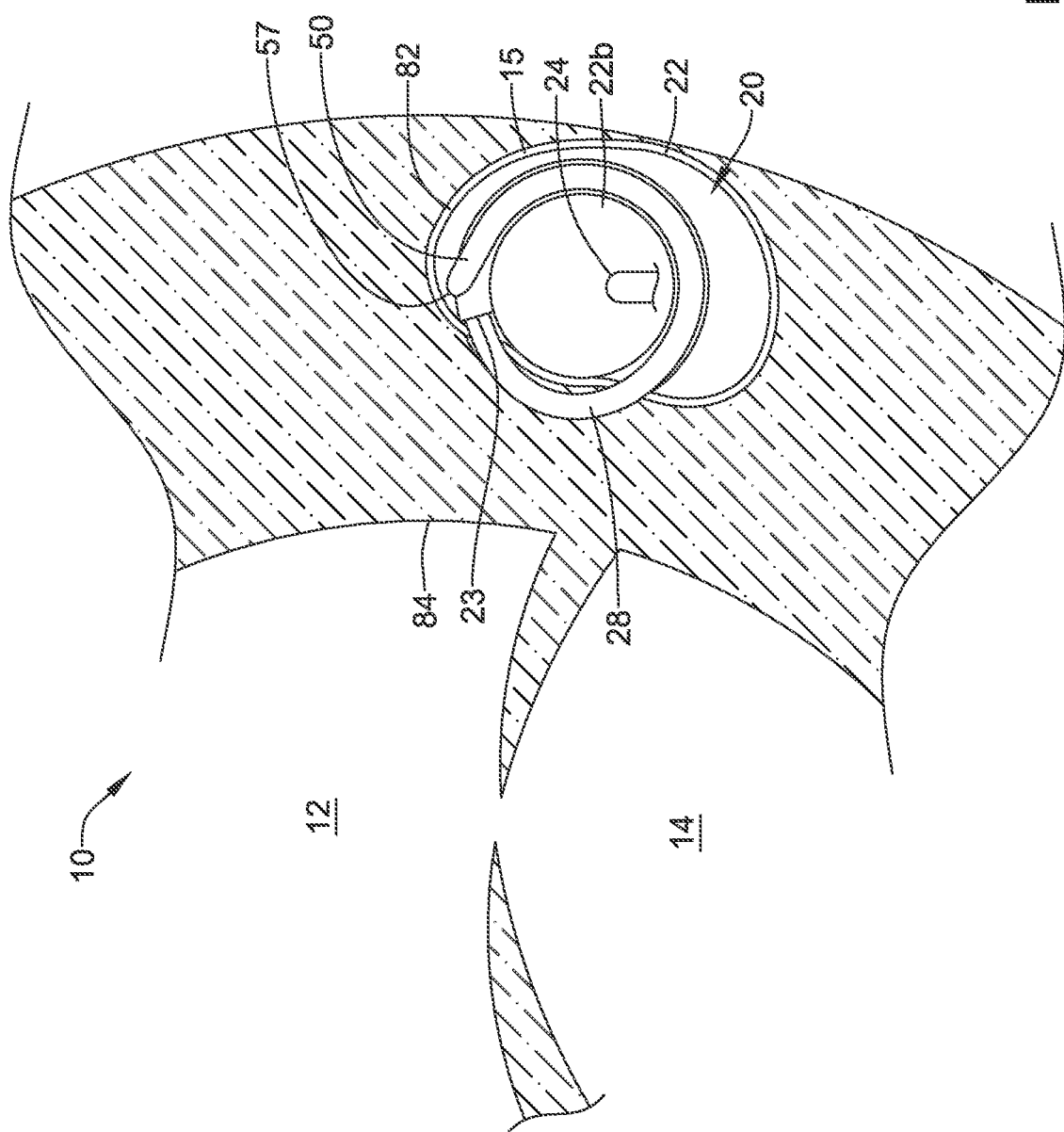

FIGS. 15A and 15B depict schematic end views of the leadless pacing device 20 positioned within the coronary sinus 15 of the heart 10, where the leadless pacing device 20 is viewed from a distal end view and the heart 10 and the coronary sinus 15 are in cross-section. Although the wall defining the coronary sinus 15 is shown in cross-section, the wall defining the coronary sinus 15 is not shown with hatching for clarity purposes. FIG. 15A schematically depicts the leadless pacing device 20 within the coronary sinus 15 prior to the fixation member 50 engaging the wall 84 defining the left atrium 12. Further, at a location at which the fixation member 50 extends from the second portion 22b of the housing 22, the second portion 22b of the housing 22 may define a stop 23 configured to limit insertion of the fixation member 50 in tissue to a predetermined insertion amount (e.g., limit rotation of the leadless pacing device 20 while the fixation member 50 is engaging tissue). The predetermined insertion amount may be substantially equal to a length of the fixation member 50 extending from the stop 23 to a distal tip of the fixation member 50. Although the stop 23 is depicted in FIGS. 15A and 15B as being formed from the housing 22 (e.g., the molded portions forming the second portion 22b of the housing 22), the stop 23 may be formed by a change in diameter or coiling of the fixation member 50 and/or configured from one or more other suitable components. In some cases, the stop 23 may be or may form a shoulder without a gradual incline such that the stop 23 prevents gradual entry and tearing or rupturing of a wall of the heart 10 if the leadless pacing device 20 were to be rotated farther than the predetermined amount. In one example, the stop 23 may be formed from the second portion 22b of the housing 22 or the fixation member 50 and form a substantially flat surface that may be generally perpendicular to a central axis running through a material (e.g., a wire material) forming the helical coil of the fixation member 50. However, in other instances the stop 23 may have a taper or gradually expanding width. Further, although the fixation member 50 is seen to extend a full revolution from the second portion 22b of the housing 22 and the stop 23 such that the predetermined rotational amount may be a full revolution of the leadless pacing device 20, more or less of the fixation member 50 may be exposed from the second portion 22b of the housing 22 such that the predetermined rotational amount may be more or less than a full revolution, respectively, as desired.

As viewed from the distal end of the leadless pacing device 20, the helical fixation member 50 may extend helically in a counter-clockwise direction to the distal tip 57. Thus, with the distal tip 57 of the fixation member 50 pointed toward a superior portion of the coronary sinus, counter-clockwise rotation of the leadless pacing device, viewed along the axis of the housing 22 toward the proximal end of the housing 22 from the distal end of the housing 22 will cause the distal tip 57 to engage the luminal surface of the coronary sinus 15 and penetrate into cardiac tissue (e.g., the left atrial muscle).

Furthermore, as shown in FIG. 15A, the distal tip 57 may extend radially outward of the outer diameter of the housing 22 to facilitate engagement of the distal tip 57 with cardiac tissue.

FIG. 15B depicts the leadless pacing device 20 positioned in the coronary sinus 15 and rotated approximately a full revolution relative to a radial position of the leadless pacing device 20 depicted in FIG. 15A. As the leadless pacing device 20 is rotated and the fixation member 50 engages the wall 84, the stop 23 may engage the wall 84 adjacent an entry point of the fixation member 50 to limit and/or stop continued rotational movement of the leadless pacing device 20. Further, as the fixation member 50 engages the tissue of the wall 84 a portion of the wall 84 may be squeezed or otherwise positioned between the fixation member 50 and a portion of the second portion 22b of the housing 22 about which the fixation member 50 extends when not engaging a wall of a patient's heart 10.

Figure 16:
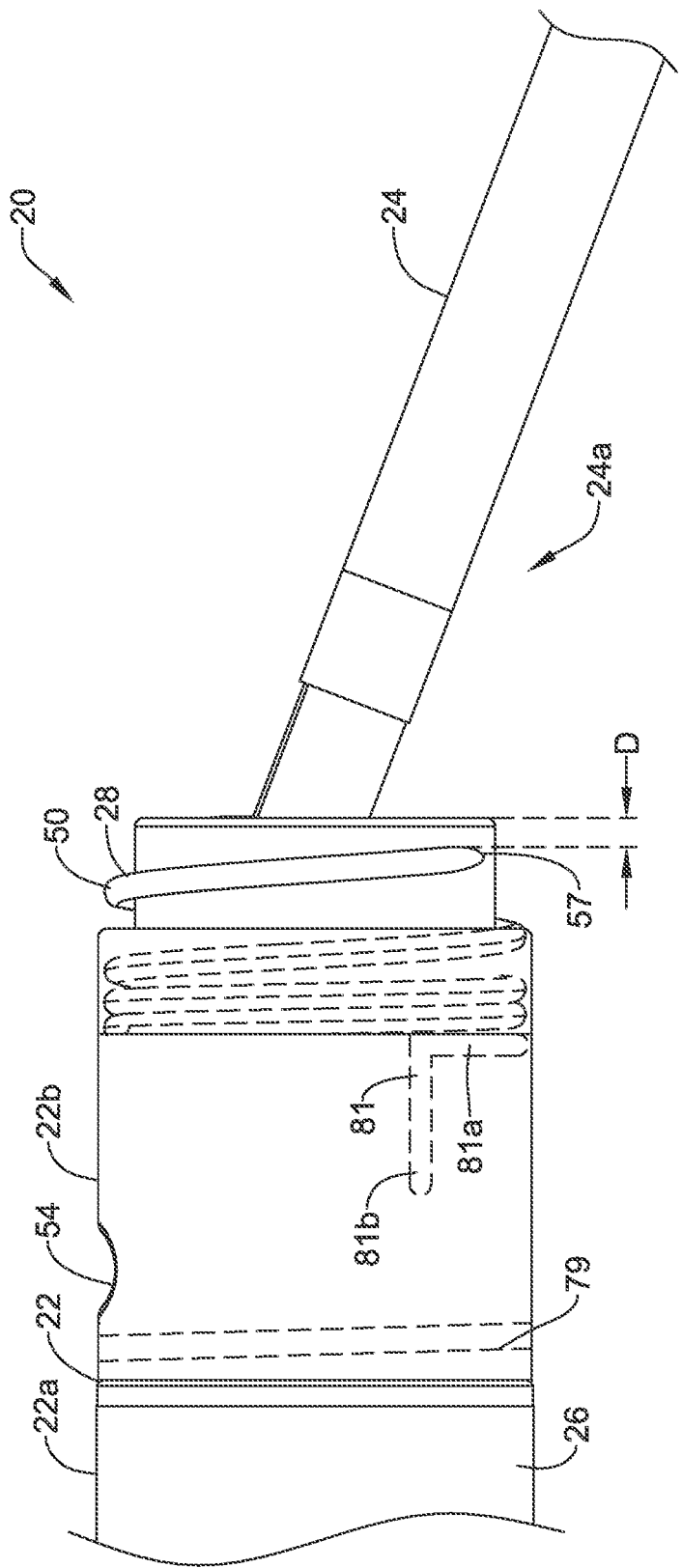
FIG. 16 is a side view of a distal end of an example implantable leadless pacing device having a communication wire.
Figure 17:
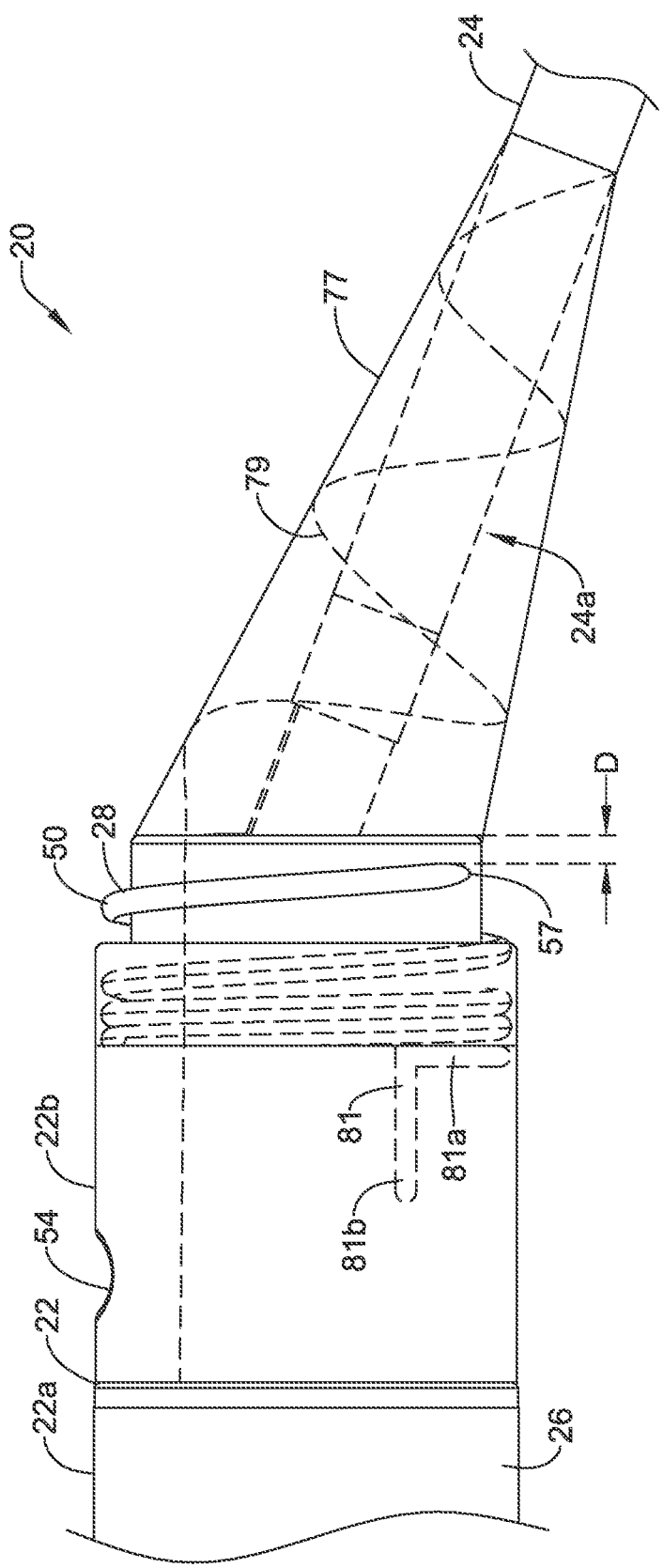
FIG. 17 is a side view of a distal end of an example implantable leadless pacing device having a communication wire at a strain relief feature.

FIGS. 16 and 17 depict schematic partial side views of the leadless pacing device 20 showing the second portion 22b of the housing 22, a proximal end 24a of the distal extension 24, and a communication wire 79 in communication with a conductor electrically connected to the electronics module within the first portion 22a of the housing 22. The communication wire 79 may be depicted in broken lines to indicate the wire may be embedded within material forming the second portion 22b of the housing 22. The communication wire 79 may be any suitable type of communication wire. In one example, the communication wire 79 may be an inductive communication antenna. The communication wire 79 may facilitate communication with one or more other electronic devices over a wireless protocol including, but not limited to, radio frequency (RF), near-field communications (NFC), Bluetooth, Bluetooth Low Energy (BLE), and/or other suitable wireless protocols. Further, although only a single communication wire 79 is depicted in FIGS. 16 and 17, more than a single communication wire 79 may be utilized to facilitate communicating over one or more communication protocols or no communication wire may be provided.

As depicted in FIG. 16, the communication wire 79 may be wrapped around and/or within the second portion 22b of the housing 22. When the communication wire 79 is supported by the second portion 22b of the housing 22, the communication wire 79 may be at least partially embedded in the housing 22 during a forming process (e.g., an over molding process or other suitable forming process) forming the second portion 22b of the housing 22. Alternatively or in addition, the communication wire 79 may be positioned at and/or secured in the second portion 22b of the housing 22 in one or more other suitable manners.

As depicted in FIG. 17, the communication wire 79 may be extend around the distal extension 24 within the strain relief 77, when the strain relief 77 is included in the leadless pacing device 20. When the communication wire 79 is supported by the strain relief 77, the communication wire 79 may be at least partially embedded in the strain relief 77 during a forming process (e.g., an over molding process or other suitable forming process) forming the strain relief 77 around the distal extension 24. Alternatively or additionally, the communication wire 79 may be wrapped around the proximal end 24a (e.g., with at least a portion of the proximal end 24a depicted as broken lines in FIG. 17 indicating such portions may be covered by the strain relief 77) and then the strain relief 77 may be applied thereto to protect the communication wire 79. When the communication wire 79 is embedded in or otherwise within the strain relief 77, the communication wire 79 may act as a reinforcement in the strain relief 77 and when the communication wire 79 is wrapped around the proximal end 24a of the distal extension 24, the communication wire 79 act as a reinforcement for the distal extension. Further, the communication wire 79 may be positioned at and/or secured in the strain relief 77 and/or the distal extension 24 in one or more other suitable manners.

In some cases, the leadless pacing device 20 may include a drug eluting component or feature configured to release one or more drugs over time. The time-released drug may be any suitable drug including, but not limited to, a drug suitable for blocking cell proliferation so as to prevent fibrosis, a drug suitable for encouraging cell proliferation, and/or other suitable drug. One example of a drug eluting component or feature may include, but is not limited to, a drug collar configured to elute a drug suitable for blocking cell proliferation so as to prevent fibrosis. An example of a drug to be eluted is a dexamethasone acetate and/or other similar or different suitable drugs. FIGS. 18-21 depict various schematic views of the leadless pacing device 20 including a drug collar 89. Alternatively or additionally, the drug eluting component or feature may take on one or more other suitable configurations including, but not limited to, an adhesive with which the drug to be eluted has been mixed, applied to a portion of the leadless pacing device 20, and cured.

Figure 18:
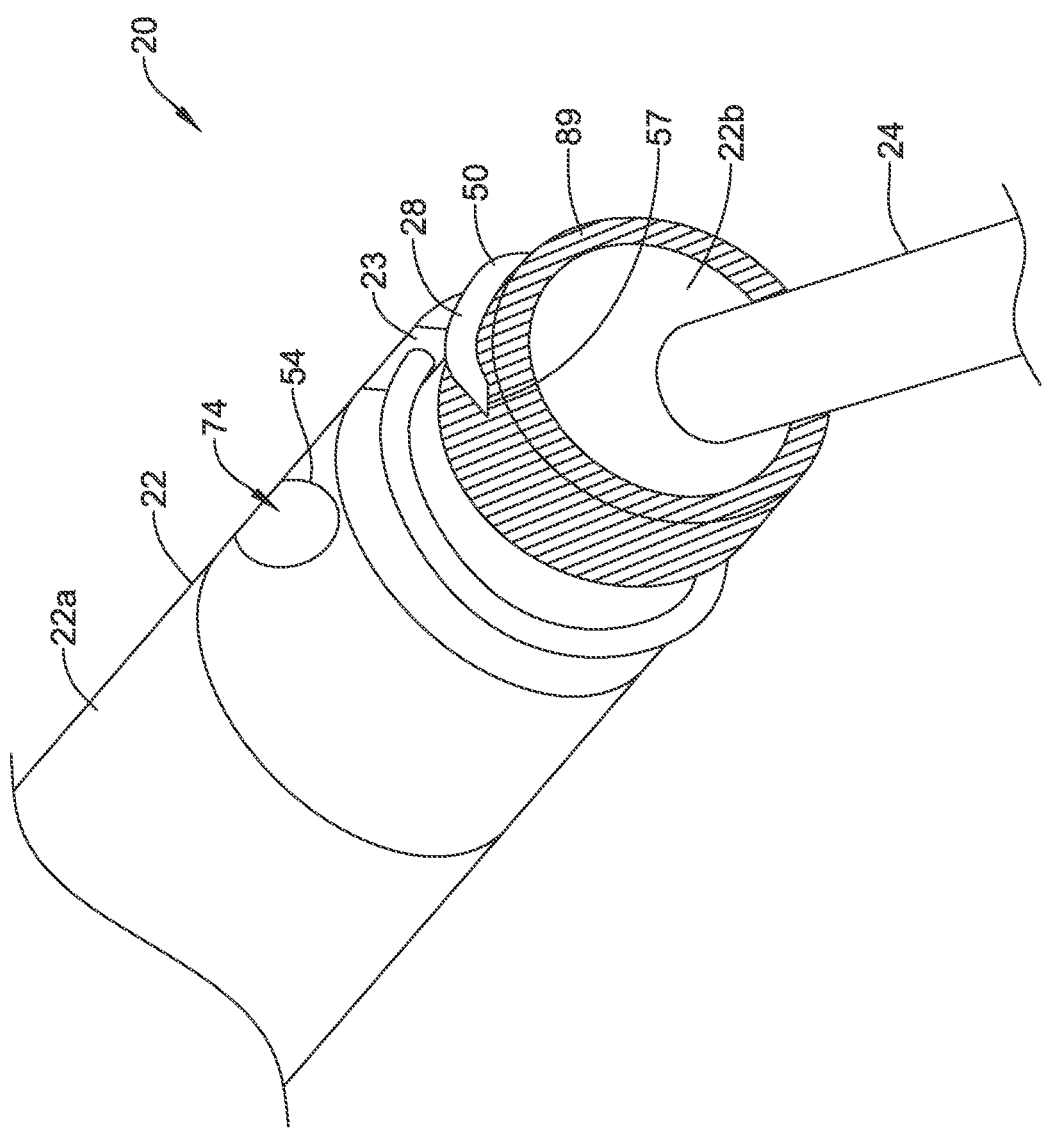
FIG. 18 is a perspective view of a distal end of an example implantable leadless pacing device having a drug collar.

FIG. 18 depicts a schematic perspective view of the leadless pacing device 20 having the drug collar 89 extending around the second portion 22b of the housing 22. In some cases, the drug collar 89 may be configured on the second portion 22b of the housing 22 such that the fixation member 50 extends from the stop 23 of the second portion 22b of the housing 22 and at least partially around the drug collar 89. When the drug collar 89 is so positioned, the fixation member 50 may be configured to trap tissue from a wall of a patient's heart between the fixation member 50 and the drug collar 89. In some cases, the drug collar may be configured to prevent or mitigate cell growth at or around the fixation member 50 and/or the housing 22 when the leadless pacing device 20 is implanted. In one example, the drug collar 89 may be configured on the leadless pacing device 20 so as to be adjacent a site of trauma as the fixation member 50 enters into tissue of a patient's heart (e.g., the drug collar 89 may be configured on the housing 22 so as to be adjacent a puncture point on a patient's heart wall caused by the fixation member 50 entering the heart wall).

In some cases, the drug collar 89 may be formed in a single-piece ring, as shown in FIG. 18. Alternatively, the drug collar may be formed from one or more portions adjacent to one another or spaced from one another.

Figure 19:
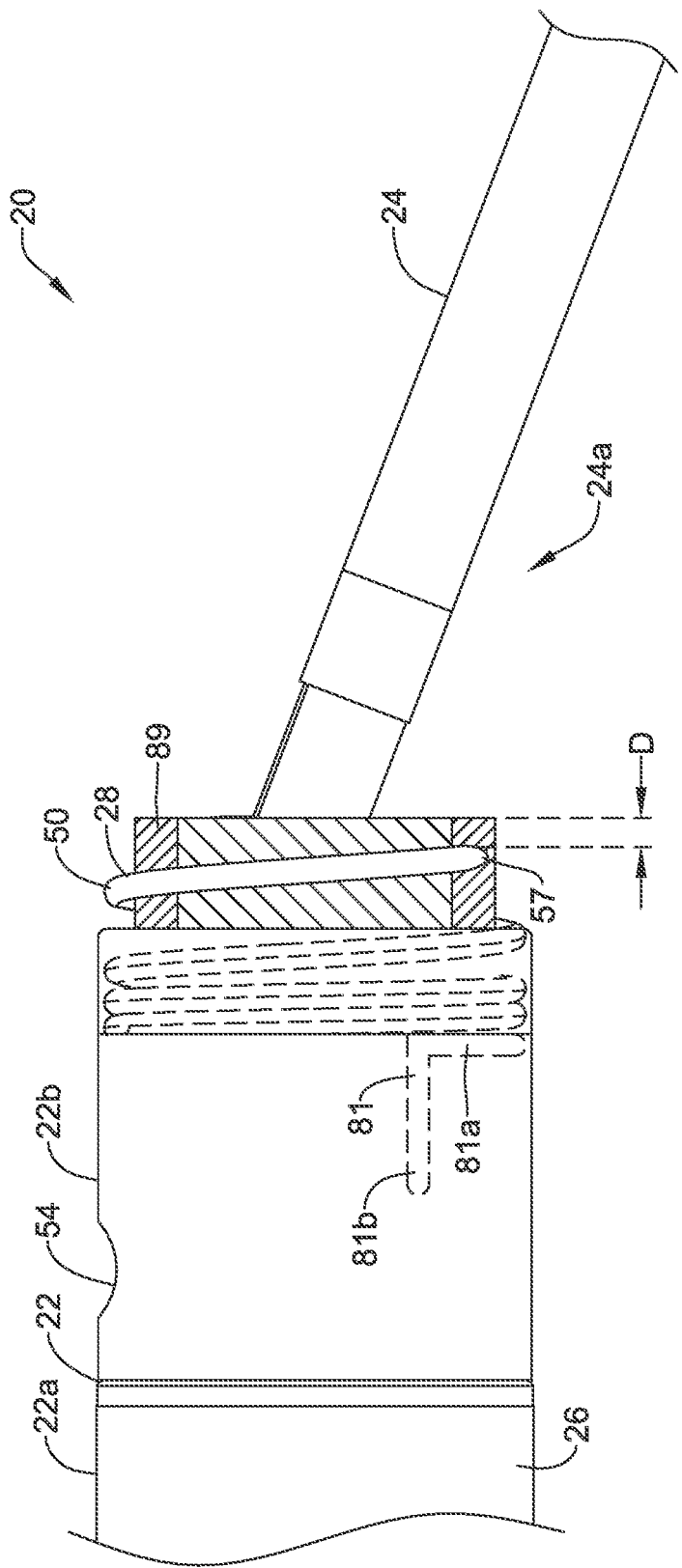
FIG. 19 is a side view of a distal end of an example implantable leadless pacing device having a drug collar.

FIG. 19 a schematic side view of the leadless pacing device 20 having the drug collar 89 extending around the second portion 22b of the housing 22 as depicted in FIG. 19, where the drug collar 89 and the second portion 22b of the housing 22 about which the drug collar 89 is positioned are shown in cross-section. As depicted in FIG. 19, the drug collar 89 may be coupled to the second portion 22b of the housing 22 with a medical-grade adhesive applied to one or more sides of the drug collar 89 facing the second portion 22b of the housing 22 and/or one or more sides of the second portion 22b of the housing 22 facing the drug collar 89. One or more suitable medical-grade adhesives may be utilized as desired including, but not limited to, medical grade silicone.

Figure 20:
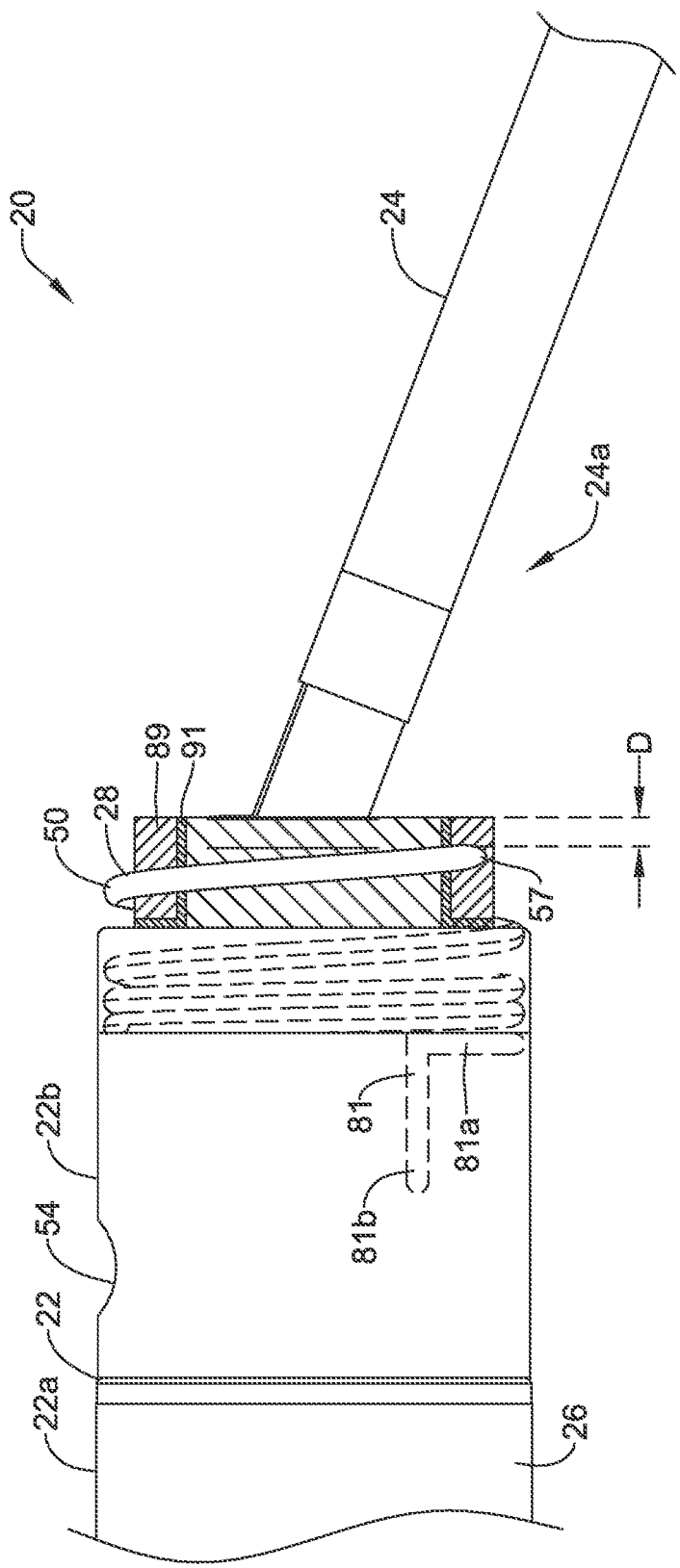
FIG. 20 is a side view of a distal end of an example implantable leadless pacing device having a drug collar.

FIG. 20 is a schematic side view of the leadless pacing device 20 having the drug collar 89 extending around the second portion 22b of the housing 22, where the drug collar 89 and the second portion 22b of the housing 22 about which the drug collar 89 is positioned are shown in cross-section. As depicted in FIG. 20, the drug collar 89 may be coupled to the second portion 22b of the housing 22 with a coupling material interface 91 positioned and/or applied between one or more sides of the drug collar 89 and one or more sides of the second portion 22b of the housing 22. In some cases, the coupling material interface 91 may be L-shaped, but this is not required. The coupling material interface 91 may be configured from one or more suitable materials including, but not limited to, polyetheretherketone (PEEK).

Although FIGS. 19 and 20 depict coupling a drug collar 89 to the housing 22 with an adhesive and a coupling material interface, respectively, other techniques are contemplated for coupling the drug collar 89 to the housing 22. In one example, the drug collar 89 may be coupled to the housing 22 during the forming of the second portion 22b of the housing 22 with an over molding process by positioning the drug collar 89 at a desired location when curing the molded material forming the second portion 22b. Other techniques for coupling the drug collar 89 to the housing 22 are contemplated.

Figure 21:
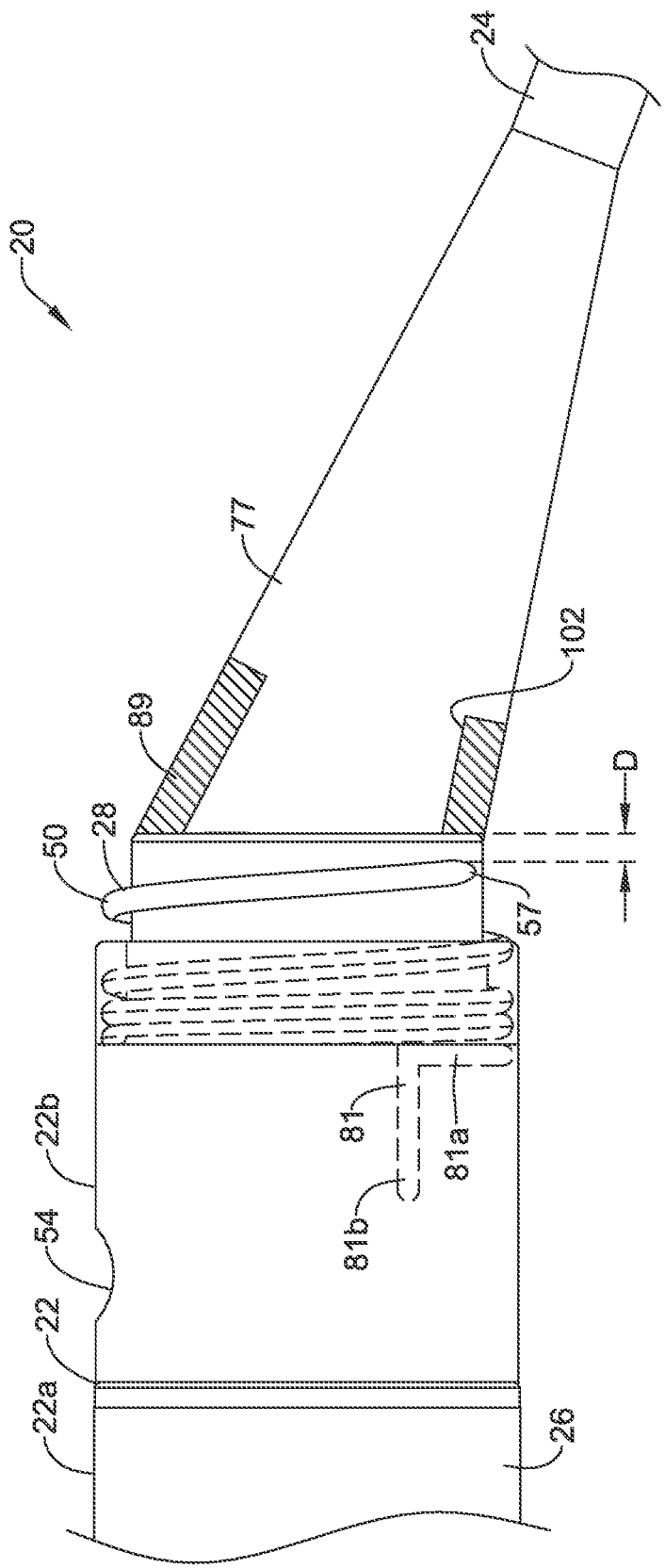
FIG. 21 is a side view of a distal end of an example implantable leadless pacing device having a drug collar at a strain relief feature.

FIG. 21 is a schematic side view of the leadless pacing device 20 with the strain relief 77 and the drug collar 89 extending around the strain relief 77, where the drug collar 89 is shown in cross-section. Although not required, the strain relief 77 may include a recess 102 or other suitable feature for receiving the drug collar 89. In some cases, the recess 102 may extend entirely or at least partially around the strain relief 77 and may be sized such that the drug collar 89 received in the recess 102 may be flush with an outer surface of the strain relief. Other configurations of the recess 102 or other suitable feature for receiving the drug collar 89 are contemplated. The drug collar 89 may be coupled to the strain relief 77 with a medical-grade adhesive applied to one or more sides of the drug collar 89 facing the strain relief 77 and/or one or more sides of the strain relief 77 facing the drug collar 89. One or more suitable medical-grade adhesives may be utilized as desired including, but not limited to, medical grade silicone. The drug collar 89 may be coupled to and/or configured about the strain relief 77 in one or more other suitable manners, as desired.

Figure 22:
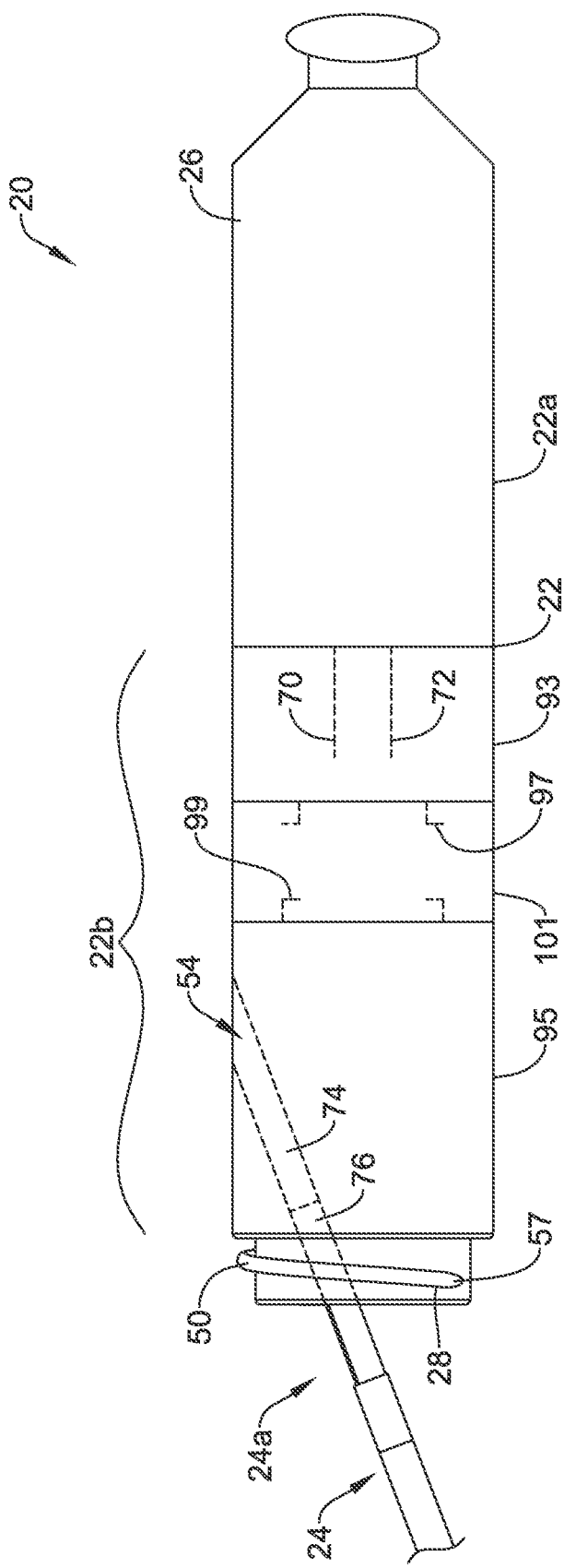
FIG. 22 is a side view of an example implantable leadless pacing device having a housing with a two-part second portion.

FIG. 22 is a schematic side view of the leadless pacing device 20, where the second portion 22b of the housing 22 may be configured from a first sub-portion 93 (e.g., a first header portion) and a second sub-portion 95 (e.g., a second header portion). The first sub-portion 93 may connect directly to or be connected directly to the second sub-portion 95 and/or a third sub-portion 101 may be utilized to facilitate connecting the first sub-portion 93 with the second sub-portion 95.

The first sub-portion 93 may include conductors 70 and 72 extending from the first portion 22a of the housing 22, as depicted in FIG. 22, and/or one or more other suitable components or features. The second sub-portion 95 may include, among other features, the guide wire port 54, the guide wire lumen 74 of the second portion 22b of the housing 22, the distal extension 24, at least a portion of the guide wire lumen 76 of the distal extension 24, the fixation member 50 forming the second electrode 28 and having the distal tip 57, as depicted in FIG. 22, and/or one or more other suitable components or features. Alternatively or additionally, one or more components or features of the first sub-portion 93 or the second sub-portion 95 may be located within the other of the first sub-portion 93 or the second sub-portion 95.

One or both of the first sub-portion 93 and the second sub-portion 95 may be pre-formed and may be configured to engage and couple to one another. In some cases, the first sub-portion 93 may be formed on (e.g., via an over molding process or other suitable technique) or otherwise supported by and/or coupled to the first portion 22a of the housing 22 and may include a first connector 97 configured to engage (e.g., mechanically and/or electrically) the second sub-portion 95.

The second sub-portion 95 may be formed via an over molding process or other suitable technique and may include a second connector 99 configured to engage (e.g., mechanically and/or electrically) the first connector 97 so as to be supported by the first sub-portion 93. The first connector 97 and the second connector 99 are schematically shown in FIG. 22 and may have a keyed relationship or other suitable connector relationship. In some cases, one of the first connector 97 and the second connector 99 may be a female connector and the other of the first connector 97 and the second connector 99 may be a male connector configured to be received by the first connector to create a plugged mechanical and/or electrical connection between the first sub-portion 93 and the second sub-portion 95.

To facilitate a permanent engagement between the first connector 97 and the second connector 99, the first connector 97 and the second connector 99 may be welded or otherwise bonded to one another. Alternatively or additionally, one or more other suitable portions of the first sub-portion 93 and the second sub-portion 95 may be welded or otherwise bonded to one another to facilitate creating a permanent connection between the first sub-portion 93 and the second sub-portion 95.

The third sub-portion 101, when included, may be configured to couple (e.g., mechanically and/or electrically) first sub-portion 93 and the second sub-portion 95 in a permanent or non-permanent manner. In one example, the third sub-portion 101 may be molded over and/or otherwise receive or extend around the first connector 97 and the second connector 99, where the first and second connectors 97, 99 are spaced apart from one another. Alternatively or additionally, the third sub-portion 101 may be molded over and/or otherwise receive or extend around the first connector 97 and the second connector 99, where the first and second connectors 97, 99 may be pre-connected to one another (e.g., connected prior to applying the third sub-portion 101). Further, the third sub-portion 101 may include electrical connectors and, when pre-formed, may act as a female or male plug configured to connect with the first connector 97 and the second connector 99 to create a mechanical and/or electrical connection between the first sub-portion 93 and the second sub-portion 95.

The third sub-portion 101, when included, may be formed via an over molding process or other suitable technique. In some cases, the third-sub-portion 101 may be a pre-formed component configured from a suitable biocompatible metal and/or polymer material. The third sub-portion 101, whether over-molded, pre-formed, or formed in one or more other suitable techniques, may include one or more electrical connectors configured to connect electrical components of or in communication with the first sub-portion 93 with electrical components of or in communication with the second sub-portion 95.

When the first sub-portion 93 and the second sub-portion 95 are coupled to one another (e.g., directly and/or with the third sub-portion 101), electrical components of the sub-portion 93 may be electrically coupled to the second sub-portion 95. In one example, the conductors 70, 72 and/or other conductors of the first sub-portion 93 may be connected to the wires and/or other electrically conductive components carried or supported by the second sub-portion 95 via a plug connection (not shown) that engage when the first sub-portion 93 and the second sub-portions 95 are mechanically connected and/or other suitable connections. Other types of electrical, mechanical, and/or electro-mechanical connections may be made to facilitate electrically connecting electrical components of the first portion 22a of the housing 22 and/or the first sub-portion 93 of the second portion 22b of the housing 22 with the second sub-portion 05 of the second portion 22b of the housing 22.

FIGS. 23-31 depict an example use (e.g., implantation and retrieval) of the leadless pacing device 20 within the heart 10. Although the depicted method includes obtaining access to the patient's heart 10 through the inferior vena cava, access to the heart 10 may also or alternatively be obtained through the superior vena cava and/or other approaches. The view of the heart 10 in FIGS. 23-31 is similar to the view depicted in FIG. 1.

The broken lines depicted in FIGS. 23-31 depict features that may be covered by one or more other features and that would not ordinarily be viewable from the view depicted. The features in broken lines are shown to assist in describing the disclosed concepts. Further, the features within the coronary sinus 15 are depicted in solid lines for clarity purposes although such features would not ordinarily be viewable from the view depicted.

Figure 23:
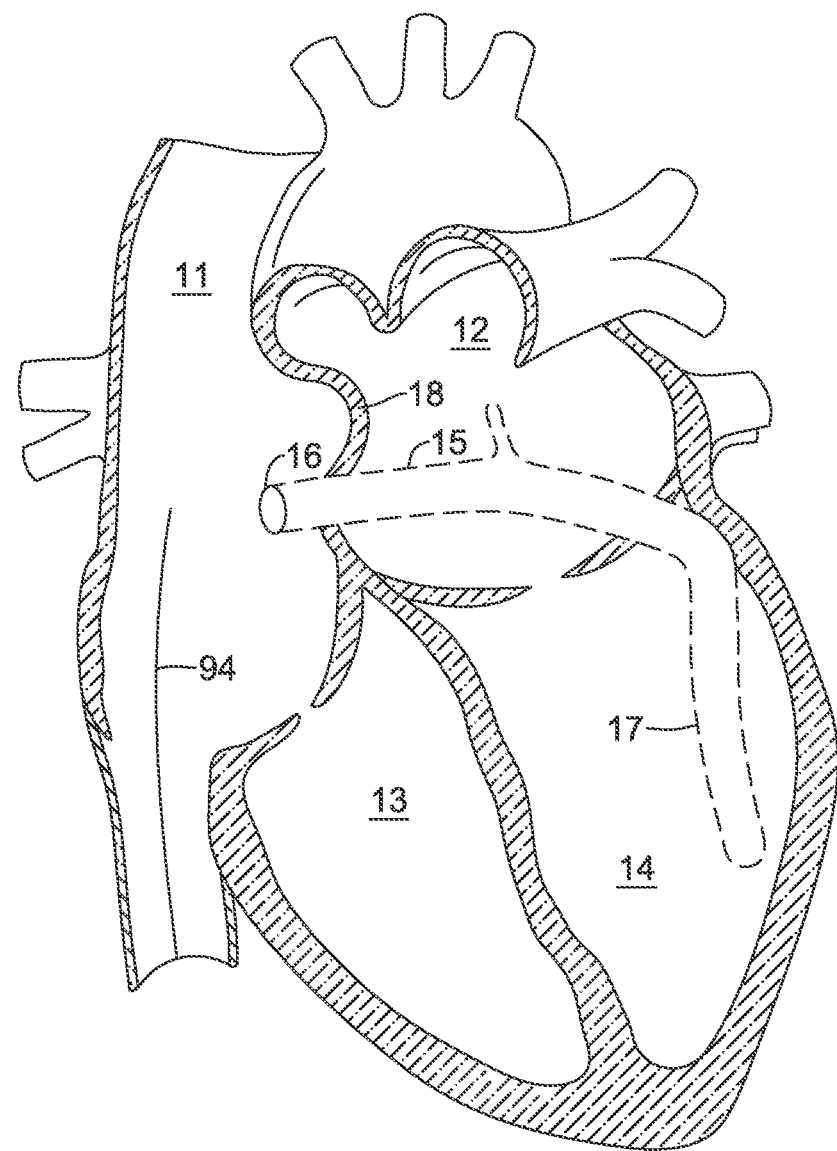
FIGS. 23-31 are a series of schematic diagrams that show delivery and retrieval of an example implantable leadless pacing device into and from a patient's heart.

In some embodiments, implanting the leadless pacing device 20 within the heart 10 may begin by positioning a guide wire within heart 10, such as a first guide wire 94 depicted in FIG. 23. The first guide wire 94 may have a 0.035 inch diameter and/or have one or more other suitable diameters for gaining access to the heart 10. The first guide wire 94 may gain access to the heart 10 through an opening in the patient's skin extending into an artery or vein (e.g., the femoral vein or other vessel) that has been dilated with an introducer or other device having a dilation feature (e.g., using a catheter 80 and the dilator 86 depicted in FIG. 24) and advancing the first guide wire 94 to and/or through the inferior vena cava or other body vessel.

In some instances, the first guide wire 94 may have one or more radiopaque markers disposed on an end of the first guide wire 94. Such radiopaque markers may allow for easier viewing of the first guide wire 94 through one or more medical imaging systems as the first guide wire 94 is maneuvered into position with the heart 10. In some embodiments, the radiopaque markers may be spaced apart from each other by a known distance. In such embodiments, by counting the number of radiopaque markers between two features within the heart 10, a distance may be determined between the two features. In some embodiments, the leadless pacing device 20 may be manufactured in a variety of sizes, or various portions of the leadless pacing device 20, such as the housing 22 and the distal extension 24, may be manufactured in various sizes and lengths. By determining a distance between different features of the patient's heart 10, for instance between the coronary sinus ostium 16 and the septum 18 in the right atrium 11, as depicted in FIG. 23, an appropriate sized housing 22 or distal extension 24 may be selected for the particular patient.

Figure 24:
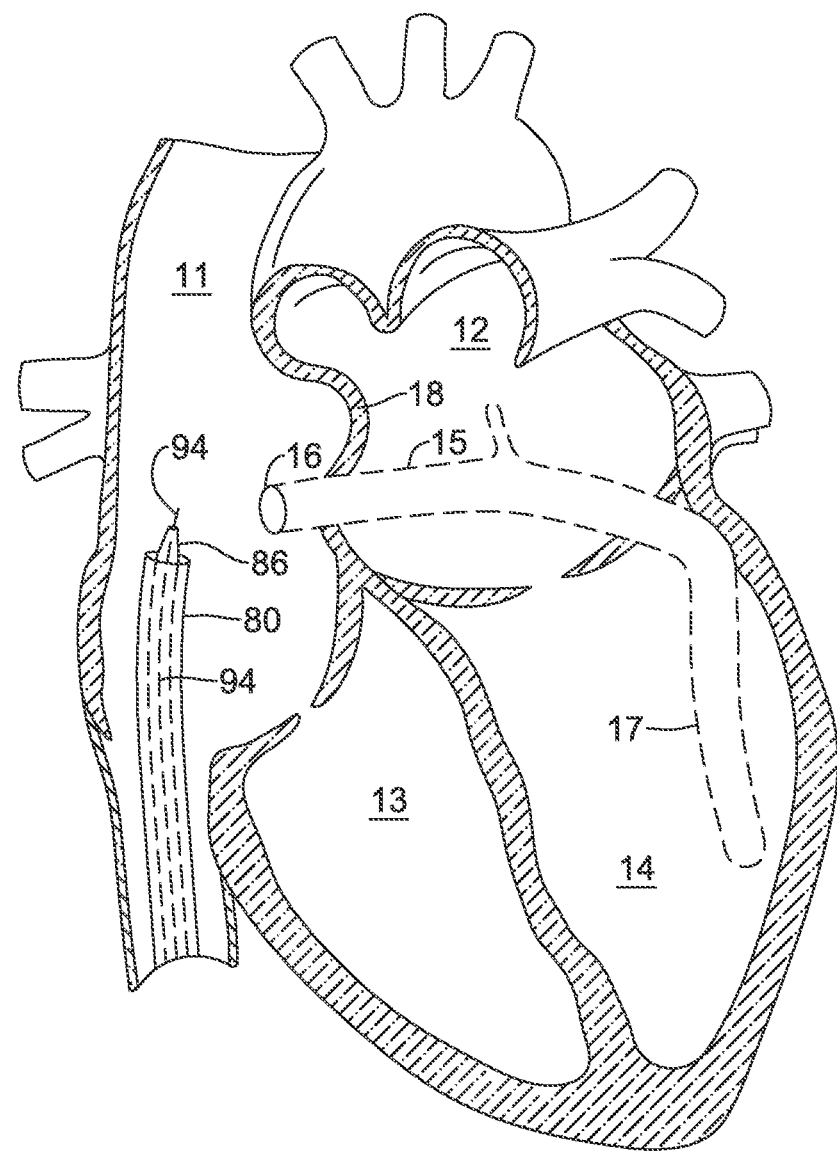

After measuring distances between various features of the heart 10, or in embodiments where such measurements are not needed, the catheter 80 (e.g., an introducer) and the dilator 86 may be maneuvered over the first guide wire 94 into the heart 10, as depicted in FIG. 24. In some cases, the catheter 80 may be steerable and the dilator 86 may be located at or adjacent a distal end (e.g., at or adjacent a distal tip) of the catheter 80. The dilator 86 may be configured to engage the ostium 16 of the coronary sinus 15 and dilate and/or cannulate the coronary sinus 15 such that the catheter 80 and/or the leadless pacing device 20 may be received therein. Alternatively or in addition, the catheter 80 may have a pre-formed bend at or adjacent a distal end of the catheter 80. In such cases, the dilator 86 may be inserted through the distal end of the catheter 80 to straighten the distal end of the catheter 80 during insertion of the catheter into the heart 10. Then, when the distal end of the catheter 80 is within the heart, such as the right atrium 11, the dilator 86 maybe withdrawn such that the distal end of the catheter 80 bends so as to face and/or extend into the coronary sinus 15 and direct the first guide wire 94 toward and/or into the coronary sinus 15.

Figure 25:
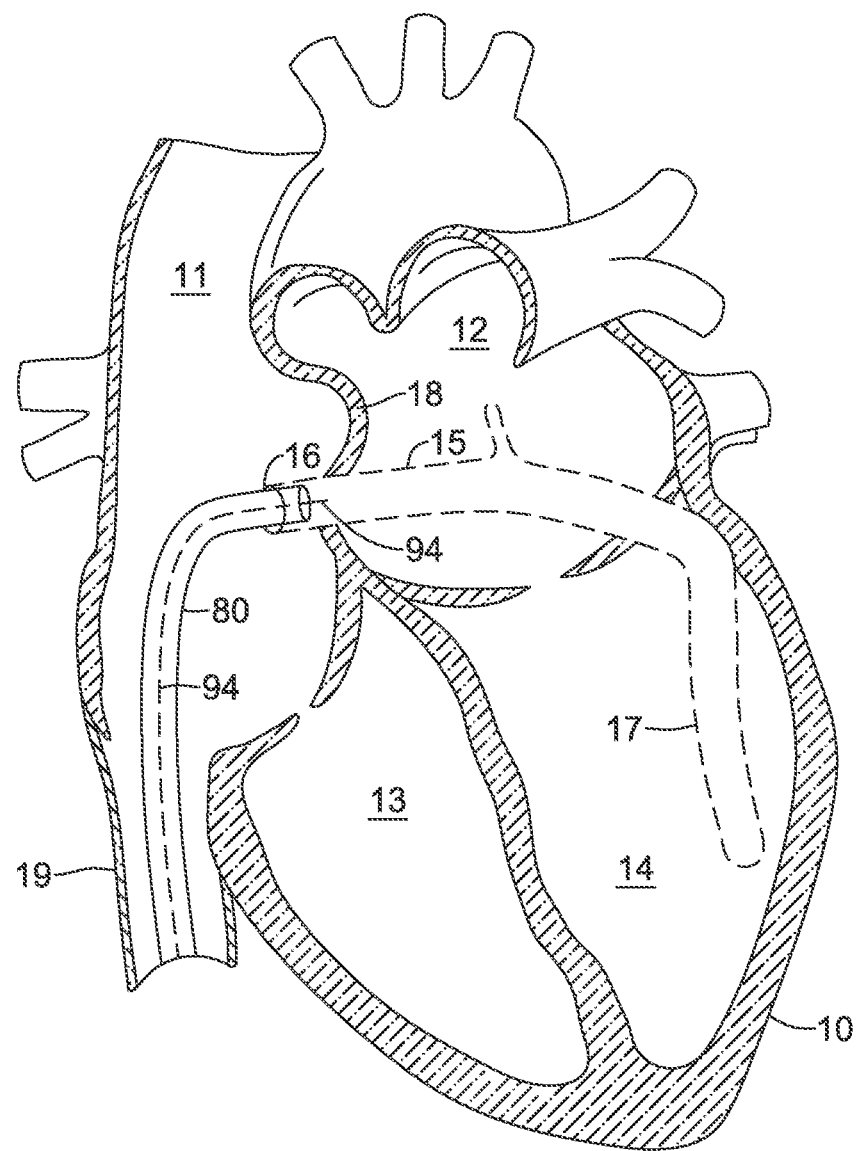

FIG. 25 depicts the catheter 80 and the first guide wire 94 bent and inserted into the coronary sinus 15 after withdrawal of the dilator 86 through the catheter 80. In some cases, after the catheter 80 is bent toward the coronary sinus 15, the first guide wire 94 may be advanced into the coronary sinus and the catheter 80 may be advanced along the first guide wire 94 and into the coronary sinus 15.

The dilator 86 may take on the structure of a conical tapered tip, such that advancing the catheter 80 and the dilator 86 into the coronary sinus 15 expands the inner diameter of the coronary sinus 15. In another example, the dilator 86 may be rounded or may have a more abrupt taper than a conical taper. Other dilator configurations are contemplated and any configuration suitable for dilating the coronary sinus 15 may be utilized. As such, if the coronary sinus 15 needs to be expanded to receive the leadless pacing device 20, the distal end or distal tip of the catheter 80 and/or the dilator 86 may be advanced through the ostium 16 of the coronary sinus 15 to dilate the coronary sinus 15 a suitable amount sufficient to receive the leadless pacing device 20. In addition to or as an alternative to the catheter 80 and/or the dilator 86, one or more other catheters, dilators, or introducers may be used to facilitate dilating, cannulating, and/or otherwise entering the coronary sinus 15.

FIG. 25 depicts the catheter 80 and the first guide wire 94 bent and inserted into the coronary sinus 15 after withdrawal of the dilator 86 through the catheter 80. In some cases, after the catheter 80 is bent toward the coronary sinus 15, the first guide wire 94 may be advanced into the coronary sinus and the catheter 80 may be advanced along the first guide wire 94 and into the coronary sinus 15.

Figure 26:
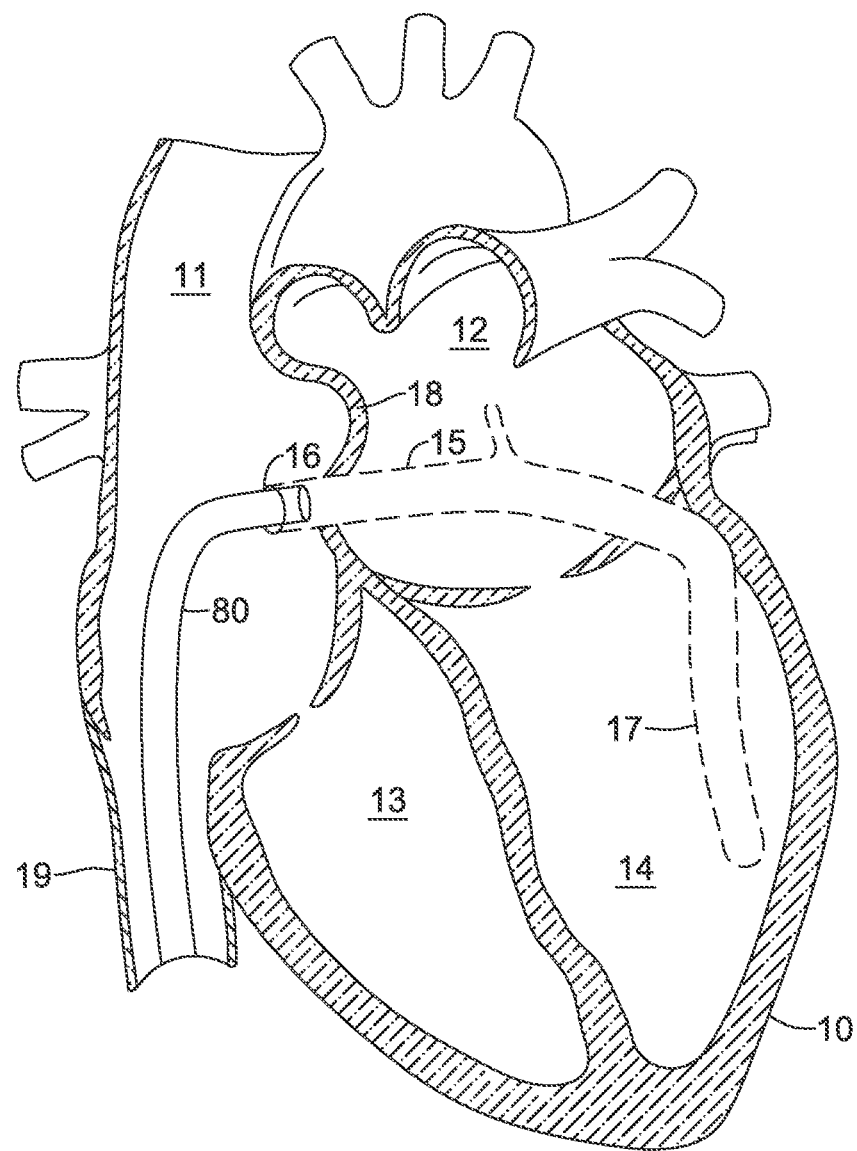
Figure 27:
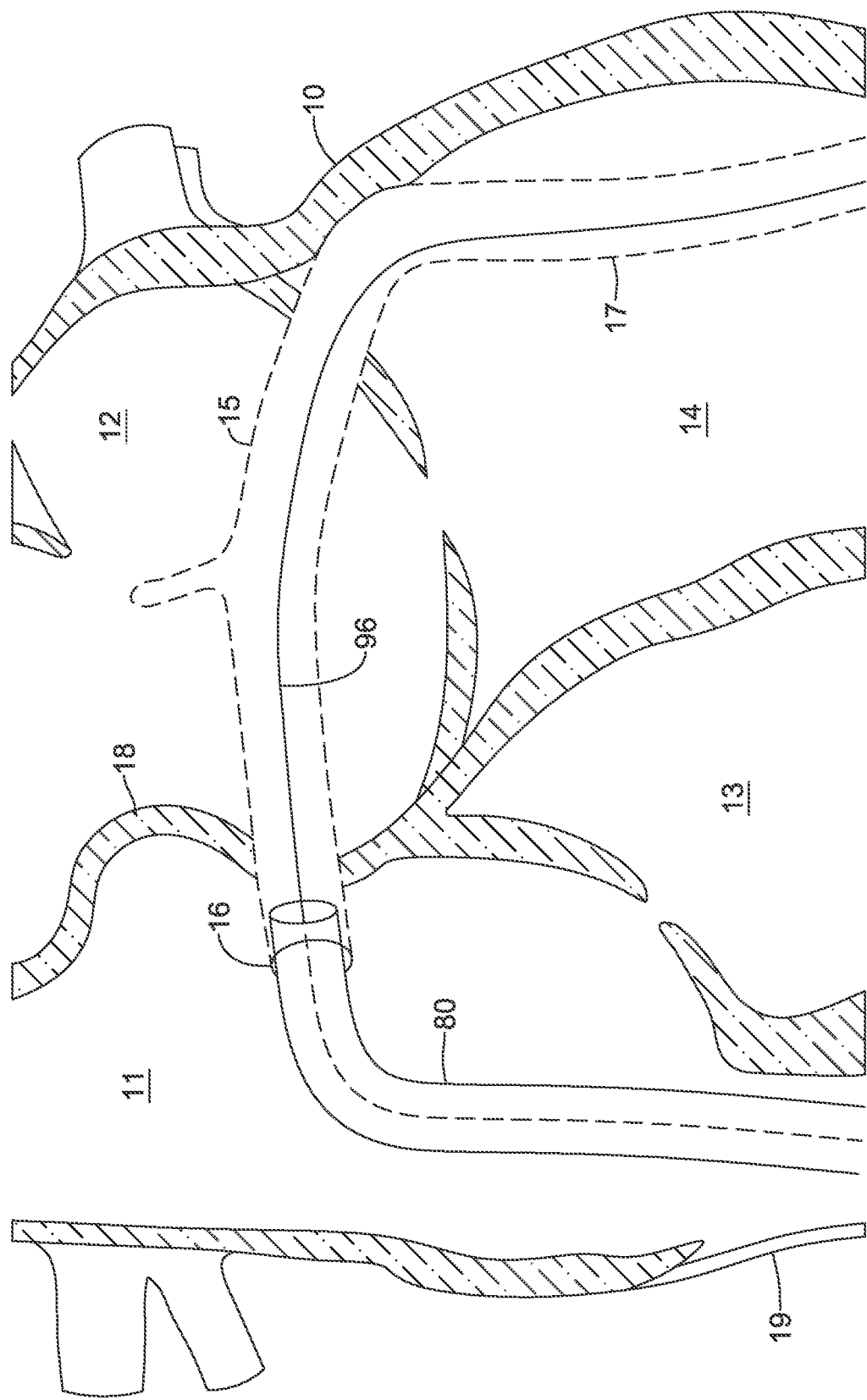

Once the coronary sinus 15 has been cannulated and the catheter 80 inserted therein, the first guide wire 94 may then be removed from the catheter 80, as depicted in FIG. 26. In some instances, a second guide wire 96 may be inserted into the catheter 80 and maneuvered all the way through coronary sinus 15 and into the great cardiac vein 17 or other vessel extending from the coronary sinus 15, as depicted in FIG. 27. The second guide wire 96 may have a diameter of about 0.014 inches and/or other suitable diameter for navigating vessels of and/or extending around the heart 10 (e.g., for navigating the great cardiac vein 17 and/or other vessels extending from or to the great cardiac vein 17).

Figure 28:
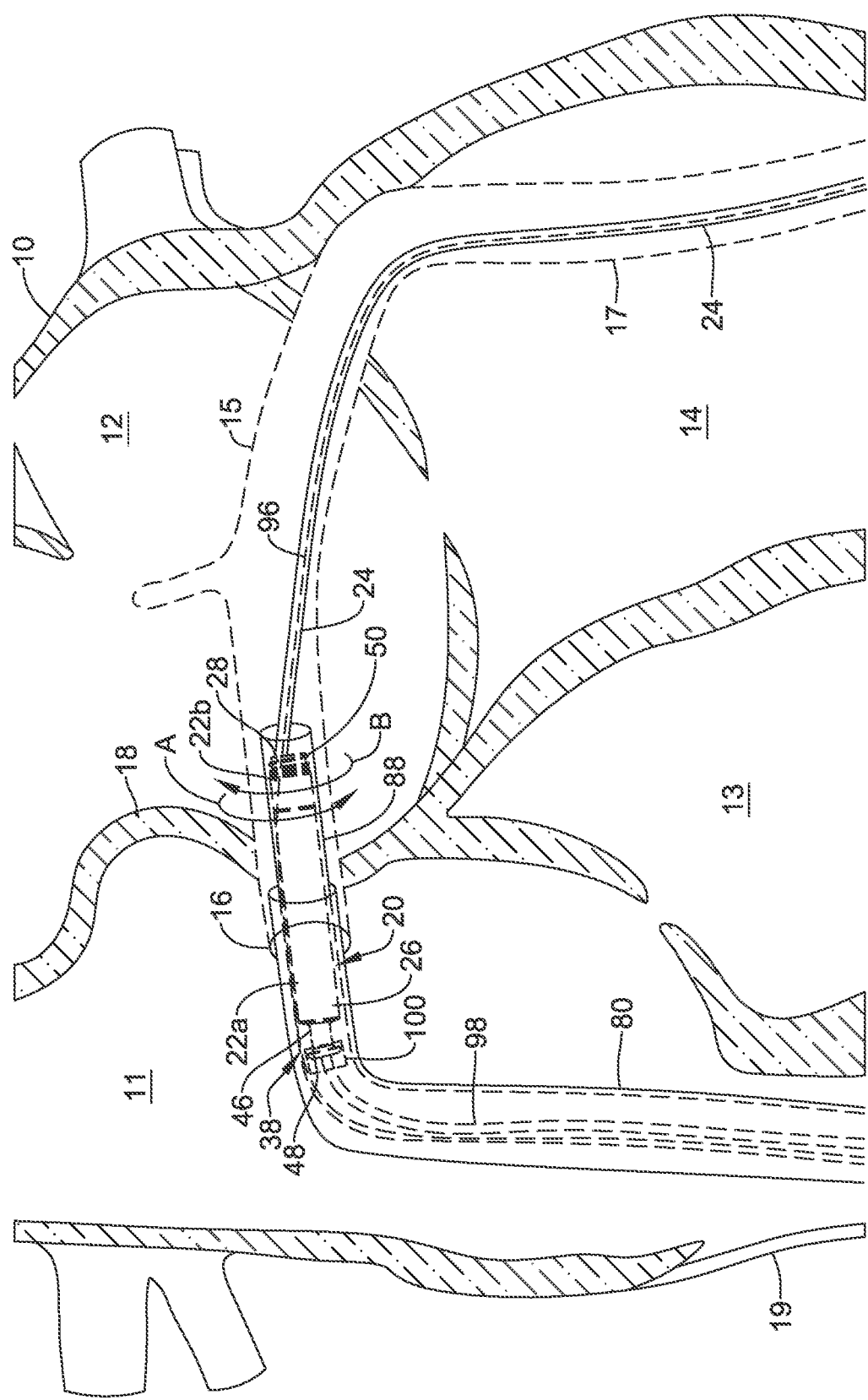

FIG. 28 depicts the catheter 80 and the leadless pacing device 20 within a delivery/retrieval catheter 88 positioned within the coronary sinus 15 with the distal extension 24 tracked over the second guide wire 96 into the great cardiac vein or other cardiac vessel. The second guide wire 96 may exit the guide wire port of the housing 22 and extend along an exterior of the proximal portion 22a of the housing 22. The first portion 22a of the housing 22 of the leadless pacing device 20 and the proximal member 38 may extend proximally out of the coronary sinus 15 into the right atrium 11, with the positioning device 98 and the interlocking mechanism 100 connected to the proximal member 38. The leadless pacing device 20 may be advanced to this position by pushing the leadless pacing device 20 and the delivery/retrieval catheter 88 through the catheter 80 and over the second guide wire 96 with the positioning device 98 while the interlocking mechanism 100 is connected to the proximal member 38. Alternatively, only one of the catheter 80 or the second guide wire 96 may be utilized to position the leadless pacing device 20 and the delivery/retrieval catheter 88. Further, it is contemplated that the leadless pacing device 20 may be positioned with neither of the catheter 80 nor the second guide wire 96. In some cases, the interlocking mechanism 100 may be connected to or may engage the proximal member 38 until it is positively or intentionally released or disconnected via interacting with a proximal end of the positioning device 98.

Once the leadless pacing device 20, the delivery/retrieval catheter 88, and the catheter 80 have been position within the coronary sinus 15 adjacent a target location, the leadless pacing device 20 within the delivery/retrieval catheter 88 may be rotated to position the distal tip 57 of the fixation member 50 at a desired location for puncturing and engaging tissue of a patient's heart that forms a chamber of the wall (e.g., at a position similar to the position depicted in FIG. 15A and/or at one or more other suitable positions). An orientation of the leadless pacing device 20 within the coronary sinus 15 and/or within the delivery/retrieval catheter 88 may be adjusted via interacting with a proximal end of the positioning device 98 and/or may be adjusted in a different suitable manner. In some cases, the orientation of the leadless pacing device 20 within the coronary sinus 15 and/or within the delivery/retrieval catheter 88 may be adjusted by adjusting a position of the leadless pacing device 20 in a longitudinal direction and/or by rotating the leadless pacing device 20 in a direction of arrow A and/or arrow B using the positioning device 98.

In some cases, a rotational and/or longitudinal position of the distal tip 57 may be known or identifiable from one or more radiopaque markers and the known rotational and/or longitudinal position may be utilized for positioning the distal tip 57. In one example, the distal tip 57 may be or may include a radiopaque marker identifiable on one or more imaging systems to facilitate proper alignment of the distal tip 57 of the fixation member 50. Alternatively or additionally, the fixation member 50 may include one or more other radiopaque features (e.g., the tail 81 and/or other suitable radiopaque feature) and/or the leadless pacing device 20 may include one or more radiopaque markers having a known relationship with the distal tip 57 that may be used to position the distal tip 57 at the desired location. In one example, the distal tip 57 may have a first circumferential position, the tail 81 of the fixation member 50 may have a second circumferential position at a predetermined angular orientation from the first circumferential position that may be used to facilitate rotationally aligning the distal tip 57 with target tissue of the heart. Rotation of the leadless pacing device 20 to rotationally align the distal tip 57 with target tissue of the heart may be performed while the distal tip 57 remains within the lumen of the delivery/retrieval catheter 88 to prevent unintentional penetration of the distal tip with tissue, and thereafter the fixation member 50 may be deployed out of the distal end of the delivery/retrieval catheter. Alternatively or additionally, the leadless pacing device 20 may be rotated in a counter direction of the helical anchor of the fixation member after deploying the distal tip of the fixation member 50 out of the distal end of the delivery/retrieval catheter to prevent unintentional penetration of the distal tip with tissue.

Figure 29:
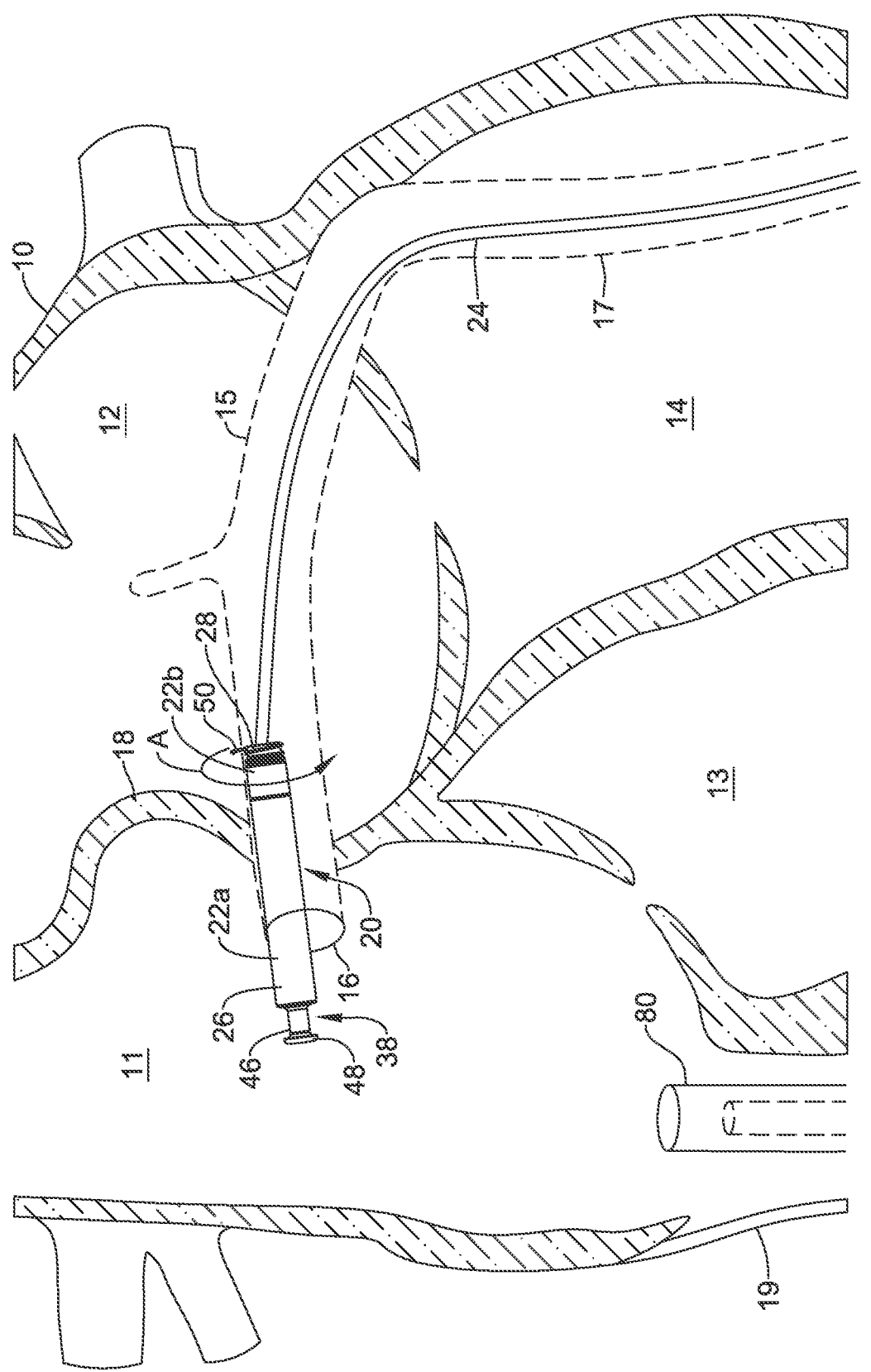

Once the leadless pacing device 20 is in position, the catheter 80 and the second guide wire 96 may be retracted and the leadless pacing device 20 may be further rotated using the positioning device 98 (e.g., in the direction of arrow A and/or other suitable direction) such that the distal tip 57 and the fixation member 50 engage tissue forming a wall of a chamber of a heart 10 (e.g., in a manner similar to as depicted in FIG. 15B and/or in one or more other suitable manners). In some instances, the leadless pacing device 20 may be oriented such that the distal tip 57 initially penetrates into the left atrial muscle. Once the fixation member 50 is engaging the tissue forming the wall of the heart 10, the positioning device 98 and the delivery/retrieval catheter 88 may be retracted and, optionally, removed from the heart 10. FIG. 29 depicts an example of how the leadless pacing device 20 may be positioned after the positioning device 98, the delivery/retrieval catheter 88, the catheter 80, and the second guide wire 96 have been retracted and the fixation member 50 has engaged the tissue forming the wall of the heart 10. Although the housing 22 of the leadless pacing device 20 is depicted as extending along the right atrium 11 and the left atrium 12 in the coronary sinus 15, the housing 22 of the leadless pacing device 20 may be entirely positioned along the right atrium 11 or entirely along the left atrium 12 within the coronary sinus 15. In some instances the housing 22 of the leadless pacing device 20 may be located along both of the right atrium 11 and the left atrium 12 such that at least part of the first electrode 26 is in contact with tissue of the right atrium 11 and at least part of the second electrode 28 is in contact with tissue of the left atrium 12. In such instances, the leadless pacing device 20 may be programmed to sense and/or pace one or more of the right atrium 11 and left atrium 12 with the respective electrodes 26, 28 or other electrodes due to the electrodes being bipolar.

Figure 30:
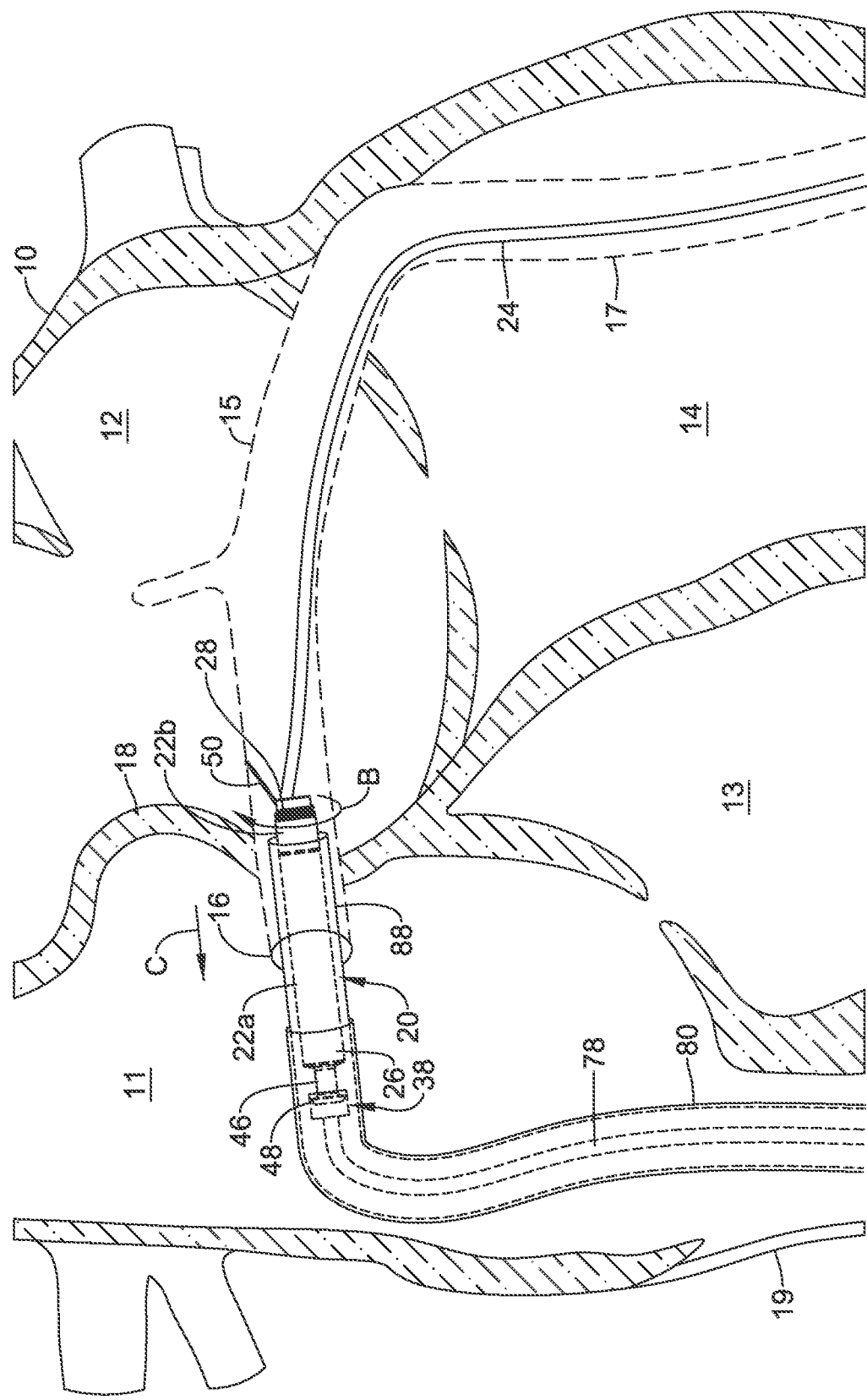

In some cases, the implanted leadless pacing device 20 may be removed from the coronary sinus 15 and/or the positioning of the implanted leadless pacing device 20 may be adjusted. FIG. 30 depicts the delivery/retrieval catheter 88 and a retrieval device 78 (e.g., a positioning device, which may be or may not be the positioning device 98 or similar to the positioning device 98) inserted into the coronary sinus 15, with the retrieval device 78 engaging the proximal member 38 of the leadless pacing device 20 via an interlocking mechanism (e.g., an interlocking mechanism similar to the interlocking mechanism 100 and/or other suitable interlocking mechanism). Once the retrieval device 78 has engaged the proximal member 38 of the leadless pacing device 20, the retrieval device 78 may apply a force to the leadless pacing device causing the leadless pacing device to rotate in a direction of arrow B or other suitable direction. Rotation of the leadless pacing device 20 may result in the fixation member 50 at least partially withdrawing from engagement with the tissue forming the wall of a chamber of the heart 10.

In addition to or as an alternative to rotating the leadless pacing device 20 in the direction of arrow B, a force may be applied to the leadless pacing device 20 in a direction of arrow C (e.g., a longitudinal direction). When the fixation member 50 is still engaged with the tissue of the heart, applying a force to the leadless pacing device 20 in the longitudinal direction of arrow C may cause the fixation member 50 to elongate (e.g., straighten and/or elongate in one or more other suitable manners), as shown in FIG. 30 and facilitate removing the fixation member 50 from tissue of the heart 10. Depending on the material configurations utilized, an axial force in the range of about 0.1-1.0 pound-force (lbf), in the range of about 0.1-0.5 lbf, at least about 0.25 lbf, at least about 0.50 lbf, at least about 0.25 lbf but less than about 1.0 lbf, and/or other suitable force amount may be utilized to elongate the fixation member 50. In some instances, the fixation member 50 may be plastically deformed into a straightened configuration by applying the axial force in the direction of arrow C for removal from the tissue.

Figure 31:
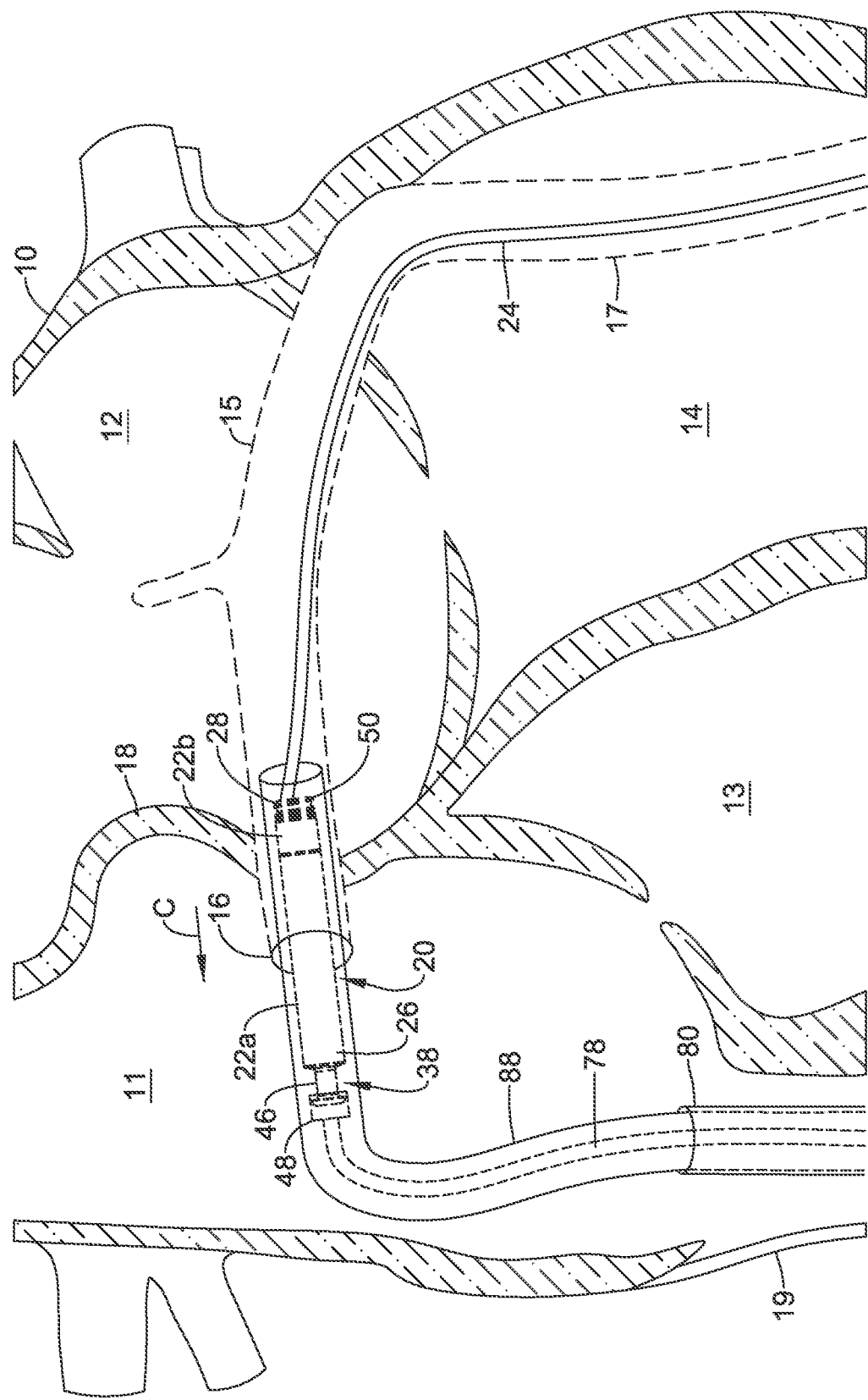

After the fixation member 50 has been completely removed from the tissue of the heart 10 as shown in FIG. 31, the delivery/retrieval catheter 88 may be advanced over a portion of or an entirety of the leadless pacing device 20 via relative movement of the retrieval device 78 and the delivery/retrieval catheter 88. Once covered by the delivery/retrieval catheter 88, the leadless pacing device 20 may be completely withdrawn from the coronary sinus 15 and the patient's heart 10 by applying a further force in the direction C and/or repositioned (e.g., to improve positioning of electrodes of the leadless pacing device 20 and/or for one or more other suitable reasons) within the coronary sinus 15 and/or the vessels in communication with the coronary sinus 15 by applying a rotational force in direction A to re-engage the fixation member 50 with the myocardial tissue adjacent the coronary sinus 15.

In some cases, an introducer sheath (e.g., the catheter 80 or other suitable sheath) may be inserted into the vasculature of the patient (e.g., into the coronary sinus 15) and positioned over at least part of the leadless pacing device 20 and/or the delivery/retrieval catheter to facilitate withdrawing the leadless pacing device 20 from the coronary sinus 15. In such cases, the introducer sheath may be positioned at a location covering a proximal end of the leadless pacing device 20 and delivery/retrieval catheter 80 and/or the retrieval device 78 may be advanced through the introducer sheath to the leadless pacing device 20 at least partially covered by the introducer sheath. The positioning of the introducer sheath over the proximal end of the leadless pacing device 20 may include deflecting a distal end portion of the introducer sheath into the coronary sinus 15 and steering the introducer sheath over the proximal end of the leadless pacing device 20. The deflection and steering of the introducer sheath may be effected by manipulating one or more control features adjacent a proximal end of the introducer sheath and/or the introducer sheath may have a pre-formed bend configured to bend toward the coronary sinus 15.

Those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules.

Although various features may have been described with respect to less than all embodiments, this disclosure contemplates that those features may be included on any embodiment. Further, although the embodiments described herein may have omitted some combinations of the various described features, this disclosure contemplates embodiments that include any combination of each described feature. Accordingly, departure in form and detail may be made without departing from the scope and spirit of the present disclosure as described in the appended claims.

What is claimed is:

1. A leadless pacing device for delivering electrical stimulation to a heart of a patient, the leadless pacing device comprising:
   a housing having a central longitudinal axis, the housing comprising:
      a body portion; and
      a header extending distally from the body portion;
   a fixation member affixed to the header and extending therefrom; and
   a distal extension connected to the header at a fixed orientation such that the distal extension exits a distal end of the header at an oblique angle to the central longitudinal axis and extends distally from the distal end of the header;
   wherein the housing is configured to be rotated to engage the fixation member with a body tissue and axially displaced along a longitudinal axis of the housing to disengage the fixation member from the body tissue;
   wherein the fixation member includes a helical anchor having a helical configuration in a relaxed state for engagement with the body tissue and is configured to elongate to a straightened configuration for disengagement from the body tissue in response to an axial force applied thereto.

2. The leadless pacing device of claim 1, wherein the fixation member is configured to elongate to the straightened configuration in response to an axial force applied thereto that is in a range of 0.1 pound-force (lbf) to 1.0 lbf.

3. The leadless pacing device of claim 2, wherein the fixation member is plastically deformed to the straightened configuration in response to the axial force.

4. The leadless pacing device of claim 3, wherein the fixation member is formed from a platinum iridium material.

5. The leadless pacing device of claim 1, wherein the helical anchor extends at least partially around an exterior surface of the header in the helical configuration.

6. The leadless pacing device of claim 5, further comprising:
   a drug collar positioned at least partially around the header.

7. The leadless pacing device of claim 6, wherein the drug collar is at least partially positioned between the fixation member and the exterior surface of the header.

8. The leadless pacing device of claim 6, wherein the drug collar is secured to the header with one or both of a medical grade adhesive and an interface comprising polyetheretherketone (PEEK).

9. The leadless pacing device of claim 1, wherein the header extends distal of a distal tip of the helical anchor in the helical configuration.

10. The leadless pacing device of claim 1, wherein the helical anchor comprises:
   a proximal portion embedded within a proximal portion of the header;
   a helical coil portion surrounding and radially spaced outward from an outer surface of a distal portion of the header; and
   a distal tip forming a terminal end of the fixation member;
   wherein the distal tip is located proximal of a distal end of the header.

11. A leadless pacing device for delivering electrical stimulation to a heart of a patient, the leadless pacing device comprising:
   a housing having a central longitudinal axis, the housing comprising:
      a body portion; and
      a header extending distally from the body portion, the header comprises a first header portion connected to the body portion and a second header portion extending distally from the first header portion, the first header portion mechanically coupled to the second header portion with one or more connectors;
   a fixation member having a proximal portion and a helical portion, wherein the proximal portion is secured to the second header portion, and the helical portion extends helically around the second header portion; and a distal extension rigidly connected to the second header portion and extending distally from a distal end of the second header portion at a nonparallel angle to the central longitudinal axis;

wherein the helical portion of the fixation member is configured to elongate to a straightened configuration in response to an axial force applied thereto.

12. The leadless pacing device of claim 11, wherein the fixation member is configured to elongate to the straightened configuration in response to an axial force applied thereto that is in a range of 0.1 pound-force (lbf) to 1.0 lbf.

13. The leadless pacing device of claim 12, wherein the fixation member is plastically deformed to the straightened configuration in response to the axial force.

14. The leadless pacing device of claim 13, wherein the fixation member is formed from a platinum iridium material.

15. The leadless pacing device of claim 11, wherein the second header portion is molded over a proximal end of the distal extension.

16. The leadless pacing device of claim 11, wherein the nonparallel angle relative to the central longitudinal axis is an oblique angle relative to the central longitudinal axis of the housing.

17. The leadless pacing device of claim 11, wherein the header extends distal of a distal tip of the fixation member.

18. The leadless pacing device of claim 11, wherein the distal extension comprises a plurality of axially-spaced apart electrodes.

19. The leadless pacing device of claim 1, wherein the fixation member comprises a tail embedded within a proximal portion of the header, the tail comprising a radially extending portion and a proximally extending portion.

20. A leadless pacing device for delivering electrical stimulation to a heart of a patient, the leadless pacing device comprising:

a housing having a central longitudinal axis, the housing comprising:
   a body portion; and
   a header extending distally from the body portion, the header comprises a first header portion connected to the body portion and a second header portion extending distally from the first header portion, the first header portion formed of a first material and the second header portion formed of a second material, the first material being different from the second material;

a fixation member having a proximal portion and a helical portion, wherein the proximal portion is secured to the second header portion, and the helical portion extends helically around the second header portion; and a distal extension fixedly mounted to the header at a fixed orientation and extending distally from a distal end of the header at an oblique angle to the central longitudinal axis;

wherein the helical portion of the fixation member is configured to elongate to a straightened configuration in response to an axial force applied thereto.

* * * * *